US011963981B2

(12) United States Patent
Pulé et al.

(10) Patent No.: US 11,963,981 B2
(45) Date of Patent: *Apr. 23, 2024

(54) CHIMERIC ANTIGEN RECEPTOR

(71) Applicant: AUTOLUS LIMITED, London (GB)

(72) Inventors: Martin Pulé, London (GB); Evangelia Kokalaki, London (GB); Shaun Cordoba, London (GB); Shimobi Onuoha, London (GB); Simon Thomas, London (GB); Biao Ma, London (GB); Mathieu Ferrari, London (GB)

(73) Assignee: AUTOLUS LIMITED, London (GB)

(*) Notice: Subject to any disclaimer, the term of this patent is extended or adjusted under 35 U.S.C. 154(b) by 661 days.

This patent is subject to a terminal disclaimer.

(21) Appl. No.: 17/054,670

(22) PCT Filed: May 15, 2019

(86) PCT No.: PCT/GB2019/051330
§ 371 (c)(1),
(2) Date: Nov. 11, 2020

(87) PCT Pub. No.: WO2019/220109
PCT Pub. Date: Nov. 21, 2019

(65) Prior Publication Data
US 2021/0113618 A1 Apr. 22, 2021

(30) Foreign Application Priority Data
May 15, 2018 (GB) .................... 1807866
Jun. 14, 2018 (GB) .................... 1809773

(51) Int. Cl.
A61K 35/17 (2015.01)
A61P 35/00 (2006.01)
C07K 16/28 (2006.01)

(52) U.S. Cl.
CPC .............. A61K 35/17 (2013.01); A61P 35/00 (2018.01); C07K 16/2803 (2013.01); C07K 2317/565 (2013.01); C07K 2317/622 (2013.01); C07K 2317/76 (2013.01)

(58) Field of Classification Search
None
See application file for complete search history.

(56) References Cited

U.S. PATENT DOCUMENTS

| 10,457,730 | B2 | 10/2019 | Pule et al. |
| 11,091,532 | B2 | 8/2021 | Pule et al. |
| 11,180,553 | B2 | 11/2021 | Onuoha et al. |
| 11,590,170 | B2* | 2/2023 | Pulé ............ A61P 35/00 |
| 2016/0130357 | A1 | 5/2016 | Mukherjee |
| 2016/0296562 | A1 | 10/2016 | Pule et al. |
| 2016/0333114 | A1 | 11/2016 | Williams et al. |
| 2016/0361360 | A1 | 12/2016 | Chang et al. |
| 2016/0362472 | A1 | 12/2016 | Bitter et al. |
| 2017/0157176 | A1 | 6/2017 | Wang et al. |
| 2017/0275362 | A1 | 9/2017 | Brentjens et al. |
| 2018/0044417 | A1 | 2/2018 | Pule et al. |
| 2019/0038672 | A1 | 2/2019 | Pule et al. |
| 2019/0177412 | A1 | 6/2019 | Onuoha et al. |
| 2019/0330337 | A1 | 10/2019 | Pule et al. |
| 2020/0140544 | A1 | 5/2020 | Pule et al. |
| 2021/0187026 | A1 | 6/2021 | Pule et al. |

FOREIGN PATENT DOCUMENTS

| WO | WO-2015/075468 A1 | 5/2015 |
| WO | WO-2015/075469 A1 | 5/2015 |
| WO | WO-2015/075470 A1 | 5/2015 |
| WO | WO-2015/142675 A2 | 9/2015 |
| WO | WO-2015/150771 A1 | 10/2015 |
| WO | WO-2016/030691 A1 | 3/2016 |
| WO | WO-2016/102965 A1 | 6/2016 |
| WO | WO-2016/124930 A1 | 8/2016 |
| WO | WO-2016/139487 A1 | 9/2016 |
| WO | WO-2016/149578 A1 | 9/2016 |
| WO | WO-2016/151315 A1 | 9/2016 |
| WO | WO-2017/216561 A1 | 12/2017 |
| WO | WO-2017/216562 A1 | 12/2017 |
| WO | WO-2019/220110 A1 | 11/2019 |
| WO | WO-2021/224629 A1 | 11/2021 |

OTHER PUBLICATIONS

Qin et al., Molecular Therapy Oncolytics 11:127-137 (Year: 2018).*
Spiegel et al., Nature Medicine 27:1419-31 (Year: 2021).*
Kokalaki et al., Mol. Therapy 31(7):2089-2104 (Year: 2023).*
Roddie et al., Blood 141(20): 2470-2482 (Year: 2023).*
Wei et al., Cancer Immunol Res 9:1061-70 (Year: 2021).*
Almagro & Fransson, Frontiers Immunol 8:1751; doi:10.3389/fimmu.2017.01751 (Year: 2018).*
Faraji F., et al., "Development and Characterization of a Camelid Single-Domain Antibody Directed to Human CD22 Biomarker", Biotechnology and Applied Biochemistry, Academic Press, Apr. 6, 2018, vol. 65, No. 5, XP071713814, ISSN: 0885-4513, DOI: 10.1002/BAB.1654, pp. 718-725.
Xiao X., et al., "Identification and Characterization of Fully Human Anti-CD22 Monoclonal Antibodies," Monoclonal Antibodies (MAbs), May/Jun. 2009, vol. 1 (3), pp. 297-303.
Haso et al., "Anti-CD22-Chimeric Antigen Receptors Targeting B Cell Precursor Acute Lymphoblastic Leukemia," Blood 121(7):1165-1174 (2013).
Bridgeman et al., "The Optimal Antigen Response of Chimeric Antigen Receptors Harboring the CD3ζ Transmembrane Domain Is Dependent Upon Incorporation of the Receptor Into the Endogenous TCR/CD3 Complex," The Journal of Immunology, 184(12):6938-6949 (2010).

(Continued)

Primary Examiner — Jessica H Roark
(74) Attorney, Agent, or Firm — MARSHALL, GERSTEIN & BORUN LLP

(57) ABSTRACT

The present invention provides a chimeric antigen receptor (CAR) which binds a target antigen having a bulky extracellular domain, wherein the CAR comprises a Fab antigen binding domain. The present invention also provides nucleic acid sequences and constructs encoding such a CAR, cells expressing such a CAR and their therapeutic uses.

16 Claims, 12 Drawing Sheets

Specification includes a Sequence Listing.

(56) References Cited

OTHER PUBLICATIONS

Hudecek et al., "Receptor Affinity and Extracellular Domain Modifications Affect Tumor Recognition by ROR1-specific Chimeric Antigen Receptor T Cells," Clinical Cancer Research, 19(12):3153-3164 (2013).
Ma et al., "Anti-Prostate Specific Membrane Antigen Designer T Cells for Prostate Cancer Therapy", The Prostate, 61:12-25 (2004).
Thistlethwaite et al., "The Clinical Efficacy of First-Generation Carcinoembryonic Antigen (CEACAM5)-Specific CAR T Cells is Limited by Poor Persistence and Transient Pre-Conditioning-Dependent Respiratory Toxicity," Cancer Immunology Immunotherapy, 66(11):1425-1436 (2017).
Wei et al., "PSCA and MUC1 in Non-Small-Cell Lung Cancer as Targets of Chimeric Antigen Receptor T Cells", Oncoimmunology, 6:e1284722, 10 Pages (2017).
Bielamowicz et al., "Trivalent CAR T cells overcome interpatient antigenic variability in glioblastoma," Neuro-Oncology 20(4):506-518 (2018).
Donnelly et al., "The 'cleavage' activities of foot-and-mouth disease virus 2A site-directed mutants and naturally occurring '2A-like' sequences," J. Gen. Virol. 82:1027-1041 (2001).
Duan et al., "An Antibody Fab Fragment-based Chimeric Antigen Receptor Could Efficiently Eliminate Human Thyroid Cancer Cells," Journal of Cancer 10(8):1890-1895 (2019).
Fousek et al., "Trivalent CAR T cells mitigate CD19-negative relapse and improve tumor control in primary pre-B cell acute lymphoblastic leukemia (B-ALL)," Proceedings of the AACR Special Conference on Tumor Immunology and Immunotherapy 6(9 Suppl), Abstract, 2 pages (2017).
Fry et al., "CD22-CAR T Cells Induce Remissions in CD19-CAR Naive and Resistant B-ALL," Nat Med. 24(1):20-28 (2018).
International Search Report and Written Opinion from Application No. PCT/GB2019/051330 dated Aug. 13, 2019.
Munter et al., "Nanobody Based Dual Specific CARs," Int. J. Mol. Sci. 19:403:11 pages (2018).
Sadelain et al., "The basic principles of chimeric antigen receptor (CAR) design," Cancer Discov. 3(4):388-398 (2013).

* cited by examiner

CHIMERIC ANTIGEN RECEPTOR

CROSS-REFERENCE TO RELATED APPLICATIONS

This is a U.S. National Phase of International Application No. PCT/GB2019/051330, filed May 15, 2019, which claims priority to Great Britain Application No. 1807866.7, filed May 15, 2018 and Great Britain Application No. 1809773.3, filed Jun. 14, 2018.

FIELD OF THE INVENTION

The present invention relates to a chimeric antigen receptor (CAR). In particular, it relates to a CAR having a Fab-like antigen binding domain.

BACKGROUND TO THE INVENTION

Chimeric antigen receptors (CARs) A number of immunotherapeutic agents have been described for use in cancer treatment, including therapeutic monoclonal antibodies (mAbs), bi-specific T-cell engagers and chimeric antigen receptors (CARs).

Chimeric antigen receptors are proteins which graft the specificity of a monoclonal antibody (mAb) to the effector function of a T-cell. Their usual form is that of a type I transmembrane domain protein with an antigen recognizing amino terminus (binder), and a transmembrane domain connected to an endodomain which transmits T-cell activation signals.

The most common form of these molecules are fusions of single-chain variable fragments (scFv) derived from monoclonal antibodies, which recognize a target antigen, fused via a trans-membrane domain to a signalling endodomain. Such molecules result in activation of the T-cell in response to recognition by the scFv of its target. When T cells express such a CAR, they recognize and kill target cells that express the target antigen. CARs have been developed against various tumour-associated antigens and many are currently undergoing clinical trials.

Although CAR-T cell-mediated treatment have shown success towards compact target antigens such as CD19 or GD2, chimeric antigen receptors often to fail to signal in response to antigens with bulky extracellular domains.

An optimum synaptic distance is required for efficient triggering of downstream signalling after antigen encounter. Upon T cell encounter with an antigen presenting cell (via TCR interaction with peptide MHC), proteins at the interface segregate passively based on size. Phosphatases such as CD45 and CD148, which have large ectodomains, are excluded from regions of close contact between the T cell and APC (see FIG. 1). The synapse formed through interaction of peptide MHC and TCR is optimal for occlusion of CD45. In the case of CAR-T cells targeting smaller antigens such as CD19, there is no barrier to synapse formation and such antigens can be targeted efficiently at multiple epitopes. Large proteins such as CD22 pose a unique problem, as illustrated in FIG. 2. Targeting a membrane distal epitope on such proteins is likely to provide a suboptimal synapse length allowing phosphatases to enter the synapse and inhibit tyrosine phosphorylation. Targeting membrane proximal regions may improve synapse formation, however steric occlusion of the epitope is likely to lead to suboptimal ligation of the target allowing the presence of phosphatases within the synapse, dampening tyrosine phosphorylation, kinase activity and thus CAR signaling.

There is therefore a need for alternative CAR T-cell approaches, capable of killing target cells expressing a large or bulky target antigen.

SUMMARY OF ASPECTS OF THE INVENTION

Figure 1:
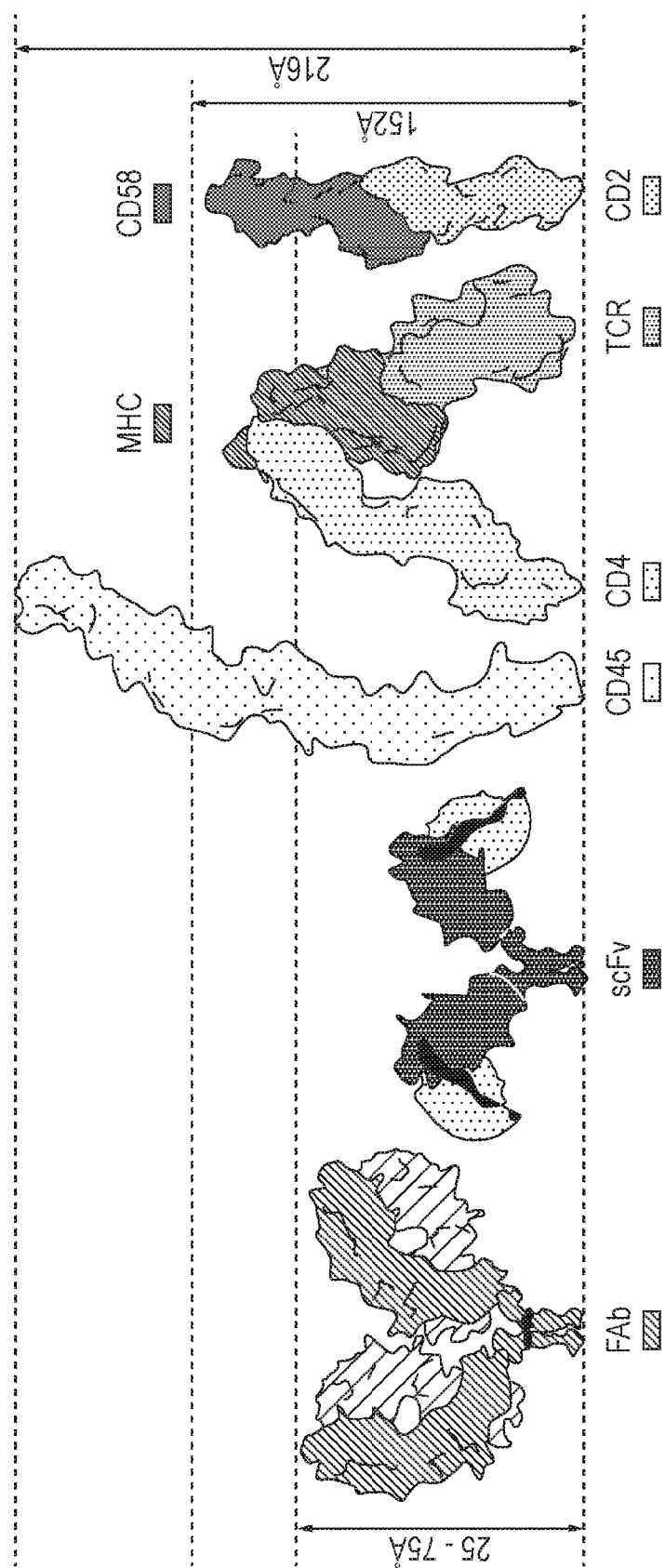
FIG. 1—Schematic diagram illustrating the relative sizes of the extracellular domains of a Fab CAR (Fab), a classical CAR having an scFv antigen binding domain (scFv), the phosphatase CD45, a CD4/TCR/MHC complex and a CD2:CD58 complex. When a T cell interacts with a tumour cell, either via a TCR:MHC interaction or a CAR:target antigen interaction, an immunological synapse is formed and phosphatases such as CD45 and CD148 are excluded.
Figure 2:
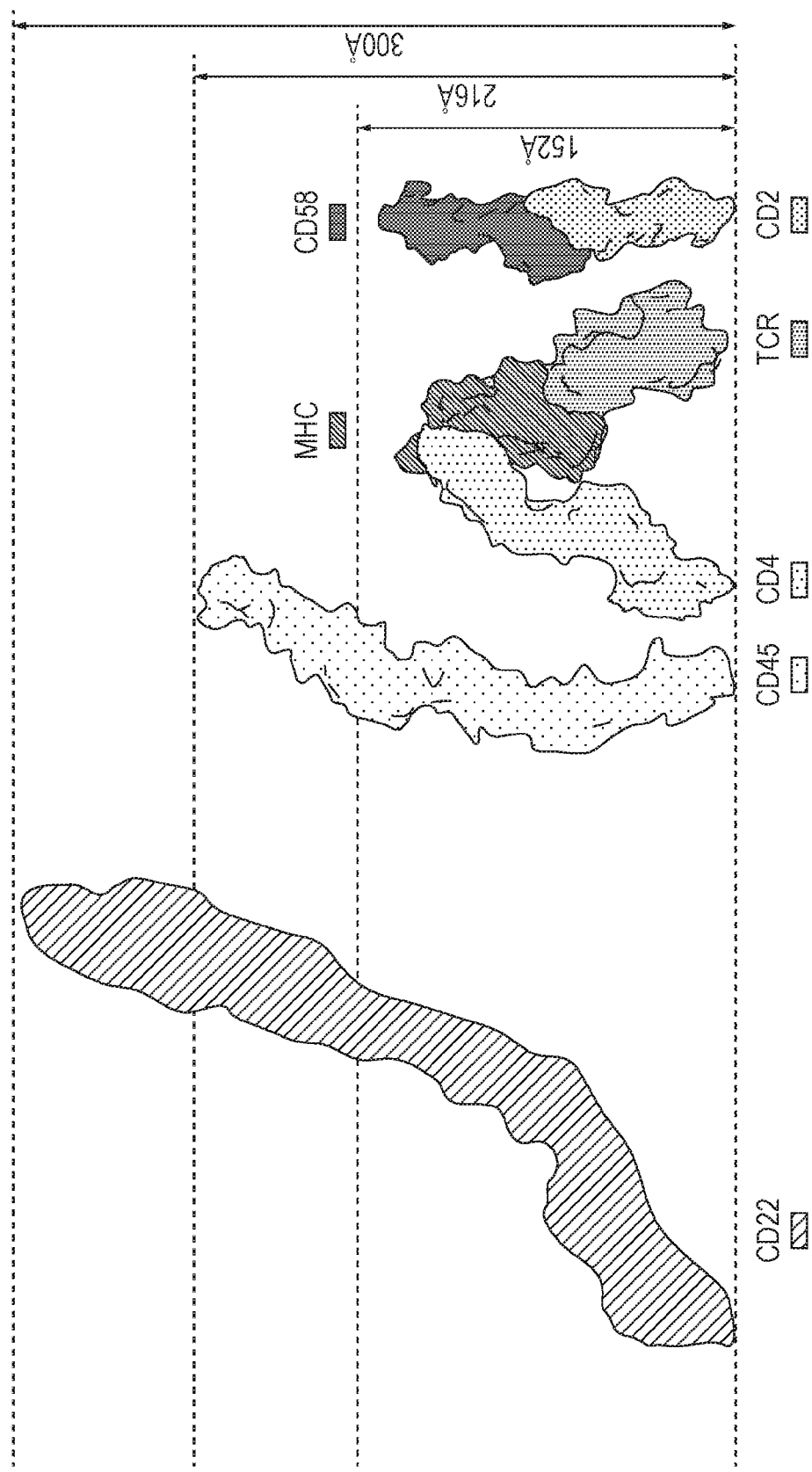
FIG. 2—Schematic diagram illustrating the relative sizes of the extracellular domains of CD22, CD45, a CD4/TCR/MHC complex and a CD2:CD58 complex. CD22 has a very large, bulky extracellular domain. This makes it a difficult target for a CAR T-cell as the combined length of the CAR extracellular domain and the CD22 extracellular domain is too long for an optimal T-cell;Target cell synapse, meaning that phosphatases such as CD45 and CD148 are not efficiently excluded.
Figure 3:
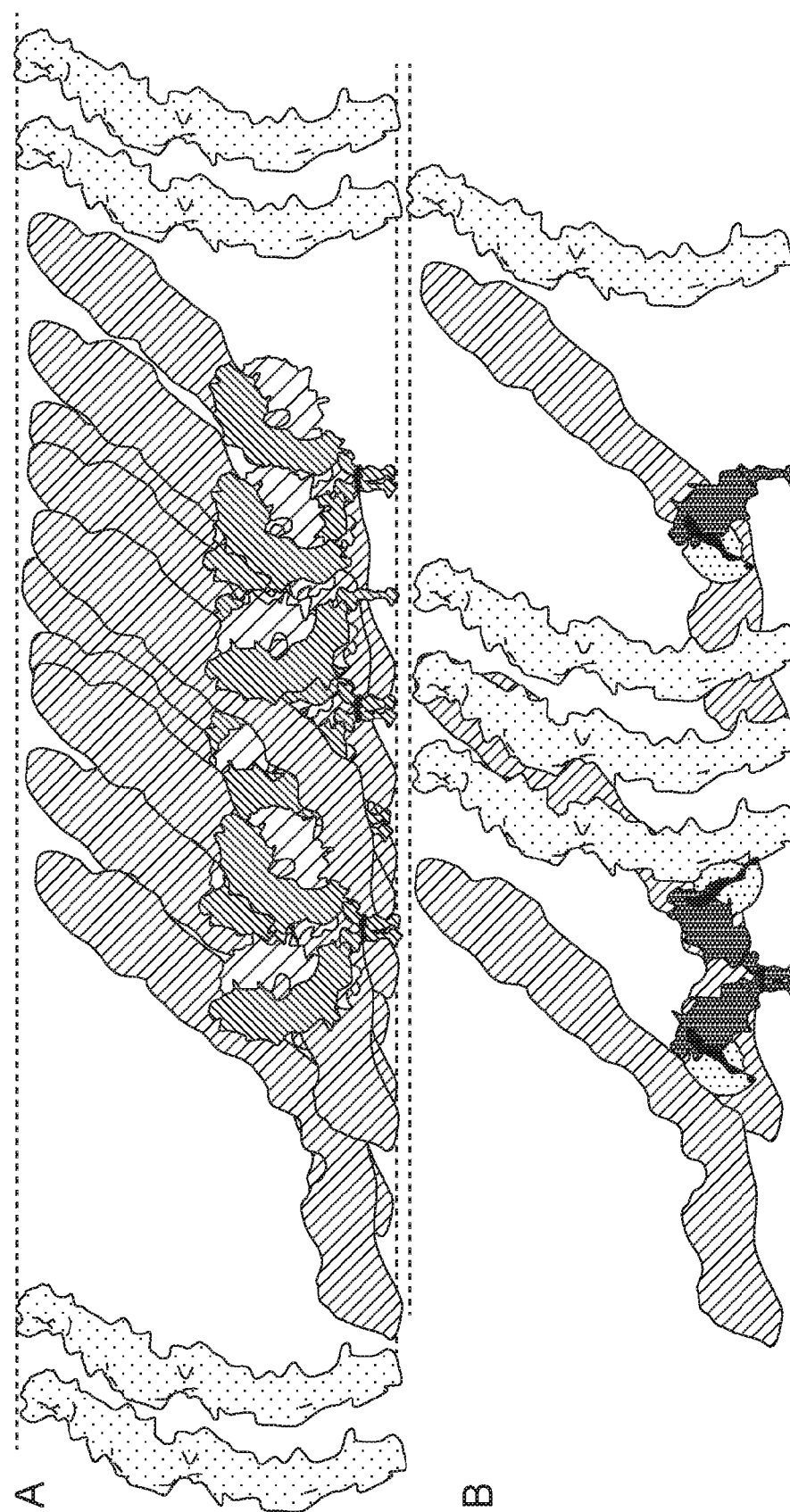
FIG. 3—Schematic diagram illustrating the T-cell:target cell synapse for (A) a FabCAR targeting CD22, and b) a classical scFv CAR targeting CD22. Surprisingly, although the extracellular domain is longer and more bulky than an scFv CAR extracellular domain and therefore might be predicted to compound the issues related to the target antigen having a large and bulky extracellular domain, the FabCAR results in better CAR-mediated signalling upon target cell encounter, and more efficient killing of target cells.

The present inventors have found that it is possible to improve CAR-mediated targeting of bulky antigens and the efficiency of CAR-mediated killing of target cells expressing bulky target antigens, using a CAR having a Fab binding domain as opposed to an scFv binding domain.

Thus, in a first aspect the present invention provides a chimeric antigen receptor (CAR) which binds a target antigen having a bulky extracellular domain, wherein the CAR comprises a Fab antigen binding domain.

The target antigen may have an extracellular domain of at least about 150 Å.

The target antigen may have an extracellular domain of at least about 400 amino acids.

The target antigen may be selected from the following group: CD22, CD21, CEACAM5, MUC1 or FcRL5. In particular, the target antigen may be CD22.

The antigen-binding domain may comprise;
a) a heavy chain variable region (VH) having complementarity determining regions (CDRs) with the following sequences:

```
CDR1
                                  (SEQ ID No. 93)
NFAMA

CDR2
                                  (SEQ ID No. 94)
SISTGGGNTYYRDSVKG

CDR3
                                  (SEQ ID No. 95)
QRNYYDGSYDYEGYTMDA;
``` and
b) a light chain variable region (VL) having complementarity determining regions (CDRs) with the following sequences:

```
CDR1
                                  (SEQ ID No. 96)
RSSQDIGNYLT

CDR2
                                  (SEQ ID No. 97)
GAIKLED
```

```
CDR3
                                  (SEQ ID No. 98)
LQSIQYP.
```

The antigen-binding domain may comprise:
a) a heavy chain variable region (VH) having complementarity determining regions (CDRs) with the following sequences:

```
CDR1
                                  (SEQ ID No. 101)
TSGMGVG

CDR2
                                  (SEQ ID No. 102)
NIWWDDDKNYNPSLKN

CDR3
                                  (SEQ ID No. 103)
IAHYFDGYYYVMDV;
``` and
b) a light chain variable region (VL) having complementarity determining regions (CDRs) with the following sequences:

```
CDR1
                                  (SEQ ID No. 104)
LASGGISNDLA

CDR2
                                  (SEQ ID No. 105)
AASRLQD

CDR3
                                  (SEQ ID No. 106)
QQSYKYPY
```

The CAR may comprise a VH domain having the sequence shown as SEQ ID No. 65; and a VL domain having the sequence shown as SEQ ID No. 66.

The CAR may comprise a VH domain having the sequence shown as SEQ ID No. 99; and a VL domain having the sequence shown as SEQ ID No. 100.

In a second aspect, there is provided a nucleic acid sequence which encodes a CAR according to the first aspect of the invention.

The nucleic acid sequence may have the following general structure:

VH-CH-spacer-TM-endo-coexpr-VL-CL in which:

VH is a nucleic acid sequence encoding a heavy chain variable domain of a first polypeptide;

CH is a nucleic acid sequence encoding a heavy chain constant domain of the first polypeptide;

spacer is a nucleic acid sequence encoding a spacer of the first polypeptide;

TM is a nucleic acid sequence encoding a transmembrane region of the first polypeptide;

endo is a nucleic acid sequence encoding an endodomain of the first polypeptide;

VL is a nucleic acid sequence encoding a light chain variable domain of a second polypeptide;

CL is a nucleic acid sequence encoding a light chain constant domain of the second polypeptide; and coexpr is a nucleic acid sequence enabling the co-expression of the first and second polypeptides.

In a third aspect, there is provided a nucleic acid construct which comprises a first nucleic acid sequence according to the second aspect of the invention, and a second nucleic acid sequence encoding a second chimeric antigen receptor which has a domain antibody (dAb) or scFv antigen binding domain.

In particular, there is provided a nucleic acid construct which comprises a first nucleic acid sequence according to the second aspect of the invention; a second nucleic acid sequence encoding a second chimeric antigen receptor which has a domain antibody (dAb) antigen binding domain; and a third nucleic acid sequence encoding a third CAR which has an scFv antigen binding domain.

The first nucleic acid sequence may encode an anti-CD22 Fab CAR; the second nucleic acid sequence may encode an anti-CD79 dAb CAR; and the third nucleic acid sequence may encode an anti-CD19 scFv CAR.

In a fourth aspect, there is provided a vector which comprises a nucleic acid sequence according to the second aspect of the invention or a nucleic acid construct according to the third aspect of the invention.

In a fifth aspect, there is provided a cell which expresses a CAR according to the second aspect of the invention.

In particular, there is provided a cell which expresses a first CAR according to the first aspect of the invention, and a second chimeric antigen receptor which has a domain antibody (dAb) or scFv antigen binding domain.

In particular, there is provided a cell which expresses a first CAR according to the first aspect of the invention; a second CAR which has a domain antibody (dAb) antigen binding domain; and a third CAR which has an scFv antigen binding domain.

The first CAR may be an anti-CD22 Fab CAR; the second CAR may be an anti-CD79 dAb CAR; and the third CAR may be an anti-CD19 scFv CAR.

In a sixth aspect, there is provided a method for making a cell according to the fifth aspect of the invention, which comprises the step of introducing a nucleic acid sequence according to the second aspect of the invention; a nucleic acid construct according to the third aspect of the invention; or a vector according to the fourth aspect of the invention into a cell ex vivo.

In a seventh aspect, there is provided a pharmaceutical composition which comprises a plurality of cells according the fifth aspect of the invention, together with a pharmaceutically acceptable carrier, diluent or excipient.

In an eighth aspect, there is provided a method for treating cancer which comprises the step of administering a pharmaceutical composition according to the seventh aspect of the invention to a subject.

The cancer may, for example, be a B-cell lymphoma or leukemia.

In a ninth aspect, there is provided a pharmaceutical composition according to the seventh aspect of the invention for use in treating cancer.

In a tenth aspect, there is provided the use of a cell according to the fifth aspect of the invention in the manufacture of a pharmaceutical composition for treating cancer.

The present invention provides chimeric antigen receptors which show improved

CAR-mediated signalling and target cell killing when targeting antigens with bulky extracellular domains. Such antigens are difficult to target with a classical CAR as they form sub-optimal T-cell:target cell synapses.

To capacity to target such antigens opens up whole new possibilities for cancer treatment. Many potentially useful cancer target antigens have bulky extracellular domains, for example, CD22, CD21, CEACAM5, MUC1 or FcRL5. The present invention provides improved constructs for targeting these antigens, enabling them to be used as single targets and, importantly, to be included in strategies for targeting multiple antigens in order to increase CAR-T cell efficacy and safety.

DETAILED DESCRIPTION

Chimeric Antigen Receptors

The present invention relates to a chimeric antigen receptor with a Fab antigen-binding domain.

A classical chimeric antigen receptor (CAR) is a chimeric type I trans-membrane protein which connects an extracellular antigen-recognizing domain (binder) to an intracellular signalling domain (endodomain). The binder is typically a single-chain variable fragment (scFv) derived from a monoclonal antibody (mAb), but it can be based on other formats which comprise an antibody-like antigen binding site. A spacer domain is usually necessary to isolate the binder from the membrane and to allow it a suitable orientation. A common spacer domain used is the Fc of IgG1. More compact spacers can suffice e.g. the stalk from CD8a and even just the IgG1 hinge alone, depending on the antigen. A trans-membrane domain anchors the protein in the cell membrane and connects the spacer to the endodomain.

Early CAR designs had endodomains derived from the intracellular parts of either the γ chain of the FcεR1 or CD3ζ. Consequently, these first generation receptors transmitted immunological signal 1, which was sufficient to trigger T-cell killing of cognate target cells but failed to fully activate the T-cell to proliferate and survive. To overcome this limitation, compound endodomains have been constructed: fusion of the intracellular part of a T-cell co-stimulatory molecule to that of CD3 ζ results in second generation receptors which can transmit an activating and co-stimulatory signal simultaneously after antigen recognition. The co-stimulatory domain most commonly used is that of CD28. This supplies the most potent co-stimulatory signal—namely immunological signal 2, which triggers T-cell proliferation. Some receptors have also been described which include TNF receptor family endodomains, such as the closely related OX40 and 41BB which transmit survival signals. Even more potent third generation CARs have now been described which have endodomains capable of transmitting activation, proliferation and survival signals.

When the CAR binds the target-antigen, this results in the transmission of an activating signal to the T-cell it is expressed on. Thus the CAR directs the specificity and cytotoxicity of the T cell towards tumour cells expressing the targeted antigen.

CARs typically therefore comprise: (i) an antigen-binding domain; (ii) a spacer; (iii) a transmembrane domain; and (iii) an intracellular domain which comprises or associates with a signalling domain.

A CAR may have the general structure:

Antigen binding domain-spacer domain-transmembrane domain-intracellular signaling domain (endodomain).

Antigen Binding Domain

The antigen binding domain is the portion of the chimeric receptor which recognizes antigen. In a classical CAR, the antigen-binding domain comprises: a single-chain variable fragment (scFv) derived from a monoclonal antibody (see FIG. 6c). CARs have also been produced with domain antibody (dAb) or VHH antigen binding domains (see FIG. 6b).

Figure 6:
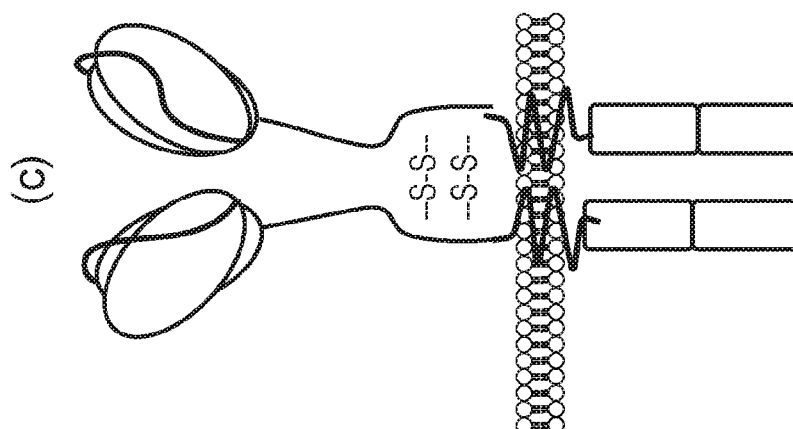
FIG. 6—Different binding domain formats of chimeric antigen receptors (a) Fab CAR format; (b) dAb CAR format; (c) scFv CAR format FIG. 7—CAR OR gate targeting CD19, CD22 and CD79 using different format CARs (a) A tricistronic cassette can be generated be separating the coding sequences for the two receptors using two FMD-2A sequences; (b) OR gate combining three different formats: scFv-CAR for CD19, Fab CAR for CD22 and dAb CAR for CD79
Figure 6:
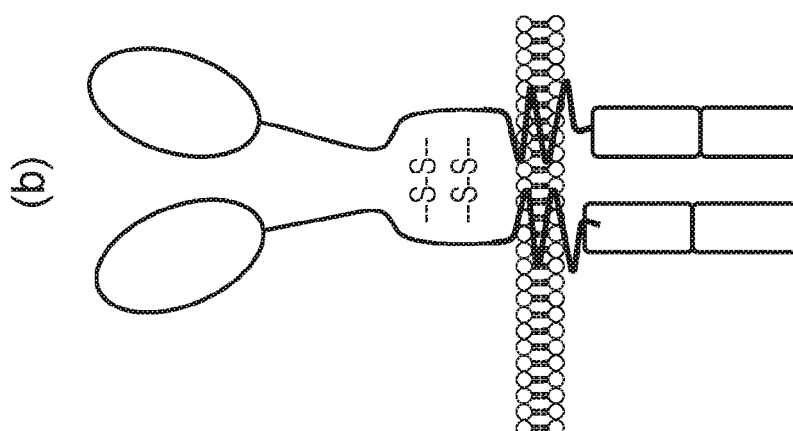
Figure 6:
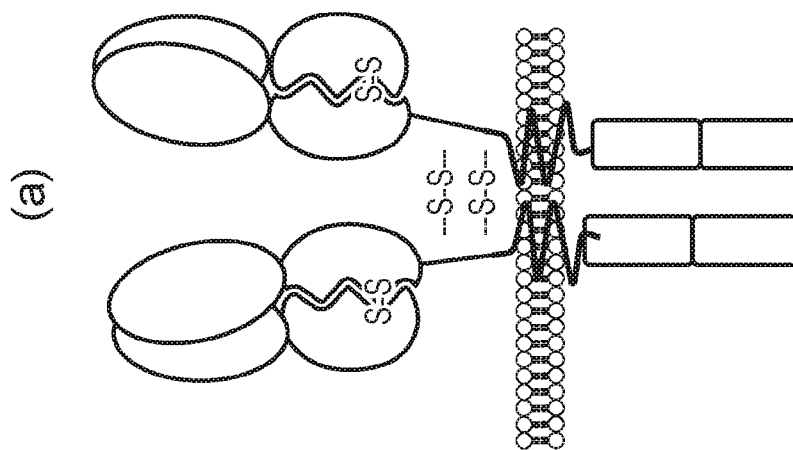

In the chimeric antigen receptors of the present invention, the antigen binding comprises a Fab fragment of, for example, a monoclonal antibody (see FIG. 6a). A FabCAR comprises two chains: one having an antibody-like light chain variable region (VL) and constant region (CL); and one having a heavy chain variable region (VH) and constant region (CH). One chain also comprises a transmembrane domain and an intracellular signalling domain. Association between the CL and CH causes assembly of the receptor.

The two chains of a Fab CAR may have the general structure:

VH-CH-spacer-transmembrane domain-intracellular signalling domain; and
VL-CL
or
VL-CL-spacer-transmembrane domain-intracellular signalling domain; and
VH-CH For the Fab-type chimeric receptors described herein, the antigen binding domain is made up of a VH from one polypeptide chain and a VL from another polypeptide chain.

The polypeptide chains may comprise a linker between the VH/VL domain and the CH/CL domains. The linker may be flexible and serve to spatially separate the VH/VL domain from the CH/CL domain.

Flexible linkers may be composed of small, non-polar residues such as glycine, threonine and serine. The linker may comprise one or more repeats of a glycine-serine linker, such as a $(Gly_4Ser)_n$ linker, where n is the number of repeats. The or each linker may be less than 50, 40, 30, 20 or 10 amino acids in length.

Constant Region Domains

There are two types of light chain in humans: kappa (κ) chain and lambda (λ) chain. The lambda class has 4 sub-types: $\lambda_1$, $\lambda_2$, $\lambda_3$ and $\lambda_4$. The light chain constant region of a Fab-type chimeric receptor may be derived from any of these light chain types.

The light chain constant domain of a chimeric receptor of the present invention may have the sequence shown as SEQ ID NO. 1 which is a kappa chain constant domain.

```
                                           SEQ ID No. 1
TVAAPSVFIFPPSDEQLKSGTASVVCLLNNFYPREAKVQWKVDN

ALQSGNSQESVTEQDSKDSTYSLSSTLTLSKADYEKHKVYACEV

THQGLSSPVTKSFNRGEC
```

There are five types of mammalian immunoglobulin heavy chain: γ, δ, α, μ and ε which define the classes of immunoglobulin IgG, IgD, IgA, IgM and IgE respectively. Heavy chains γ, δ and α have a constant domain composed of three tandem Ig domain and have a hinge for added flexibility. Heavy chains μ and ε are composed of four domains.

The CH domain of a Fab-type chimeric receptor of the present invention may comprise the sequence shown as SEQ ID No. 2 which is from a γ immunoglobulin heavy chain.

```
                                           SEQ ID No. 2
STKGPSVFPLAPSSKSTSGGTAALGCLVKDYFPEPVTVSWNSGA

LTSGVHTFPAVLQSSGLYSLSSVVTVPSSSLGTQTYICNVNHKP

SNTKVDKRV
```

Spacer

Classical CARs comprise a spacer sequence to connect the antigen-binding domain with the transmembrane domain and spatially separate the antigen-binding domain from the endodomain. A flexible spacer allows the antigen-binding domain to orient in different directions to facilitate binding.

In a FabCAR (FIG. 6A), as in a classical chimeric antigen receptor (FIG. 6C) and a dAb CAR (FIG. 6B), the spacer may cause two of the polypeptide chains to dimerise. Two of the polypeptide chains may, for example, comprise one or more suitable cysteine residues to form di-sulphide bridge(s). The hinge from IgG1 is suitable in this regard. A spacer based on an IgG1 hinge may have the sequence shown as SEQ ID. No. 3

```
(human IgG1 hinge):
                                           SEQ ID No. 3
AEPKSPDKTHTCPPCPKDPK
```

Alternatively, a hinge spacer may have the sequence shown as SEQ ID No. 4

```
(hinge spacer)
                                           SEQ ID No. 4
EPKSCDKTHTCPPCP
```

In the FabCAR of the invention, the two polypeptides of a dimeric FabCAR, as illustrated in FIG. 6A are identical. They have the same antigen binding domains derived from the same antibody, and they bind the same epitope on the same target antigen. The first and second polypeptides in the dimer are simply duplicate copies of a polypeptide encoded from the same transcript.

Transmembrane Domain

The transmembrane domain is the portion of the chimeric receptor which spans the membrane. The transmembrane domain may be any protein structure which is thermodynamically stable in a membrane. This is typically an alpha helix comprising of several hydrophobic residues. The transmembrane domain of any transmembrane protein can be used to supply the transmembrane portion of the chimeric receptor. The presence and span of a transmembrane domain of a protein can be determined by those skilled in the art using the TMHMM algorithm (http://www.cbs.dtu.dk/services/TMHMM-2.0/). Alternatively, an artificially designed TM domain may be used.

Endodomain

The endodomain is the signal-transmission portion of the chimeric receptor. It may be part of or associate with the intracellular domain of the chimeric receptor. After antigen recognition, receptors cluster, native CD45 and CD148 are excluded from the synapse and a signal is transmitted to the cell. The most commonly used endodomain component is that of CD3-zeta which contains 3 ITAMs. This transmits an activation signal to the T cell after antigen is bound. CD3-zeta may not provide a fully competent activation signal and additional co-stimulatory signalling may be needed. Co-stimulatory signals promote T-cell proliferation and survival. There are two main types of co-stimulatory signals: those that belong the Ig family (CD28, ICOS) and the TNF family (OX40, 41BB, CD27, GITR etc). For example, chimeric CD28 and OX40 can be used with CD3-Zeta to transmit a proliferative/survival signal, or all three can be used together.

The endodomain may comprise:

(i) an ITAM-containing endodomain, such as the endodomain from CD3 zeta; and/or (ii) a co-stimulatory domain, such as the endodomain from CD28 or ICOS; and/or (iii) a domain which transmits a survival signal, for example a TNF receptor family endodomain such as OX-40, 4-1BB, CD27 or GITR.

A number of systems have been described in which the antigen recognition portion is on a separate molecule from the signal transmission portion, such as those described in WO015/150771; WO2016/124930 and WO2016/030691. The chimeric receptor of the present invention may therefore comprise an antigen-binding component comprising an antigen-binding domain and a transmembrane domain; which is capable of interacting with a separate intracellular signalling component comprising a signalling domain. The vector of the invention may express a chimeric receptor signalling system comprising such an antigen-binding component and intracellular signalling component.

The chimeric receptor may comprise a signal peptide so that when it is expressed inside a cell, the nascent protein is directed to the endoplasmic reticulum and subsequently to the cell surface, where it is expressed. The signal peptide may be at the amino terminus of the molecule.

TARGET ANTIGEN

A 'target antigen' is an entity which is specifically recognised and bound by the antigen-binding domains of a chimeric receptor of the invention.

The target antigen may be an antigen present on a cancer cell, for example a tumour-associated antigen.

The target antigen may have a relatively long and/or bulky extracellular domain. The extracellular domain of CD45 is 216Å in size. Depending on the spacer used typically the antigen binding domain of a classical CAR will measure in the range of 25-75 Å, as such, antigens larger than 150A are difficult to target due to the poor synapse formation, leading to the presence of phosphatases within said synapse.

The target antigen may have an extracellular domain which is greater than about 150 Å, for example the target antigen may have an extracellular domain which is 150-400 Å, 200-350 Å or 250-310 Å in size.

There is a correlation between the size of the molecule and the amino acid length of the extracellular domain of target antigens. Examples of the size of the extracellular domain and the number of amino acids is shown in the table below both for antigens with compact extracellular domains (EpCAM, CD19) and antigens with bulky extracellular domains (CEACAM5, CD22).

| Protein | Extracellular domain size | Amino acids |
| --- | --- | --- |
| EpCAM | 48 Å | 242 |
| CD19 | 63 Å | 272 |
| CEACAM5 | 280 Å | 651 |
| CD22 | 306 Å | 668 |

The target antigen may have an extracellular domain which is greater than about 400 amino acids in length, for example the target antigen may have an extracellular domain which is 400-1000, 500-900, 600-800 or 600-700 amino acids in length.

The extracellular domain of CD22 has seven IgG-like domains in its extracellular domain. The target antigen of the chimeric receptor of the invention may have a length equivalent to at least 4, 5, 6 or 7 Ig-like domains. The extracellular domain of CD21 has 21 short consensus repeats (SCR) of about 60 amino acids each. The target antigen of the chimeric receptor of the invention may have a length equivalent to at least 15, 17, 19 or 21 CSRs.

The target antigen may have an extracellular domain which is longer than the optimal intracellular distance between a T-cell and a target cell at a T-cell:target cell synapse. The target cell may have an extracellular domain which is at least 40, 50, 60 or 70 nM The target antigen may be CD22, CD21, CEACAM5, MUC1 or FCRL5

CD22

CD22 has seven extracellular IgG-like domains, which are commonly identified as Ig domain 1 to Ig domain 7, with Ig domain 7 being most proximal to the B cell membrane and Ig domain 1 being the most distal from the Ig cell membrane.

The positions of the Ig domains in terms of the amino acid sequence of CD22 (http://www.uniprot.org/uniprot/P20273) are summarised in the following table:

| Ig domain | Amino acids |
| --- | --- |
| 7 | 20-138 |
| 6 | 143-235 |
| 5 | 242-326 |
| 4 | 331-416 |
| 3 | 419-500 |
| 2 | 505-582 |
| 1 | 593-676 |

Examples of anti-CD22 CARs with antigen-binding domains derived from m971, HA22 and BL22 scFvs are described by Haso et al. (Blood; 2013; 121(7)). The antibodies HA22 and BL22 bind to an epitope on Ig domain 5 of CD22.

Other anti-CD22 antibodies are known, such as the mouse anti-human CD22 antibodies 1D9-3, 3B4-13, 7G6-6, 6C4-6, 4D9-15, 5H4-9, 10C1-D9, 15G7-2, 2B12-8, 2C4-4 and 3E10-7; and the humanised anti-human CD22 antibodies LT22 and Inotuzumab (G5_44). Table 1 summarises the, VH, VL and CDR sequences (in bold and underlined) and the position of the target epitope on CD22 for each antibody.

TABLE 1

| Antibody | VH | VL | Position of epitope on CD22 |
| --- | --- | --- | --- |
| 1D9-3 | EVQLVESGGGLVQPKGSLK LSCAASGFTFNTYAMHWVR QAPGKGLEWVARIRSKSSN YATYYADSVKDRFTISRDD SQSMLYLQMNNLKTEDTAM YYCVVDYLYAMDYWGQGT SVTVSS (SEQ ID No. 39) | DIVMTQSQKFMSTSVGD RVSITCKASQNVRTAVA WYQQKPGQSPKALIYLA SNRHTGVPDRFTGSGSG TDFTLTISNVQSEDLADY FCLQHWNYPFTFGSGTK LEIK (SEQ ID No. 40) | Domain 1 and 2 |

TABLE 1-continued

| Antibody | VH | VL | Position of epitope on CD22 |
|---|---|---|---|
| 3B4-13 | QVQLQQSGAELVRPGASVT LSCKASGYTFTDYEMHWVK QTPVHGLEWIGAIDPETGA TAYNQKFKGKAILTADKSSS TAYMDLRSLTSEDSAVYYC TRYDYGSSPWFAYWGQGT LVTVSA (SEQ ID No. 41) | QAVVTQESALTTSPGET VTLTCRSSAGAVTTSNY ANWVQEKPDHLFTGLIG GTNNRAPGVPARFSGSL IGDKAALTITGAQTEDEAI YFCALWNSNHWVFGGG TKLTVL (SEQ ID No. 42) | Domain 1 and 2 |
| 7G6-6 | QVQLQQPGAELVMPGASV KLSCKASGYTFTSYWMHW VKQRPGQGLEWIGEIDPSD SYTNYNQKFKGKATLTVDK SSSTAYMQLSSLTSEDSAV YYCARGYYGSSSFDYWGQ GTTLTVSS (SEQ ID No. 43) | DIVMSQSPSSLAVSVGE KVTMSCKSSQSLLYSSN QKNYLAWYQQKPGQSP KLLIYWASTRESGVPDRF TGSGSGTDFTLTISSVKA EDLAVYYCQQYYSYTFG GGTKLEIK (SEQ ID No. 44) | Domain 1 and 2 |
| 6C4-6 | QVQLKESGPGLVAPSQSLSI TCTVSGFSLTSYGVHWVRQ PPGKGLEWLVVIWSDGSTT YNSALKSRLSISKDNSKSQ VFLKMNSLQTDDTAMYYCA RHADDYGFAWFAYWGQG TLVTVSA (SEQ ID No. 45) | DIQMTQSPASLSASVGE TVTITCRASENIYSYLAW YQQKQGKSPQLLVYNAK TLAEGVPSRFSGSGSGT QFSLKINSLQPEDFGSYY CQHHYGTPPTFGGGTKL EIK (SEQ ID No. 46) | Domain 3 |
| 4D9-12 | EFQLQQSGPELVKPGASVK ISCKASGYSFTDYNMNWVK QSNGKSLEWIGVINPNYGT TSYNQKFKGKATLTVDQSS STAYMQLNSLTSEDSAVYY CARSSTTVVDWYFDVWGT GTTVTVSS (SEQ ID No. 47) | DIQMTQSPSSLSASLGE RVSLTCRASQEISGYLS WLQQKPDGTIKRLIYAAS TLDSGVPKRFSGSRSGS DYSLTISSLESEDFADYY CLQYASYPFTFGSGTKL EIK (SEQ ID No. 48) | Domain 4 |
| 5H4-9 | QVQVQQPGAELVRPGTSV KLSCKASGYTFTRYWMYW VKQRPGQGLEWIGVIDPSD NFTYYNQKFKGKATLTVDT SSSTAYMQLSSLTSEDSAV YYCARGYGSSYVGYWGQG TTLTVSS (SEQ ID No. 49) | DVVMTQTPLSLPVSLGD QASISCRSSQSLVHSNG NTYLHWYLQKPGQSPKL LIYKVSNRFSGVPDRFSG SGSGTDFTLKISRVEAED LGVYFCSQSTHVPPWTF GGGTKLEIK (SEQ ID No. 50) | Domain 4 |
| 10C1-D9 | QVTLKESGPGILQSSQTLSL TCSFSGFSLTSDMGVSWI RQPSGKGLEWLAHIYWDD DKRYNPSLKSRLTISKDASR NQVFLKIATVDTADTATYYC ARSPWIYYGHYWCFDVWG TGTTVTVSS (SEQ ID No. 51) | DIQMTQTTSSLSASLGDR VTISCRASQDISNYLNWY QQKPDGTVKLLIYYTSRL HSGVPSRFSGSGSGTDY SLTISNLEQEDIATYFCQ QGNTLPFTFGSGTKLEIK (SEQ ID No. 52) | Domain 4 |
| 15G7-2 | QVQLQQSGAELVKPGASVK LSCKASGYTFTEYTIHWVK QRSGQGLEWIGWFYPGSG SIKYNEKFKDKATLTADKSS STVYMELSRLTSEDSAVYF CARHGDGYYLPPYYFDYW GQGTTLTVSS (SEQ ID No. 53) | QIVLTQSPAIMSASPGEK VTMTCSASSSVSYMYW YQQKPGSSPRLLIYDTSN LASGVPVRFSGSGSGTS YSLTISRMEAEDAATYYC QQWSSYPLTFGAGTKLE LK (SEQ ID No. 54) | Domain 4 |
| 2B12-8 | QVQLQQSGAELARPGASVK LSCKASGYIFTSYGISWVKQ RTGQGLEWIGEIYPRSGNT YYNEKFKGKATLTADKSSS TAYMELRSLTSEDSAVYFC ARPIYYGSREGFDYWGQGT TLTVSS (SEQ ID No. 55) | DIVLTQSPATLSVTPGDS VSLSCRASQSISTNLHW YQQKSHASPRLLIKYASQ SVSGIPSRFSGSGSGTD FTLSINSVETEDFGIFFCQ QSYSWPYTFGGGTKLEI K (SEQ ID No. 56) | Domain 4 |

TABLE 1-continued

| Antibody | VH | VL | Position of epitope on CD22 |
|---|---|---|---|
| 2C4-4 | QVQLQQPGAELVMPGASV KLSCKASGYTFTSYWMHW VKQRPGQGLEWIGEIDPSD SYTNYNQKFKGKSTLTVDK SSSTAYIQLSSLTSEDSAVY YCARWASYRGYAMDYWG QGTSVTVSS (SEQ ID No. 57) | DVLMTQTPLSLPVSLGD QASISCRSSQSIVHSNGN TYLEWYLQKPGQSPKLLI YKVSNRFSGVPDRFSGS ESGTDFTLKISRVEAEDL GVYYCFQGSHVPWTFG GGTKLEIK (SEQ ID No. 58) | Domain 5-7 |
| 3E10-7 | EFQLQQSGPELVKPGASVK ISCKASGYSFTDYNMNWVK QSNGKSLEWIGVINPNYGT TSYNQRFKGKATLTVDQSS STAYMQLNSLTSEDSAVYY CARSGLRYWYFDVWGTGT TVTVSS (SEQ ID No. 59) | DIQMTQSPSSLSASLGE RVSLTCRASQEISGYLS WLQQKPDGTIKRLIYAAS TLDSGVPKRFSGSRSGS DYSLTISSLESEDFADYY CLQYASYPFTFGSGTKL EIK (SEQ ID No. 60) | Domain 5-7 |
| LT22 | EVQLVESGAEVKKPGSSVK VSCKASGYTFTNYWINWVR QAPGQGLEWMGNIYPSDS FTNYNQKFKDRVTITADKST STVYLELRNLRSDDTAVYY CTRDTQERSWYFDVWGQG TLVTVSS (SEQ ID No. 61) | DIVMTQSPATLSVSPGER ATLSCRSSQSLVHSNGN TYLHWVYQQKPGQAPRLL IYKVSNRFSGVPARFSG SGSGAEFTLTISSLQSED FAVYYCSQSTHVPWTFG QGTRLEIKR (SEQ ID No. 62) | Domain 5 |
| Inotuzumab G5_44 | EVQLVQSGAEVKKPGASVK VSCKASGYRFTNYWIHWVR QAPGQGLEWIGGINPGNNY ATYRRKFQGRVTMTADTST STVYMELSSLRSEDTAVYY CTREGYGNYGAWFAYWG QGTLVTVSS (SEQ ID No. 63) | DVQVTQSPSSLSASVGD RVTITCRSSQSLANSYG NTFLSWYLHKPGKAPQL LIYGISNRFSGVPDRFSG SGSGTDFTLTISSLQPED FATYYCLQGTHQPYTFG QGTKVEIKR (SEQ ID No. 64) | Domain 7 |
| 9A8-1 | EVQLVESGGGLVQPGRSLK LSCAASGFTFSNFAMAWVR QPPTKGLEWVASISTGGGN TYYRDSVKGRFTISRDDAK NTQYLQMDSLRSEDTATYY CARQRNYYDGSYDYEGYT MDAWGQGTSVTVSS (SEQ ID No. 65) | DIQMTQSPSSLSASLGD RVTITCRSSQDIGNYLTW FQQKVGRSPRRMIYGAI KLEDGVPSRFSGSRSGS DYSLTISSLESEDVADYQ CLQSIQYPFTFGSGTKLE IK (SEQ ID No. 66) | Domains 1 and 2 |
| 1G3-4 | QVTLKESGPGILQPSQTLSL TCTFSGFSLSTSGMGVGWI RQPSGKGLEWLTNIWWDD DKNYNPSLKNRLTISKDTSI NQAFLKITNVDTADTATYYC ARIAHYFDGYYYVMDVWG QGTSVTVSS (SEQ ID No. 99) | DIQMTQSPASLSASLGET VSIECLASGGISNDLAWY QQKSGKSPQLLIYAASR LQDGVPSRFSGSGSGTR YSLKISGMQSEDEADYF CQQSYKYPYTFGGGTKL ELK (SEQ ID No. 100) | Domain 4 |

An antigen binding domain of a FabCAR which binds to CD22 may comprise the VH and/or VL sequence from any of the CD22 antibodies listed in table 1, or a variant thereof which has at least 70, 80, 90 or 90% sequence identity, which variant retains the capacity to bind CD22.

CD21

CD21, also known as CR2 is a protein expressed on mature B cells and follicular dendritic cells which is involved in the complement system. On mature B cells, CD21 forms the B cell coreceptor complex with CD19 and CD81. When membrane IgM binds to the antigen, CD21 binds to antigens through the attached C3d.

Mature CD21 is 1,408 amino acids that includes 21 short consensus repeats (SCR) of about 60 amino acids each, plus transmembrane and cytoplasmic regions.

Commercially available monoclonal antibodies against CD21 are known, such as MAB4909 (MDS Systems) and EP3093, SP186, Bu32, SP199, 1F8 and LT21 (Abcam).

CEACAM5

Carcinoembryonic antigen-related cell adhesion molecule 5 (CEACAM5) is a member of the carcinoembryonic antigen (CEA) gene family; a set of highly related glycoproteins involved in cell adhesion. CEACAM5 is produced in gastrointestinal tissue during fetal development but is also expressed by some cancers including lung, pancreatic, cervical and gastrointestinal cancers.

CEACAM5 is composed of 642 amino acids, has a molecular mass of approximately 70 kDa and has 28 potential N-linked glycosylation sites. The protein comprises an Ig variable region (IgV)-like domain, termed N, followed by six Ig constant region (IgC)-type 2-like domains, termed A1, B1, A2, B2, A3, and B3.

Commercially available monoclonal antibodies against CEACAM5 are known, such as EPR20721 (Abcam).

MUC1

Mucin 1 or MUC1 is a glycoprotein with extensive O-linked glycosylation of its extracellular domain. Mucins line the apical surface of epithelial cells in the lungs, stomach, intestines, eyes and several other organs. They protect the body from infection by pathogen binding to oligosaccharides in the extracellular domain, preventing the pathogen from reaching the cell surface. Overexpression of MUC1 is often associated with colon, breast, ovarian, lung and pancreatic cancers.

MUC1 has a core protein mass of 120-225 kDa which increases to 250-500 kDa with glycosylation. It extends 200-500 nm beyond the surface of the cell. The extracellular domain includes a 20 amino acid variable number tandem repeat (VNTR) domain, with the number of repeats varying from 20 to 120 in different individuals. The most frequent alleles contains 41 and 85 repeats. These repeats are rich in serine, threonine and proline residues which permits heavy o-glycosylation.

Commercially available monoclonal antibodies against MUC1 are known, such as EPR1203, EP1024Y, HMFG1, NCRC48, SM3, MH1 and 115D8 (Abcam).

FCRL5

Fc receptor-like protein 5 (FCRL5) is a member of the immunoglobulin receptor superfamily and the Fc-receptor like family FCRL5 is a single-pass type I membrane protein and contains 8 immunoglobulin-like C2-type domains. The mature protein is 106 kDa.

FCRL5 has a cytoplasmic tail with two inhibitory ITIM phosphorylation signaling motifs. It inhibits B cell antigen receptor signaling by recruiting SHP1 upon B cell antigen receptor co-stimulation, resulting in diminished calcium influx and protein tyrosine phosphorylation. Co-stimulation of FCRL5 and the B cell antigen receptor promotes proliferation and differentiation of naive B cells. FCRL5 is expressed on both mature B cells and plasma cells, and is induced by EBV proteins. It is overexpressed on malignant B cells of hairy cell leukemia, chronic lymphocytic leukemia, mantle cell lymphoma, and multiple myeloma patients.

Commercially available monoclonal antibodies against FCRL5 are known, such as CD307e (ThermoFisher) and REA391 (Miltenyi Biotec).

The present inventors have also generated four new anti-FCRL5 antibodies, the VH, VL and CDR sequences of which are summarised in Table 2. The CDR sequences are in bold an underlined.

OR GATES

The CAR of the present invention may be used in a combination with one or more other activatory or inhibitory chimeric antigen receptors. For example, they may be used in combination with one or more other CARs in a "logic-gate", a CAR combination which, when expressed by a cell, such as a T cell, are capable of detecting a particular pattern of expression of at least two target antigens. If the at least two target antigens are arbitrarily denoted as antigen A and antigen B, the three possible options are as follows:

"OR GATE"—T cell triggers when either antigen A or antigen B is present on the target cell "AND GATE"—T cell triggers only when both antigens A and B are present on the target cell "AND NOT GATE"—T cell triggers if antigen A is present alone on the target cell, but not if both antigens A and B are present on the target cell Engineered T cells expressing these CAR combinations can be tailored to be exquisitely specific for cancer cells, based on their particular expression (or lack of expression) of two or more markers.

Such "Logic Gates" are described, for example, in WO2015/075469, WO2015/075470 and WO2015/075470.

An "OR Gate" comprises two or more activatory CARs each directed to a distinct target antigen expressed by a target cell. The advantage of an OR gate is that the effective targetable antigen is increased on the target cell, as it is effectively antigen A+antigen B. This is especially important for antigens expressed at variable or low density on the target cell, as the level of a single antigen may be below the threshold needed for effective targeting by a CAR-T cell. Also, it avoids the phenomenon of antigen escape. For example, some lymphomas and leukemias become CD19 negative after CD19 targeting: using an OR gate which targets CD19 in combination with another antigen provides a "back-up" antigen, should this occur.

The FabCAR of the present invention may be used in an OR gate in combination with a second CAR against a second target antigen expressed by the target cell.

For an anti-CD22 FabCAR, the OR gate may comprise a CAR against a second antigen expressed in B cells, such as CD19, CD20 or CD79.

The second CAR may have any suitable antigen binding domain, for example a binding domain based on an scFv, a domain antibody (dAb) or a Fab.

TABLE 2

| Antibody | VH | VL |
|---|---|---|
| 1F6 | QVQLKESGPGLVQPSQTLSLTCTVSGFSLTSYTVSWVRQPPGKGLEWIAAISSGGSTYYNSALKSRLSISRDTSKSQVFLKMNSLQTEDTAMYFCARYTTDSGFDYWGQGVMVTVSS (SEQ ID No. 107) | DIQMTQSPSVLSASVGDRVTLSCKASQNINKNLDWYQQKLGEAPKWYFTNNLQTGIPSRFSGSGSGTDYTLTISSLQPEDVATYYCYQYNSGWTFGGGTKLELK (SEQ ID No. 108) |
| 2H9 | EVQLVESGGDLVQPGRSLKLSCASSGFTFSDYNMAWVRQAPKKGLEWVATISYDGTNTYYRDSVKGRFTISRDNAKSTLYLQMDSLRSEDTATYYCARQDSSYVYLSWFAYWGQGTLVTVSS (SEQ ID No. 109) | DIQMTQSPASLSASLGETVTIECRASEDIYNGLTWYQQKPGKSPQLLISNANCLHTGVPSRFSGSGSGTQYSLKINSLQSEDVASYFCQQYYNYPWTFGGGTKLDLK (SEQ ID No. 110) |
| 7F10 | QVQLKESGPGLVQPSQTLSLTCTVSGFSLTSYTVSWVRQPPGRGLEWIAAISSGGNTYYNSGLKSRLSISRDTSKSQVFLKMNSLQTEDTAMYFCARYAQIRGKDYWGQGVMVTVSS (SEQ ID No. 111) | DIQMTQSPPILSASVGDRVTLSCKASQNINKNLDWYQQKHGEAPKLLIYYTHNLQTGIPSRFSGSGSGTDYTLTISSLQPEDVATYYCYQYYSGWTFGGGTKLQLK (SEQ ID No. 112) |

The second CAR may comprise a spacer to spatially separate the antigen binding domain from the transmembrane domain and provide a degree of flexibility. A variety of sequences are commonly used as spacers for CAR, for example, an IgG1 Fc region, an IgG1 hinge (as described above) or a human CD8 stalk. The spacer may comprise a coiled-coil domain, for example as described in WO2016/151315.

The second CAR comprises an activating endodomain. It may, for example comprise the endodomain from CD3. It may comprise one or more co-stimulatory domains as described above. For example, it may comprise the endodomains from CD28, OX-40 or 4-1BB.

The FabCAR of the present invention may be used in a triple OR gate, which comprises a second CAR against a second antigen and a third CAR against a third antigen expressed by the target cell.

For an anti-CD22 FabCAR, a triple OR gate may comprise CARs against second and third antigens expressed in B cells, such as CD19, CD20 or CD79.

In particular, the present invention provides a triple OR gate which comprises:
  (i) an anti-CD22 FabCAR;
  (ii) an anti-CD79 dAb CAR; and
  (iii) an anti-CD19 scFv CAR (see FIG. 7b).

DUAL FAB CARS

The OR gate of the present invention may comprise two (or more) Fab CARs.

Figure 11:
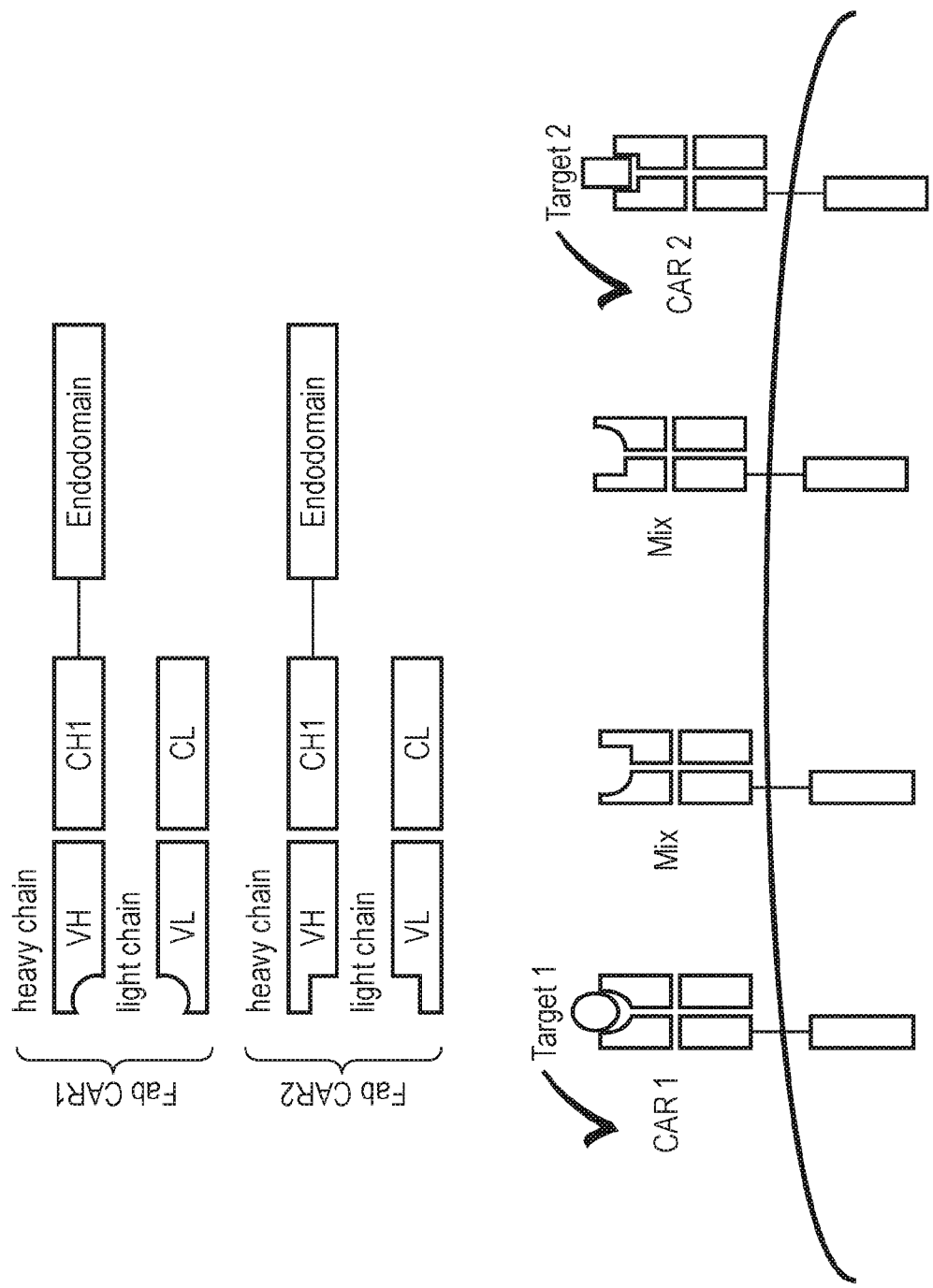

A problem associated with the expression of two Fab CARs is cross pairing or mis-pairing events, creating non-functional CARs (FIG. 11). In order to avoid this "Crossmab" and/or "Ortho-Fab" formats may be used, as illustrated schematically in FIG. 12.

Figure 12:
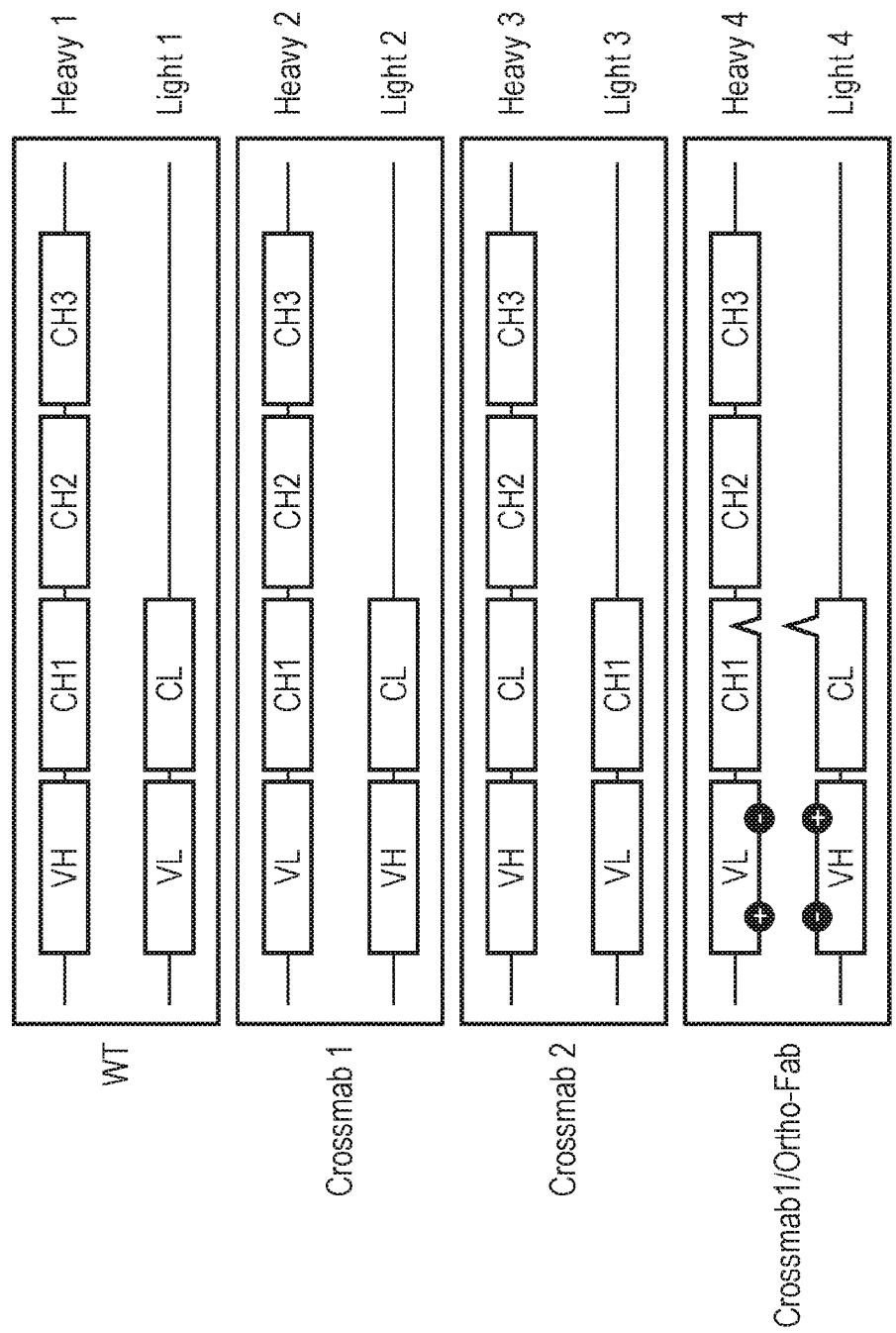
FIG. 12—Schematic diagram illustrating "Crossmab" and "Ortho-Fab" to avoid cross-pairing between FabCARs.

"Crossmab" involves switching the CL and CH1 domains between chains so that a variable light chain (VL) is connected to a heavy chain constant domain (CH) in one molecule; and that a variable heavy chain (VH) is connected to a light chain constant domain (CL) in the other molecule (FIG. 12, Crossmab 1 and 2).

A nucleic acid construct encoding a FabCAR in a crossmab format may have the structure:
  VH-CL-spacer-TM-endo-coexpr-VL-CH or
  VL-CH-spacer-TM-endo-coexpr-VH-CL
in which:
  VH is a nucleic acid sequence encoding a heavy chain variable region;
  CH is a nucleic acid sequence encoding a heavy chain constant region spacer is a nucleic acid encoding a spacer;
  TM is a a nucleic acid sequence encoding a transmembrane domain;
  endo is a nucleic acid sequence encoding an endodomain;
  coexpr is a nucleic acid sequence enabling co-expression of the first and second polypeptides;
  VL is a nucleic acid sequence encoding a light chain variable region; and
  CL is a nucleic acid sequence encoding a light chain constant region.

"Ortho-Fab" involves introducing mutations to avoid alternative combinations. For example, amino acids with bulky side chains may be engineered into one chain (e.g. CL) to create a protrusion and the correctly pairing domain (e.g. CH) may be engineered to accommodate the protrusion. Alternatively, or in addition electrically charged side chains may be engineered into one chain (e.g. VH engineered to have positively charged amino acid) and the correctly pairing domain (e.g. VL) be engineered to have a negatively charges amino acid.

A Dual FabCAR of the invention may comprise a CD19 Fab CAR having the CDRs shown as SEQ ID No. 69-74 in a wild-type Fab CAR format; and a CD22 Fab CAR having the CDRs shown as SEQ ID No. 93-98 in an orthoFab or crossmab1 Fab CAR format.

CD79 Binders

The term "CD79" or "Cluster of differentiation 79" refers to the protein at the surface of B cells that encompasses two transmembrane proteins, CD79a and CD79b, which form a disulfide-linked heterodimer and are members of the immunoglobulin (Ig) gene superfamily. The transmembrane CD79a and CD79b proteins couple at the extracellular end with any one of the five different types of transmembrane Ig molecules (IgM, IgD, IgG, IgE, or IgA), which are disulfide-linked proteins composed of two Ig heavy chains and two Ig light chains. This combination of CD79 and immunoglobulin on the B-cell surface forms the B-cell signalling receptor (BCR). The intracytoplasmic domains of CD79a and CD79b contain immunoreceptor tyrosine-based activation motifs (ITAMs) that transmit activation signals to the B-cell upon antigen-induced BCR aggregation.

CD79 expression is restricted to Pre-B cells and mature B cells (excluding plasma cells). CD79 is also expressed on a majority of B-cell-derived malignancies. This narrow expression pattern makes it a promising target for cancer-targeted therapies with minimal targeting to normal tissue.

The term "CD79a" or "CD79A" refers to the B-cell antigen receptor complex-associated protein alpha chain also known as Ig-alpha, MB-1 membrane glycoprotein, membrane-bound immunoglobulin-associated protein, and surface IgM-associated protein. The human isoforms of CD79a are depicted under Accession Nos. P11912.1 (Isoform 1 or long) and P11912.2 (Isoform 2 or short) in the Uniprot database on 20 Apr. 2018.

The term "CD79b" or "CD79B" refers to the B-cell antigen receptor complex-associated protein beta chain also known as Ig-beta, B-cell-specific glycoprotein B29, and immunoglobulin-associated B29 protein. The human isoforms of CD79b are depicted under Accession Nos. P40259-1 (Isoform long), P40259-2 (Isoform short) and P40259-3 (Isoform 3) in the Uniprot database on 20 Apr. 2018.

Activated B lymphocytes have increased amounts of the short or truncated CD79 isoforms. In a particular embodiment, the invention relates to a CAR which specifically binds CD79a. In a preferred embodiment, the CAR binds the unspliced portion or CD79a ectodomain, i.e. residues 33 to 143 of CD79a isoform 1, shown below as SEQ ID No. 67 (Uniprot Accession No. P11912.1). In another particular embodiment, the invention relates to a CAR which specifically binds CD79b. In another preferred embodiment, the CAR binds the unspliced portion or CD79b ectodomain, i.e. residues 29 to 159 of CD79b isoform long, shown below as SEQ ID No. 68 (Uniprot Accession No. P40259-1).

CD79a isoform 1
SEQ ID No. 67
MPGGPGVLQALPATIFLLFLLSAVYLGPGCQALWMHKVPASLMVSLG

EDAHFQCPHNSSNNANVTWWRVLHGNYTWPPEFLGPGEDPNGTLIIQ

NVNKSHGGIYVCRVQEGNESYQQSCGTYLRVRQPPPRPFLDMGEGTK

NRIITAEGIILLFCAVVPGTLLLFRKRWQNEKLGLDAGDEYEDENLY

EGLNLDDCSMYEDISRGLQGTYQDVGSLNIGDVQLEKP

-continued

CD79b isoform 2
SEQ ID No. 68
MARLALSPVPSHWMVALLLLLSAEPVPAARSEDRYRNPKGSACSRIW

QSPRFIARKRGFTVKMHCYMNSASGNVSWLWKQEMDENPQQLKLEKG

RMEESQNESLATLTIQGIRFEDNGIYFCQQKCNNTSEVYQGCGTELR

VMGFSTLAQLKQRNTLKDGIIMIQTLLIILFIIVPIFLLLDKDDSKA

GMEEDHTYEGLDIDQTATYEDIVTLRTGEVKWSVGEHPGQE

The invention provides OR gates comprising a chimeric antigen receptor (CAR) which binds CD79.

The CAR may specifically bind CD79 Å. For example, it may bind the unspliced portion of CD79 Å ectodomain (residues 33 to 143 of SEQ ID NO: 67).

The CAR may specifically bind CD79B. For example it may bind the unspliced portion of CD79B ectodomain (residues 29 to 159 of SEQ ID NO: 68).

Numerous anti-CD79 antibodies are known in the art, for example JCB117, SN8, CB3.1 and 2F2 (Polatuzumab).

The CD79-binding domain may comprise
a) a heavy chain variable region (VH) having complementarity determining regions (CDRs) with the following sequences:

```
                              (SEQ ID No. 5)
          CDR1 - SDYAWN;
                              (SEQ ID No. 6)
          CDR2 - NIWYSGSTTYNPSLKS
                              (SEQ ID No. 7)
          CDR3 - MDF;
``` and
b) a light chain variable region (VL) having CDRs with the following sequences:

```
                              (SEQ ID No. 8)
          CDR1 - RASESVDSYGKTFMHWH;
                              (SEQ ID No. 9)
          CDR2 - RVSNLES
                              (SEQ ID No. 10)
          CDR3 - QQSNEDPFT.
```

The anti-CD79 CAR may comprise the following VH sequence:

```
VH sequence from murine monoclonal antibody
                              SEQ ID No. 11
EVQLQESGPGLVKPSQSLSLTCTVTGYSITSDYAWNWIRQFPGNKLEW

MGNIWYSGSTTYNPSLKSRISITRDTSKNQFFLQLNSVTSEDTATYYC

SRMDFWGQGTTLTVSS
```

The anti-CD79 CAR may comprise the following VL sequence:

```
VL sequence from murine monoclonal antibody
                              SEQ ID No 12
DIVLTQSPPSLAVSLGQRATISCRASESVDSYGKTFMHWHQQKPGQPP

KLLIYRVSNLESGIPARFSGSGSRTDFTLTINPVEADDVATYYCQQSN

EDPFTFGGGTKLEIKR
```

The anti-CD79 CAR may comprise the following scFv sequence:

```
(mouse anti-cynomolgus (Macaca fascicularis)
CD79b 10D10 scFv)
                              SEQ ID NO: 13
DIVLTQSPPSLAVSLGQRATISCRASESVDSYGKTFMHWHQQKPGQPP

KLLIYRVSNLESGIPARFSGSGSRTDFTLTINPVEADDVATYYCQQSN

EDPFTFGGGTKLEIKRSGGGSGGGGSGGGGSGGGGSEVQLQESGPGL

VKPSQSLSLTCTVTGYSITSDYAWNWIRQFPGNKLEWMGNIWYSGSTT

YNPSLKSRISITRDTSKNQFFLQLNSVTSEDTATYYCSRMDFWGQGTT

LTVSS
```

Alternatively, the anti-CD79 CAR may comprise an antigen-binding domain which comprises a) a heavy chain variable region (VH) having complementarity determining regions (CDRs) with the following sequences:

```
                              (SEQ ID No. 14)
          CDR1 - SYWIE;
                              (SEQ ID No. 15)
          CDR2 - EILPGGGDTNYNEIFKG
                              (SEQ ID No. 16)
          CDR3 - RVPVYFDY;
``` and
b) a light chain variable region (VL) having CDRs with the following sequences:

```
                              (SEQ ID No. 17)
          CDR1 - KASQSVDYDGDSFLN;
                              (SEQ ID No. 18)
          CDR2 - AASNLES
                              (SEQ ID No. 19)
          CDR3 - QQSNEDPLT.
```

The anti-CD79 CAR may comprise the following VH sequence:

```
VH sequence from murine monoclonal antibody
                              SEQ ID No. 20
EVQLVESGGGLVQPGGSLRLSCAASGYTFSSYWIEWVRQAPGKGLEWI

GEILPGGGDTNYNEIFKGRATFSADTSKNTAYLQMNSLRAEDTAVYYC

TRRVPVYFDYWGQGTLVTVSS
```

The anti-CD79 CAR may comprise the following VL sequence:

```
VL sequence from murine monoclonal antibody
                              SEQ ID No 21
DIQLTQSPSSLSASVGDRVTITCKASQSVDYDGDSFLNWYQQKPGKAP

KLLIYAASNLESGVPSRFSGSGSGTDFTLTISSLQPEDFATYYCQQSN

EDPLTFGQGTKVEIKR
```

The anti-CD79 CAR may comprise the following scFv sequence:

```
(humanised anti-CD79b-v17 scFv)
                                       SEQ ID NO: 22
METDTLLLWVLLLWVPGSTGDIQLTQSPSSLSASVGDRVTITCKASQS
VDYDGDSFLNWYQQKPGKAPKLLIYAASNLESGVPSRFSGSGSGTDFT
LTISSLQPEDFATYYCQQSNEDPLTFGQGTKVEIKRSGGGGSGGGGSG
GGGSGGGGSEVQLVESGGGLVQPGGSLRLSCAASGYTFSSYWIEWVRQ
APGKGLEWIGEILPGGGDTNYNEIFKGRATFSADTSKNTAYLQMNSLR
AEDTAVYYCTRRVPVYFDYWGQGTLVTVSS
```

Alternatively, the anti-CD79 CAR may comprise an antigen-binding domain which comprises a) a heavy chain variable region (VH) having complementarity determining regions (CDRs) with the following sequences:

```
CDR1
                                       (SEQ ID No. 14)
SYWIE;

CDR2
                                       (SEQ ID No. 15)
EILPGGGDTNYNEIFKG

CDR3
                                       (SEQ ID No. 23)
RVPIRLDY;
``` and b) a light chain variable region (VL) having CDRs with the following sequences:

```
CDR1
                                       (SEQ ID No. 17)
KASQSVDYDGDSFLN;

CDR2
                                       (SEQ ID No. 18)
AASNLES

CDR3
                                       (SEQ ID No. 19)
QQSNEDPLT.
```

The anti-CD79 CAR may comprise the following VH sequence:

```
VH sequence from murine monoclonal antibody
                                       SEQ ID No. 24
EVQLVESGGGLVQPGGSLRLSCAASGYTFSSYWIEVVVRQAPGKGLEWIG
EILPGGGDTNYNE1FKGRATFSADTSKNTAYLQMNSLRAEDTAVYYCTRR
VPIRLDYWGQGTLVTVSS
```

The anti-CD79 CAR may comprise the following VL sequence:

```
VL sequence from murine monoclonal antibody
                                       SEQ ID No. 21
DIQLTQSPSSLSASVGDRVTITCKASQSVDYDGDSFLNVVYQQKPGKAPK
LLIYAASNLESGVPSRFSGSGSGTDFTLTISSLQPEDFATYYCQQSNEDP
LTFGQGTKVEIKR
```

The anti-CD79 CAR may comprise the following scFv sequence:

```
(humanised anti-CD79b v18 scFv)
                                       SEQ ID NO: 25
DIQLTQSPSSLSASVGDRVTITCKASQSVDYDGDSFLNVVYQQKPGKAPK
LLIYAASNLESGVPSRFSGSGSGTDFTLTISSLQPEDFATYYCQQSNEDP
LTFGQGTKVEIKRSGGGGSGGGGSGGGGSGGGGSEVQLVESGGGLVQPGG
SLRLSCAASGYTFSSYWIEVVVRQAPGKGLEWIGEILPGGGDTNYNEIFK
GRATFSADTSKNTAYLQMNSLRAEDTAVYYCTRRVPIRLDYWGQGTLVTV
SS
```

Alternatively, the anti-CD79 CAR may comprise an antigen-binding domain which comprises a) a heavy chain variable region (VH) having complementarity determining regions (CDRs) with the following sequences:

```
CDR1
                                       (SEQ ID No. 14)
SYWIE;

CDR2
                                       (SEQ ID No. 15)
EILPGGGDTNYNEIFKG

CDR3
                                       (SEQ ID No. 23)
RVPIRLDY;
``` and b) a light chain variable region (VL) having CDRs with the following sequences:

```
CDR1
                                       (SEQ ID No. 26)
KASQSVDYEGDSFLN;

CDR2
                                       (SEQ ID No. 18)
AASNLES

CDR3
                                       (SEQ ID No. 19)
QQSNEDPLT.
```

The anti-CD79 CAR may comprise the following VH sequence:

```
VH sequence from murine monoclonal antibody
                                       SEQ ID No. 24
EVQLVESGGGLVQPGGSLRLSCAASGYTFSSYWIEVVVRQAPGKGLEWIG
EILPGGGDTNYNEIFKGRATFSADTSKNTAYLQMNSLRAEDTAVYYCTRR
VPIRLDYWGQGTLVTVSS
```

The anti-CD79 CAR may comprise the following VL sequence:

```
VL sequence from murine monoclonal antibody
                                       SEQ ID No. 27
DIQLTQSPSSLSASVGDRVTITCKASQSVDYEGDSFLNVVYQQKPGKAPK
LLIYAASNLESGVPSRFSGSGSGTDFTLTISSLQPEDFATYYCQQSNEDP
LTFGQGTKVEIKR
```

The anti-CD79 CAR may comprise the following scFv sequence:

```
(humanised anti-CD79b v28 scFv)
                                      SEQ ID NO: 28
METDTLLLWVLLLVVVPGSTGDIQLTQSPSSLSASVGDRVTITCKASQS

VDYEGDSFLNWYQQKPGKAPKLLIYAASNLESGVPSRFSGSGSGTDFTL

TISSLQPEDFATYYCQQSNEDPLTFGQGTKVEIKRSGGGGSGGGGSGGGG

SGGGGSEVQLVESGGGLVQPGGSLRLSCAASGYTFSSYWIEVVVRQAPGK

GLEWIGEILPGGGDTNYNEIFKGRATFSADTSKNTAYLQMNSLRAEDTAV

YYCTRRVPIRLDYWGQGTLVTVSS
```

Alternatively, the anti-CD79 CAR may comprise an antigen-binding domain which comprises a) a heavy chain variable region (VH) having complementarity determining regions (CDRs) with the following sequences:

```
CDR1
                                       (SEQ ID No. 14)
SYWIE;

CDR2
                                       (SEQ ID No. 15)
EILPGGGDTNYNEIFKG

CDR3
                                       (SEQ ID NO: 23)
RVPIRLDY;
``` and
b) a light chain variable region (VL) having CDRs with the following sequences:

```
CDR1
                                       (SEQ ID No. 29)
KASQSVDYSGDSFLN;

CDR2
                                       (SEQ ID No. 18)
AASNLES

CDR3
                                       (SEQ ID No. 19)
QQSNEDPLT
```

The anti-CD79 CAR may comprise the following VH sequence:

```
VH sequence from murine monoclonal antibody
                                       SEQ ID No. 24
EVQLVESGGGLVQPGGSLRLSCAASGYTFSSYWIEWVRQAPGKGLEWIG

EILPGGGDTNYNEIFKGRATFSADTSKNTAYLQMNSLRAEDTAVYYCTRR

VPIRLDYWGQGTLVTVSS
```

The anti-CD79 CAR may comprise the following VL sequence:

```
VL sequence from murine monoclonal antibody
                                       SEQ ID No. 30
DIQLTQSPSSLSASVGDRVTITCKASQSVDYSGDSFLNWYQQKPGKAPK

LFIYAASNLESGVPSRFSGSGSGTDFTLTISSLQPEDFATYYCQQSNEDP

LTFGQGTKVEIKR
```

The anti-CD79 CAR may comprise the following scFv sequence:

```
(humanised anti-CD79b v32 scFv)
                                       SEQ ID NO: 31
METDTLLLWVLLLVVVPGSTGDIQLTQSPSSLSASVGDRVTITCKASQS

VDYSGDSFLNWYQQKPGKAPKLFIYAASNLESGVPSRFSGSGSGTDFTL

TISSLQPEDFATYYCQQSNEDPLTFGQGTKVEIKRSGGGGSGGGGSGGGG

SGGGGSEVQLVESGGGLVQPGGSLRLSCAASGYTFSSYWIEWVRQAPGK

GLEWIGEILPGGGDTNYNEIFKGRATFSADTSKNTAYLQMNSLRAEDTAV

YYCTRRVPIRLDYWGQGTLVTVSS
```

Alternatively, the anti-CD79 CAR may comprise an antigen-binding domain which comprises a) a heavy chain variable region (VH) having complementarity determining regions (CDRs) with the following sequences:

```
CDR1
                                       (SEQ ID No. 14)
SYWIE;

CDR2
                                       (SEQ ID No. 15)
EILPGGGDTNYNEIFKG

CDR3
                                       (SEQ ID NO: 16)
RVPVYFDY;
``` and
b) a light chain variable region (VL) having CDRs with the following sequences:

```
CDR1
                                       (SEQ ID No. 17)
KASQSVDYDGDSFLN;

CDR2
                                       (SEQ ID No. 18)
AASNLES

CDR3
                                       (SEQ ID No. 19)
QQSNEDPLT.
```

The anti-CD79 CAR may comprise the following VH sequence:

```
VH sequence from murine monoclonal antibody
                                       SEQ ID No. 32
EVQLQQSGAELMKPGASVKISCKATGYTFSSYWIE

WVKQRPGHGLEWIGEILPGGGDTNYNEIFKGKATF

TADTSSNTAYMQLSSLTSEDSAVYYCTRRVPVYFD

WGQGTSVTVSS
```

The anti-CD79 CAR may comprise the following VL sequence:

```
VL sequence from murine monoclonal antibody
                                       SEQ ID No. 33
DIVLTQSPASLAVSLGQRATISCKASQSVDYDGDSF

LNVVYQQKPGQPPKLFIYAASNLESGIPARFSGSGS

GTDFTLNIHPVEEEDAATYYCQQSNEDPLTFGAGTE

LELKR
```

The anti-CD79 CAR may comprise the following scFv sequence:

```
(murine anti-CD79b SN8 scFv)
                                  SEQ ID NO: 34
METDTLLLWVLLLWVPGSTGDIVLTQSPASLAVSL

GQRATISCKASQSVDYDGDSFLNWYQQKPGQPPKL

FIYAASNLESGIPARFSGSGSGTDFTLNIHPVEEE

DAATYYCQQSNEDPLTFGAGTELELKRSGGGGSGG

GGSGGGGSGGGGSEVQLQQSGAELMKPGASVKISC

KATGYTFSSYWIEWVKQRPGHGLEWIGEILPGGGD

TNYNEIFKGKATFTADTSSNTAYMQLSSLTSEDSA

VYYCTRRVPVYFDYWGQGTSVTVSS
```

Alternatively, the anti-CD79 CAR may comprise an antigen-binding domain which comprises a) a heavy chain variable region (VH) having complementarity determining regions (CDRs) with the following sequences:

```
CDR1
                                  (SEQ ID No. 14)
SYWIE;

CDR2
                                  (SEQ ID No. 15)
EILPGGGDTNYNEIFKG

CDR3
                                  (SEQ ID NO: 23)
RVPIRLDY;
``` and
b) a light chain variable region (VL) having CDRs with the following sequences:

```
CDR1
                                  (SEQ ID No. 26)
KASQSVDYEGDSFLN;

CDR2
                                  (SEQ ID No. 18)
AASNLES

CDR3
                                  (SEQ ID No. 19)
QQSNEDPLT.
```

The anti-CD79 CAR may comprise the following VH sequence:

```
VH sequence from murine monoclonal antibody
                                  SEQ ID No. 24
EVQLVESGGGLVQPGGSLRLSCAASGYTFSSYWIEWVRQA

PGKGLEWIGEILPGGGDTNYNE1FKGRATFSADTSKNTAYL

QMNSLRAEDTAVYYCTRRVPIRLDYWGQGTLVTVSS
```

The anti-CD79 CAR may comprise the following VL sequence:

```
VL sequence from murine monoclonal antibody
                                  SEQ ID No. 27
DIQLTQSPSSLSASVGDRVTITCKASQSVDYEGDSFLNWY

QQKPGKAPKLLIYAASNLESGVPSRFSGSGSGTDFTLTISS

LQPEDFATYYCQQSNEDPLTFGQGTKVEIKR
```

The anti-CD79 CAR may comprise the following scFv sequence:

```
(humanised anti-CD79b 2F2 scFv)
                                  SEQ ID NO: 28
METDTLLLWVLLLWVPGSTGDIQLTQSPSSLSASVGDRVTITC

KASQSVDYEGDSFLNWYQQKPGKAPKLLIYAASNLESGVPSRF

SGSGSGTDFTLTISSLQPEDFATYYCQQSNEDPLTFGQGTKVE

IKRSGGGGSGGGGSGGGGSGGGGSEVQLVESGGGLVQPGGSLR

LSCAASGYTFSSYWIEWVRQAPGKGLEWIGEILPGGGDTNYNE

IFKGRATFSADTSKNTAYLQMNSLRAEDTAVYYCTRRVPIRLD

YWGQGTLVTVSS
```

Alternatively, the anti-CD79 CAR may comprise an antigen-binding domain which comprises a) a heavy chain variable region (VH) having complementarity determining regions (CDRs) with the following sequences:

```
CDR1
                                  (SEQ ID No. 15)
NYGMN;

CDR2
                                  (SEQ ID No. 16)
RIYPGSGSTNYQKFKG

CDR3
                                  (SEQ ID NO: 35)
YAMDY;
``` and
b) a light chain variable region (VL) having CDRs with the following sequences:

```
CDR1
                                  (SEQ ID No. 18)
RSSQSIVHSNGNTYLE;

CDR2
                                  (SEQ ID No. 19)
KVSNRPS

CDR3
                                  (SEQ ID No. 20)
FQGSHVPWT.
```

The anti-CD79 CAR may comprise the following VH sequence:

```
VH sequence from murine monoclonal antibody
                                  SEQ ID No. 36
QVQLQQSGPELVKPGASVKISCKASGYTFTNYGMNWVKQRPGQGL

QWIGRIYPGSGSTNYQKFKGKATLTVDKSSSTAYMELRSLTSENS

AVYYCARYAMDYTGQGTSVTVSS
```

The anti-CD79 CAR may comprise the following VL sequence:

```
VL sequence from murine monoclonal antibody
                                  SEQ ID No. 37
DVLMTQTPLSLPVSLGDQASISCRSSQSIVHSNGNTYLEWYLQKP

GQSPKLLIYKVSNRPSGVPNRFSGSGSGTDFTLKISRVQAQNLGV

YYCFQGSHVPWTFGGGTKLEIKR
```

The anti-CD79 CAR may comprise the following scFv sequence:

```
(murine anti-CD79a scFv)
                                       SEQ ID NO: 38
METDTLLLWVLLLWVPGSTGDVLMTQTPLSLPVSLGDQASISCR

SSQSIVHSNGNTYLEWYLQKPGQSPKLLIYKVSNRPSGVPNRFS

GSGSGTDFTLKISRVQAQNLGVYYCFQGSHVPWTFGGGTKLEIK

RSGGGGSGGGGSGGGGSGGGGSQVQLQQSGPELVKPGASVKISC

KASGYTFTNYGMNWVKQRPGQGLQWIGRIYPGSGSTNYQKFKGK

ATLTVDKSSSTAYMELRSLTSENSAVYYCARYAMDYTGQGTSVT

VSS
```

It may be possible to introduce one or more mutations (substitutions, additions or deletions) into the or each CDR without negatively affecting CD79-binding activity. Each CDR may, for example, have one, two or three amino acid mutations.

CD19 Binders

Several anti-CD19 antibodies have been previously described in a CAR format, such as fmc63, 4G7, SJ25C1, CAT19 (as described in WO2016/139487) and CD19ALAb (as described in WO2016/102965)

An anti-CD19 CAR for use in a double or triple OR gate of the present invention may comprise an antigen-binding domain, such as an scFv-type antigen binding domain, derived from one of these anti-CD19 antibodies.

The CD19-binding domain may comprises
a) a heavy chain variable region (VH) having complementarity determining regions (CDRs) with the following sequences:

```
                              (SEQ ID No. 69)
        CDR1 - GYAFSSS;

(SEQ ID No. 70)
        CDR2 - YPGDED (SEQ ID No. 71)
        CDR3 - SLLYGDYLDY;
``` and
b) a light chain variable region (VL) having CDRs with the following sequences:

```
                              (SEQ ID No. 72)
        CDR1 - SASSSVSYMH;

(SEQ ID No. 73)
        CDR2 - DTSKLAS (SEQ ID No. 74)
        CDR3 - QQWNINPLT.
```

It may be possible to introduce one or more mutations (substitutions, additions or deletions) into each CDR without negatively affecting CD19-binding activity. Each CDR may, for example, have one, two or three amino acid mutations.

The CDRs may be in the format of a single-chain variable fragment (scFv), which is a fusion protein of the heavy variable region (VH) and light chain variable region (VL) of an antibody, connected with a short linker peptide of ten to about 25 amino acids. The scFv may be in the orientation VH-VL, i.e. the VH is at the amino-terminus of the CAR molecule and the VL domain is linked to the spacer and, in turn the transmembrane domain and endodomain.

The CDRs may be grafted on to the framework of a human antibody or scFv. For example, the CAR of the present invention may comprise a CD19-binding domain consisting or comprising one of the following sequences The anti-CD19 CAR may comprise the following VH sequence:

```
VH sequence from murine monoclonal antibody
                                       SEQ ID No. 75
QVQLQQSGPELVKPGASVKISCKASGYAFSSSWMNWVKQRPGKGLEWIG

RIYPGDEDTNYSGKFKDKATLTADKSSTTAYMQLSSLTSEDSAVYFCAR

SLLYGDYLDYWGQGTTLTVSS
```

The anti-CD19 CAR may comprise the following VL sequence:

```
VL sequence from murine monoclonal antibody
                                       SEQ ID No 76
QIVLTQSPAIMSASPGEKVTMTCSASSSVSYMHWYQQKSGTSPKRWIYD

TSKLASGVPDRFSGSGSGTSYFLTINNMEAEDAATYYCQQWNINPLTFG

AGTKLELKR
```

The anti-CD19 CAR may comprise the following scFv sequence:

```
VH-VL scFv sequence from murine monoclonal
antibody
                                       SEQ ID No 77
QVQLQQSGPELVKPGASVKISCKASGYAFSSSWMNWVKQRPGKGLEWIG

RIYPGDEDTNYSGKFKDKATLTADKSSTTAYMQLSSLTSEDSAVYFCAR

SLLYGDYLDYWGQGTTLTVSSGGGGSGGGGSGGGGSQIVLTQSPAIMSA

SPGEKVTMTCSASSSVSYMHWYQQKSGTSPKRWIYDTSKLASGVPDRFS

GSGSGTSYFLTINNMEAEDAATYYCQQWNINPLTFGAGTKLELKR
```

Alternatively, the anti-CD19 CAR may comprise an antigen-binding domain which comprises a) a heavy chain variable region (VH) having complementarity determining regions (CDRs) with the following sequences:

```
                              (SEQ ID No. 78)
        CDR1 - SYWMN;

(SEQ ID No. 79)
        CDR2 - QIWPGDGDTNYNGKFK (SEQ ID No. 80)
        CDR3 - RETTTVGRYYYAMDY;
``` and
b) a light chain variable region (VL) having CDRs with the following sequences:

```
                              (SEQ ID No. 81)
        CDR1 - KASQSVDYDGDSYLN;

(SEQ ID No. 82)
        CDR2 - DASNLVS (SEQ ID No. 83)
        CDR3 - QQSTEDPWT.
```

It may be possible to introduce one or more mutations (substitutions, additions or deletions) into the or each CDR without negatively affecting CD19-binding activity. Each CDR may, for example, have one, two or three amino acid mutations.

The CAR of the present invention may comprise one of the following amino acid sequences:

(Murine CD19ALAb scFv sequence)
SEQ ID No. 84
QVQLQQSGAELVRPGSSVKISCKASGYAFSSYWMNWVKQRPGQGLEWI

GQIWPGDGDTNYNGKFKGKATLTADESSSTAYMQLSSLASEDSAVYFC

ARRETTTVGRYYYAMDYWGQGTTVTVSSDIQLTQSPASLAVSLGQRAT

ISCKASQSVDYDGDSYLNWYQQIPGQPPKLLIYDASNLVSGIPPRFSG

SGSGTDFTLNIHPVEKVDAATYHCQQSTEDPWTFGGGTKLEIK (Humanised CD19ALAb scFv sequence - Heavy 19, Kappa 16)
SEQ ID No. 85
QVQLVQSGAEVKKPGASVKLSCKASGYAFSSYWMNWVRQAPGQSLEWI

GQIWPGDGDTNYNGKFKGRATLTADESARTAYMELSSLRSGDTAVYFC

ARRETTTVGRYYYAMDYWGKGTLVTVSSDIQLTQSPDSLAVSLGERAT

INCKASQSVDYDGDSYLNWYQQKPGQPPKLLIYDASNLVSGVPDRFS

GSGSGTDFTLTISSLQAADVAVYHCQQSTEDPWTFGQGTKVEIKR (Humanised CD19ALAb scFv sequence - Heavy 19, Kappa 7)
SEQ ID No. 86
QVQLVQSGAEVKKPGASVKLSCKASGYAFSSYWMNWVRQAPGQSLEWI

GQIWPGDGDTNYNGKFKGRATLTADESARTAYMELSSLRSGDTAVYFC

ARRETTTVGRYYYAMDYWGKGTLVTVSSDIQLTQSPDSLAVSLGERAT

INCKASQSVDYDGDSYLNWYQQKPGQPPKVLIYDASNLVSGVPDRFSG

SGSGTDFTLTISSLQAADVAVYYCQQSTEDPWTFGQGTKVEIKR

The scFv may be in a VH-VL orientation (as shown in SEQ ID No.s 84, 85 and 86) or a VL-VH orientation.

The CAR of the present invention may comprise one of the following VH sequences:

(Murine CD19ALAb VH sequence)
SEQ ID No. 87
QVQLQQSGAELVRPGSSVKISCKASGYAFSSYWMNWVKQRPGQGLEWI

GQIWPGDGDTNYNGKFKGKATLTADESSSTAYMQLSSLASEDSAVYFC

ARRETTTVGRYYYAMDYWGQGTTVTVSS (Humanised CD19ALAb VH sequence)
SEQ ID No. 88
QVQLVQSGAEVKKPGASVKLSCKASGYAFSSYWMNWVRQAPGQSLEWI

GQIWPGDGDTNYNGKFKGRATLTADESARTAYMELSSLRSGDTAVYFC

ARRETTTVGRYYYAMDYWGKGTLVTVSS

An anti-CD19 CAR may comprise one of the following VL sequences:

(Murine CD19ALAb VL sequence)
SEQ ID No. 89
DIQLTQSPASLAVSLGQRATISCKASQSVDYDGDSYLNWYQQIPGQPP

KLLIYDASNLVSGIPPRFSGSGSGTDFTLNIHPVEKVDAATYHCQQST

EDPWTFGGGTKLEIK (Humanised CD19ALAb VL sequence, Kappa 16)
SEQ ID No. 90
DIQLTQSPDSLAVSLGERATINCKASQSVDYDGDSYLNWYQQKPGQPP

KWYDASNLVSGVPDRFSGSGSGTDFTLTISSLQAADVAVYHCQQSTED

PWTFGQGTKVEIKR (Humanised CD19ALAb VL sequence, Kappa 7)
SEQ ID No. 91
DIQLTQSPDSLAVSLGERATINCKASQSVDYDGDSYLNWYQQKPGQPPK

VLIYDASNLVSGVPDRFSGSGSGTDFTLTISSLQAADVAVYYCQQSTED

PWTFGQGTKVEIKR

The CAR may comprise a variant of the sequence shown as SEQ ID No. 84 to 91 having at least 80, 85, 90, 95, 98 or 99% sequence identity, provided that the variant sequence retain the capacity to bind CD19 (when in conjunction with a complementary VL or VH domain, if appropriate).

The percentage identity between two polypeptide sequences may be readily determined by programs such as BLAST which is freely available at http://blast.ncbi.nlm-.nih.gov.

Nucleic Acid Construct

The present invention also provides a nucleic acid construct encoding a chimeric receptor of the invention.

A nucleic acid construct encoding a FabCAR (FIG. 6A) may have the structure:

VH-CH-spacer-TM-endo-coexpr-VL-CL or
VL-CL-spacer-TM-endo-coexpr-VH-CH in which:

VH is a nucleic acid sequence encoding a heavy chain variable region;

CH is a nucleic acid sequence encoding a heavy chain constant region spacer is a nucleic acid encoding a spacer;

TM is a a nucleic acid sequence encoding a transmembrane domain;

endo is a nucleic acid sequence encoding an endodomain;

coexpr is a nucleic acid sequence enabling co-expression of the first and second polypeptides;

VL is a nucleic acid sequence encoding a light chain variable region; and

CL is a nucleic acid sequence encoding a light chain constant region.

For both structures mentioned above, nucleic acid sequences encoding the two polypeptides may be in either order in the construct.

There is also provided a nucleic acid construct encoding an OR gate, which comprises two of more CARs, at least one of which is a FabCAR according to the present invention.

A nucleic acid construct encoding a double OR gate may have the structure:

VH-CH-spacer1-TM1-endo1-coexpr1-VL-CL-coexpr2-AgBD-spacer2-TM2-endo2; or

VL-CL-spacer-TM1-endo1-coexpr1-VH-CH-coexpr2-AgBD-spacer2-TM2-endo2 in which:

VH is a nucleic acid sequence encoding a heavy chain variable region of the first CAR;

CH is a nucleic acid sequence encoding a heavy chain constant region of the first CAR;

Spacer 1 is a nucleic acid sequence encoding a spacer of the first CAR;

TM1 is a a nucleic acid sequence encoding a transmembrane domain of the first CAR;

Endo1 is a nucleic acid sequence encoding an endodomain of the first CAR;

Coexpr1 and coexpr2, which my be the same or different, are nucleic acid sequences enabling co-expression of the first and second polypeptides of the first CAR; and the first and second CARs;

VL is a nucleic acid sequence encoding a light chain variable region of the first CAR;

CL is a nucleic acid sequence encoding a light chain constant region of the first CAR;

AgBD is a nucleic acid sequence encoding an antigen binding domain of the second CAR;

Spacer2 is a nucleic acid sequence encoding a spacer of the second CAR;

TM2 is a a nucleic acid sequence encoding a transmembrane domain of the second CAR; and Endo2 is a nucleic acid sequence encoding an endodomain of the second CAR.

The antigen-binding domain of the second CAR may, for example, be an scFv or a dAb.

For both structures mentioned above, nucleic acid sequences encoding the two polypeptides of the first CAR; and the nucleic acid sequences encoding the first and second CARs may be in any order in the construct.

There is also provided a nucleic acid construct encoding a triple OR gate, which comprises three CARs, one of which is a FabCAR according to the present invention.

A nucleic acid construct encoding a triple OR gate may have the structure:

VH-CH-spacer1-TM1-endo1-coexpr1-VL-CL-coexpr2-AgBD2-spacer2-TM2-endo2-coexpr3-AgBD3-spacer3-TM3-endo3; or VL-CL-spacer1-TM1-endo1-coexpr1-VH-CH-coexpr2-AgBD2-spacer2-TM2-endo2-coexpr3-AgBD3-spacer3-TM3 in which:

VH is a nucleic acid sequence encoding a heavy chain variable region of the first CAR;

CH is a nucleic acid sequence encoding a heavy chain constant region of the first CAR;

Spacer 1 is a nucleic acid sequence encoding a spacer of the first CAR;

TM1 is a nucleic acid sequence encoding a transmembrane domain of the first CAR;

Endo1 is a nucleic acid sequence encoding an endodomain of the first CAR;

Coexpr1, coexpr2 and coexpr3, which my be the same or different, are nucleic acid sequences enabling co-expression of the first and second polypeptides of the first CAR; and the first, second and third CARs;

VL is a nucleic acid sequence encoding a light chain variable region of the first CAR;

CL is a nucleic acid sequence encoding a light chain constant region of the first CAR;

AgBD2 is a nucleic acid sequence encoding an antigen binding domain of the second CAR;

Spacer2 is a nucleic acid sequence encoding a spacer of the second CAR;

TM2 is a a nucleic acid sequence encoding a transmembrane domain of the second CAR;

Endo2 is a nucleic acid sequence encoding an endodomain of the second CAR;

AgBD3 is a nucleic acid sequence encoding an antigen binding domain of the third CAR;

Spacer3 is a nucleic acid sequence encoding a spacer of the third CAR;

TM3 is a a nucleic acid sequence encoding a transmembrane domain of the third CAR; and Endo3 is a nucleic acid sequence encoding an endodomain of the third CAR;

The antigen-binding domain of the second and third CARs may, for example, be an scFv or a dAb. In particular, one CAR may have a dAb antigen-binding domain and the other may have an scFv antigen binding domain.

Figure 7:
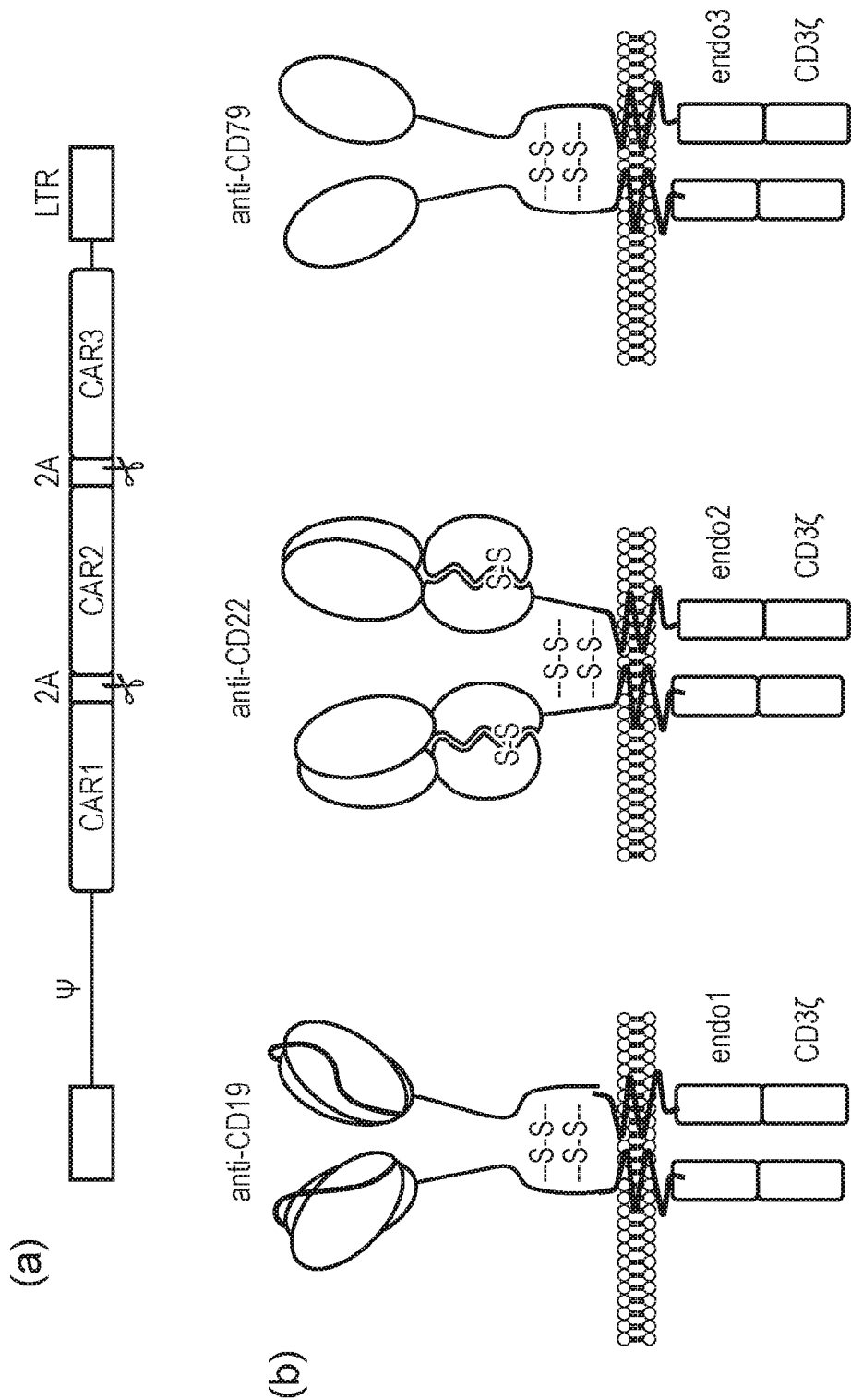

In particular, the construct may be as illustrated in FIG. 7a. The construct may encode three CARs as illustrated in FIG. 7b, namely a FabCAR against CD22; a dAb CAR against CD79 and an scFV CAR against CD19.

As used herein, the terms "polynucleotide", "nucleotide", and "nucleic acid" are intended to be synonymous with each other.

It will be understood by a skilled person that numerous different polynucleotides and nucleic acids can encode the same polypeptide as a result of the degeneracy of the genetic code. In addition, it is to be understood that skilled persons may, using routine techniques, make nucleotide substitutions that do not affect the polypeptide sequence encoded by the polynucleotides described here to reflect the codon usage of any particular host organism in which the polypeptides are to be expressed.

Nucleic acids according to the invention may comprise DNA or RNA. They may be single-stranded or double-stranded. They may also be polynucleotides which include within them synthetic or modified nucleotides. A number of different types of modification to oligonucleotides are known in the art. These include methylphosphonate and phosphorothioate backbones, addition of acridine or polylysine chains at the 3' and/or 5' ends of the molecule. For the purposes of the use as described herein, it is to be understood that the polynucleotides may be modified by any method available in the art. Such modifications may be carried out in order to enhance the in vivo activity or life span of polynucleotides of interest.

The terms "variant", "homologue" or "derivative" in relation to a nucleotide sequence include any substitution of, variation of, modification of, replacement of, deletion of or addition of one (or more) nucleic acid from or to the sequence.

In the structure above, "coexpr" is a nucleic acid sequence enabling co-expression of two polypeptides as separate entities. It may be a sequence encoding a cleavage site, such that the nucleic acid construct produces both polypeptides, joined by a cleavage site(s). The cleavage site may be self-cleaving, such that when the polypeptide is produced, it is immediately cleaved into individual peptides without the need for any external cleavage activity.

The cleavage site may be any sequence which enables the two polypeptides to become separated.

The term "cleavage" is used herein for convenience, but the cleavage site may cause the peptides to separate into individual entities by a mechanism other than classical cleavage. For example, for the Foot-and-Mouth disease virus (FMDV) 2A self-cleaving peptide (see below), various models have been proposed for to account for the "cleavage" activity: proteolysis by a host-cell proteinase, autoproteolysis or a translational effect (Donnelly et al (2001) J. Gen. Virol. 82:1027-1041). The exact mechanism of such "cleavage" is not important for the purposes of the present invention, as long as the cleavage site, when positioned between nucleic acid sequences which encode proteins, causes the proteins to be expressed as separate entities.

The cleavage site may, for example be a furin cleavage site, a Tobacco Etch Virus (TEV) cleavage site or encode a self-cleaving peptide.

A 'self-cleaving peptide' refers to a peptide which functions such that when the polypeptide comprising the proteins and the self-cleaving peptide is produced, it is immediately "cleaved" or separated into distinct and discrete first and second polypeptides without the need for any external cleavage activity.

The self-cleaving peptide may be a 2A self-cleaving peptide from an aphtho- or a cardiovirus. The primary 2A/2B cleavage of the aptho- and cardioviruses is mediated by 2A "cleaving" at its own C-terminus. In apthoviruses, such as foot-and-mouth disease viruses (FMDV) and equine rhinitis A virus, the 2A region is a short section of about 18 amino acids, which, together with the N-terminal residue of protein 2B (a conserved proline residue) represents an autonomous element capable of mediating "cleavage" at its own C-terminus (Donelly et al (2001) as above).

"2 Å-like" sequences have been found in picornaviruses other than aptho- or cardioviruses, 'picornavirus-like' insect viruses, type C rotaviruses and repeated sequences within *Trypanosoma* spp and a bacterial sequence (Donnelly et al (2001) as above).

The cleavage site may comprise the 2 Å-like sequence shown as SEQ ID No.92 (RAEGRGSLLTCGDVEENPGP).

Vector

The present invention also provides a vector, or kit of vectors, which comprises one or more nucleic acid sequence(s) encoding a chimeric receptor according to the invention. Such a vector may be used to introduce the nucleic acid sequence(s) into a host cell so that it expresses a chimeric polypeptide according to the first aspect of the invention.

The vector may, for example, be a plasmid or a viral vector, such as a retroviral vector or a lentiviral vector, or a transposon based vector or synthetic mRNA.

The vector may be capable of transfecting or transducing a T cell or a NK cell.

Cell

The present invention provides a cell which comprises a chimeric antigen receptor of the invention. The cell may comprise two of more CARs, for example it may comprise a double or triple or gate as described above.

The cell may comprise a nucleic acid or a vector of the present invention.

The cell may be a cytolytic immune cell such as a T cell or an NK cell.

T cells or T lymphocytes are a type of lymphocyte that play a central role in cell-mediated immunity. They can be distinguished from other lymphocytes, such as B cells and natural killer cells (NK cells), by the presence of a T-cell receptor (TCR) on the cell surface. There are various types of T cell, as summarised below.

Helper T helper cells (TH cells) assist other white blood cells in immunologic processes, including maturation of B cells into plasma cells and memory B cells, and activation of cytotoxic T cells and macrophages. TH cells express CD4 on their surface. TH cells become activated when they are presented with peptide antigens by MHC class II molecules on the surface of antigen presenting cells (APCs). These cells can differentiate into one of several subtypes, including TH1, TH2, TH3, TH17, Th9, or TFH, which secrete different cytokines to facilitate different types of immune responses.

Cytolytic T cells (TC cells, or CTLs) destroy virally infected cells and tumor cells, and are also implicated in transplant rejection. CTLs express the CD8 at their surface.

These cells recognize their targets by binding to antigen associated with MHC class I, which is present on the surface of all nucleated cells. Through IL-10, adenosine and other molecules secreted by regulatory T cells, the CD8+cells can be inactivated to an anergic state, which prevent autoimmune diseases such as experimental autoimmune encephalomyelitis.

Memory T cells are a subset of antigen-specific T cells that persist long-term after an infection has resolved. They quickly expand to large numbers of effector T cells upon re-exposure to their cognate antigen, thus providing the immune system with "memory" against past infections. Memory T cells comprise three subtypes: central memory T cells (TCM cells) and two types of effector memory T cells (TEM cells and TEMRA cells). Memory cells may be either CD4+ or CD8+. Memory T cells typically express the cell surface protein CD45RO.

Regulatory T cells (Treg cells), formerly known as suppressor T cells, are crucial for the maintenance of immunological tolerance. Their major role is to shut down T cell-mediated immunity toward the end of an immune reaction and to suppress auto-reactive T cells that escaped the process of negative selection in the thymus.

Two major classes of CD4+Treg cells have been described—naturally occurring Treg cells and adaptive Treg cells.

Naturally occurring Treg cells (also known as CD4+ CD25+FoxP3+Treg cells) arise in the thymus and have been linked to interactions between developing T cells with both myeloid (CD11c+) and plasmacytoid (CD123+) dendritic cells that have been activated with TSLP. Naturally occurring Treg cells can be distinguished from other T cells by the presence of an intracellular molecule called FoxP3. Mutations of the FOXP3 gene can prevent regulatory T cell development, causing the fatal autoimmune disease IPEX.

Adaptive Treg cells (also known as Tr1 cells or Th3 cells) may originate during a normal immune response.

The cell may be a Natural Killer cell (or NK cell). NK cells form part of the innate immune system. NK cells provide rapid responses to innate signals from virally infected cells in an MHC independent manner NK cells (belonging to the group of innate lymphoid cells) are defined as large granular lymphocytes (LGL) and constitute the third kind of cells differentiated from the common lymphoid progenitor generating B and T lymphocytes. NK cells are known to differentiate and mature in the bone marrow, lymph node, spleen, tonsils and thymus where they then enter into the circulation.

The cells of the invention may be any of the cell types mentioned above.

T or NK cells according to the first aspect of the invention may either be created ex vivo either from a patient's own peripheral blood (1st party), or in the setting of a haematopoietic stem cell transplant from donor peripheral blood (2nd party), or peripheral blood from an unconnected donor (3rd party).

Alternatively, T or NK cells according to the first aspect of the invention may be derived from ex vivo differentiation of inducible progenitor cells or embryonic progenitor cells to T or NK cells. Alternatively, an immortalized T-cell line which retains its lytic function and could act as a therapeutic may be used.

In all these embodiments, chimeric polypeptide-expressing cells are generated by introducing DNA or RNA coding for the chimeric polypeptide by one of many means including transduction with a viral vector, transfection with DNA or RNA.

The cell of the invention may be an ex vivo T or NK cell from a subject. The T or NK cell may be from a peripheral blood mononuclear cell (PBMC) sample. T or NK cells may be activated and/or expanded prior to being transduced with nucleic acid encoding the molecules providing the chimeric polypeptide according to the first aspect of the invention, for example by treatment with an anti-CD3 monoclonal antibody.

The T or NK cell of the invention may be made by:
(i) isolation of a T or NK cell-containing sample from a subject or other sources listed above; and
(ii) transduction or transfection of the T or NK cells with one or more a nucleic acid sequence(s) encoding a chimeric polypeptide.

The T or NK cells may then by purified, for example, selected on the basis of expression of the antigen-binding domain of the antigen-binding polypeptide.

Pharmaceutical Composition

The present invention also relates to a pharmaceutical composition containing a plurality of cells according to the invention.

The pharmaceutical composition may additionally comprise a pharmaceutically acceptable carrier, diluent or excipient. The pharmaceutical composition may optionally comprise one or more further pharmaceutically active polypeptides and/or compounds. Such a formulation may, for example, be in a form suitable for intravenous infusion.

Method of Treatment

The present invention provides a method for treating and/or preventing a disease which comprises the step of administering the cells of the present invention (for example in a pharmaceutical composition as described above) to a subject.

A method for treating a disease relates to the therapeutic use of the cells of the present invention. Herein the cells may be administered to a subject having an existing disease or condition in order to lessen, reduce or improve at least one symptom associated with the disease and/or to slow down, reduce or block the progression of the disease.

The method for preventing a disease relates to the prophylactic use of the cells of the present invention. Herein such cells may be administered to a subject who has not yet contracted the disease and/or who is not showing any symptoms of the disease to prevent or impair the cause of the disease or to reduce or prevent development of at least one symptom associated with the disease. The subject may have a predisposition for, or be thought to be at risk of developing, the disease.

The method may involve the steps of:
(i) isolating a T or NK cell-containing sample;
(ii) transducing or transfecting such cells with a nucleic acid sequence or vector provided by the present invention;
(iii) administering the cells from (ii) to a subject.

The T or NK cell-containing sample may be isolated from a subject or from other sources, for example as described above. The T or NK cells may be isolated from a subject's own peripheral blood (1st party), or in the setting of a haematopoietic stem cell transplant from donor peripheral blood (2nd party), or peripheral blood from an unconnected donor (3rd party).

The present invention provides a chimeric polypeptide-expressing cell of the present invention for use in treating and/or preventing a disease.

The invention also relates to the use of a chimeric polypeptide-expressing cell of the present invention in the manufacture of a medicament for the treatment and/or prevention of a disease.

The disease to be treated and/or prevented by the methods of the present invention may be a cancerous disease, such as bladder cancer, breast cancer, colon cancer, endometrial cancer, kidney cancer (renal cell), leukaemia, lung cancer, melanoma, non-Hodgkin lymphoma, pancreatic cancer, prostate cancer and thyroid cancer.

The disease may be Multiple Myeloma (MM), B-cell Acute Lymphoblastic Leukaemia (B-ALL), Chronic Lymphocytic Leukaemia (CLL), Neuroblastoma, T-cell acute Lymphoblastic Leukaema (T-ALL) or diffuse large B-cell lymphoma (DLBCL).

The cells of the present invention may be capable of killing target cells, such as cancer cells. The target cell may be characterised by the presence of a tumour secreted ligand or chemokine ligand in the vicinity of the target cell. The target cell may be characterised by the presence of a soluble ligand together with the expression of a tumour-associated antigen (TAA) at the target cell surface.

The cells and pharmaceutical compositions of present invention may be for use in the treatment and/or prevention of the diseases described above.

Further Aspects

The present invention also provides a new CD22-binding antibody, termed 9 Å8-1. The VH, VL and CDR sequences of 9 Å8 are shown in Table 1 above.

This antibody shows particularly good efficacy in a CAR. For example, as shown in Example 3 below, 9 Å8-1 in a FabCAR format showed improved target cell killing and cytokine release that an equivalent CAR with an alternative CD22 binder, 3B4.

The present invention also provides the aspects summarised in the following numbered paragraphs.

1. An antigen-binding domain which comprises:
a) a heavy chain variable region (VH) having complementarity determining regions (CDRs) with the following sequences:

```
                                       (SEQ ID No. 93)
    CDR1 - NFAMA (SEQ ID No. 94)
    CDR2 - SISTGGGNTYYRDSVKG (SEQ ID No. 95)
    CDR3 - QRNYYDGSYDYEGYTMDA;
``` and
b) a light chain variable region (VL) having complementarity determining regions (CDRs) with the following sequences:

```
                                       (SEQ ID No. 96)
        CDR1 - RSSQDIGNYLT (SEQ ID No. 97)
        CDR2 - GAIKLED (SEQ ID No. 98)
        CDR3 - LQSIQYP
```

2. An antigen-binding domain according to paragraph 1, which comprises a VH domain having the sequence shown as SEQ ID No. 65; and a VL domain having the sequence shown as SEQ ID No. 66.

3. An antibody which comprises an antigen-binding domain according to paragraph 1 or 2.

4. An antibody-drug conjugate (ADC) or bispecific T-cell engager (BiTE) which comprises an antibody according to paragraph 3.

5. A chimeric antigen receptor (CAR) which comprises an antigen-binding domain according to paragraph 1 or 2.

6. A CAR according to paragraph 5, which is a FabCAR.

A CAR according to paragraph 5, which is an scFv CAR.

8. A nucleic acid sequence which encodes an antigen-binding domain according to paragraph 1 or 2, and antibody according to paragraph 3, an ADC or BiTE according to paragraph 4, or a CAR according to any of paragraphs 5 to 7.

9. A nucleic acid sequence according to claim 8 which encodes a CAR according to any of paragraphs 5 to 7 and has a GC content of at least 60%.

10. A nucleic acid sequence according to claim 8 which encodes a CAR according to any of paragraphs 5 to 7 and has a GC content of about 64%.

11. A nucleic acid sequence according to any of claims 8 to 10 which comprises an elongation factor-1 alpha (EF1α) promoter.

12. A nucleic acid construct which comprises a first nucleic acid sequence according to any of claims 8 to 11 encoding a CAR according to any of paragraphs 5 to 7 and a second nucleic acid sequence encoding an anti-CD19 CAR.

13. A nucleic acid construct according to claim 12, wherein the antigen binding domain of the anti-CD19 CAR comprises a) a heavy chain variable region (VH) having complementarity determining regions (CDRs) with the following sequences:

```
                        (SEQ ID No. 69)
    CDR1 - GYAFSSS;

(SEQ ID No. 70)
    CDR2 - YPGDED (SEQ ID No. 71)
    CDR3 - SLLYGDYLDY;
``` and b) a light chain variable region (VL) having CDRs with the following sequences:

```
                        (SEQ ID No. 72)
    CDR1 - SASSSVSYMH;

(SEQ ID No. 73)
    CDR2 - DTSKLAS (SEQ ID No. 74)
    CDR3 - QQWNINPLT.
```

14. A nucleic acid construct according to claim 13, wherein the antigen-binding domain of the anti-CD19 CAR comprises a VH domain as shown in SEQ ID No. 75 and a VL domain as shown as SEQ ID No. 76.

15. A nucleic acid construct according to any of claims 12 to 14, wherein the anti-CD22 CAR is in a Fab format, the nucleic acid construct having the general structure:

VH-CH-spacer1-TM1-endo1-coexpr1-VL-CL-coexpr2-AgBD-spacer2-TM2-endo2;

VL-CL-spacer-TM1-endo1-coexpr1-VH-CH-coexpr2-AgBD-spacer2-TM2-endo2;

AgBD-spacer2-TM2-endo2-VH-CH-spacer1-TM1-endo1-coexpr2-VL-CL;

AgBD-spacer2-TM2-endo2-coexpr1-VL-CL-spacer-TM1-endo1-coexpr2-VH-CH

VL-CL-coexpr1-VH-CH-spacer1-TM1-endo1--coexpr2-AgBD-spacer2-TM2-endo2;

VH-CH-coexpr1-VL-CL-spacer-TM1-endo1-coexpr2-AgBD-spacer2-TM2-endo2;

AgBD-spacer2-TM2-endo2-VL-CL-coexpr2-VH-CH-spacer1-TM1-endo1; or

AgBD-spacer2-TM2-endo2-coexpr1-VH-CH-coexpr2-VL-CL-spacer-TM1-endo1 in which:

VH is a nucleic acid sequence encoding a heavy chain variable region of the first CAR;

CH is a nucleic acid sequence encoding a heavy chain constant region of the first CAR;

Spacer 1 is a nucleic acid sequence encoding a spacer of the first CAR;

TM1 is a a nucleic acid sequence encoding a transmembrane domain of the first CAR;

Endo1 is a nucleic acid sequence encoding an endodomain of the first CAR;

Coexpr1 and coexpr2, which my be the same or different, are nucleic acid sequences enabling co-expression of the first and second polypeptides of the first CAR; and the second CAR;

VL is a nucleic acid sequence encoding a light chain variable region of the first CAR;

CL is a nucleic acid sequence encoding a light chain constant region of the first CAR;

AgBD is a nucleic acid sequence encoding an antigen binding domain of the second CAR;

Spacer2 is a nucleic acid sequence encoding a spacer of the second CAR;

TM2 is a a nucleic acid sequence encoding a transmembrane domain of the second CAR; and Endo2 is a nucleic acid sequence encoding an endodomain of the second CAR.

16. A nucleic acid construct according to any of claims 12 to 14, wherein the anti-CD22 CAR is in an ScFv format, the nucleic acid construct having the general structure:

AgBD1-spacer1-TM1-endo1-coexpr-AgBD2-spacer2-TM2-endo2; or AgBD2-spacer2-TM2-endo2-coexpr-AgBD1-spacer1-TM1-endo1

In which:

AgBD1 is a nucleic acid sequence encoding an antigen binding domain of the first CAR;

Spacer1 is a nucleic acid sequence encoding a spacer of the first CAR;

TM1 is a a nucleic acid sequence encoding a transmembrane domain of the first CAR; and Endo1 is a nucleic acid sequence encoding an endodomain of the first CAR.

Coexpr is a nucleic acid sequence enabling co-expression of the first and second CARs;

AgBD2 is a nucleic acid sequence encoding an antigen binding domain of the second CAR;

Spacer2 is a nucleic acid sequence encoding a spacer of the second CAR;

TM2 is a a nucleic acid sequence encoding a transmembrane domain of the second CAR; and Endo2 is a nucleic acid sequence encoding an endodomain of the second CAR.

17. A vector which comprises a nucleic acid sequence according to any of paragraphs 8 to 11 or a nucleic acid construct according to any of paragraphs 12 to 16.

18. A kit of vectors which comprises a first vector comprising a first nucleic acid sequence as defined in any of paragraphs 12 to 16; and a second vector comprising a second nucleic acid sequence as defined in any of paragraphs 12 to 16.

19. A vector or kit of vectors according to paragraph 17 or 18 which is/are retroviral vector(s).

20. A vector or kit of vectors according to paragraph 17 or 18 which is/are lentiviral vector(s).

21. A cell which expresses a CAR according to any of paragraphs 5 to 7.

22. A cell which co-expresses a first CAR according to any of paragraphs 5 to 7 and a second CAR which is an anti-CD19 CAR.

23. A cell according to claim 22, wherein the antigen binding domain of the anti-CD19 CAR comprises
a) a heavy chain variable region (VH) having complementarity determining regions (CDRs) with the following sequences:

```
                          (SEQ ID No. 69)
    CDR1 - GYAFSSS;

(SEQ ID No. 70)
    CDR2 - YPGDED (SEQ ID No. 71)
    CDR3 - SLLYGDYLDY;
``` and
b) a light chain variable region (VL) having CDRs with the following sequences:

```
                          (SEQ ID No. 72)
    CDR1 - SASSSVSYMH;

(SEQ ID No. 73)
    CDR2 - DTSKLAS (SEQ ID No. 74)
    CDR3 - QQWNINPLT.
```

24. A cell according to paragraph 23, wherein the antigen-binding domain of the anti-CD19 CAR comprises a VH domain as shown in SEQ ID No. 75 and a VL domain as shown in SEQ ID No. 76.

25. A method for making a cell according to any of paragraphs 21 to 24, which comprises the step of introducing a CAR-encoding nucleic acid sequence according to any of paragraphs 8 to 11; a nucleic-acid construct according to any of paragraphs 12 to 16 or a vector or kit of vectors according to any of paragraphs 17 to 20 into a cell ex vivo.

26. A pharmaceutical composition which comprises a plurality of cells according to any of paragraphs 21 to 24, together with a pharmaceutically acceptable carrier, diluent or excipient.

27. A method for treating cancer which comprises the step of administering a pharmaceutical composition according to paragraph 26 to a subject.

28. A method according to paragraph 27, wherein the cancer is a B-cell leukemia or lymphoma.

29. A cell according to any of paragraphs 21 to 24 for use in treating a cancer.

30. The use of a cell according to any of paragraphs 21 to 24 in the manufacture of a pharmaceutical composition for treating cancer.

General features of, for example, chimeric antigen receptors, nucleic acid sequences and constructs, vectors, cells, pharmaceutical compositions and method of making and using cells described in the preceding sections also apply to the corresponding components described in the paragraphs above.

The present invention also provides a new CD22-binding antibody, termed 1G3-4. The VH, VL and CDR sequences of 1G3-4 are shown in Table 1 above.

This antibody shows particularly good efficacy in a CAR. For example, as shown in Example 3 below, 9 Å8-1 in a FabCAR format showed improved target cell killing and cytokine release that an equivalent CAR with an alternative CD22 binder, 3B4.

The present invention also provides the aspects summarised in the following numbered paragraphs.

A1. An antigen-binding domain which comprises:
a) a heavy chain variable region (VH) having complementarity determining regions (CDRs) with the following sequences:

```
                          (SEQ ID No. 101)
    CDR1 - TSGMGVG (SEQ ID No. 102)
    CDR2 - NIWWDDDKNYNPSLKN (SEQ ID No. 103)
    CDR3 - IAHYFDGYYYVMDV;
``` and
b) a light chain variable region (VL) having complementarity determining regions (CDRs) with the following sequences:

```
                          (SEQ ID No. 104)
    CDR1 - LASGGISNDLA (SEQ ID No. 105)
    CDR2 - AASRLQD (SEQ ID No. 106)
    CDR3 - QQSYKYPY
```

A2. An antigen-binding domain according to paragraph A1, which comprises a VH domain having the sequence shown as SEQ ID No. 99; and a VL domain having the sequence shown as SEQ ID No. 100.

A3. An antibody which comprises an antigen-binding domain according to paragraph A1 or A2.

A4. An antibody-drug conjugate (ADC) or bispecific T-cell engager (BiTE) which comprises an antibody according to paragraph A3.

A5. A chimeric antigen receptor (CAR) which comprises an antigen-binding domain according to paragraph A1 or A2.

A6. A CAR according to paragraph A5, which is a FabCAR.

A7. A nucleic acid sequence which encodes an antigen-binding domain according to paragraph A1 or A2, and antibody according to paragraph A3, an ADC or BiTE according to paragraph A4, or a CAR according to paragraph A5 or A6.

A8. A vector which comprises a nucleic acid sequence according to paragraph A7.

A9. A cell which expresses a CAR according to paragraph A5 or A6.

A10. A method for making a cell according to paragraph A9, which comprises the step of introducing a CAR-encoding nucleic acid sequence according to paragraph A7 into a cell.

A11. A pharmaceutical composition which comprises a plurality of cells according to paragraph A9, together with a pharmaceutically acceptable carrier, diluent or excipient.

A12. A method for treating cancer which comprises the step of administering a pharmaceutical composition according to paragraph A11 to a subject.

A13. A method according to paragraph A12, wherein the cancer is a B-cell leukemia or lymphoma.

A14. A cell according to paragraph A9 for use in treating a cancer.

A15. The use of a cell according to paragraph A9 in the manufacture of a pharmaceutical composition for treating cancer.

B1. An antigen-binding domain which comprises:

ai) a heavy chain variable region (VH) having complementarity determining regions (CDRs) with the following sequences:

```
                                        (SEQ ID No. 113)
        CDR1 - SYTVS (SEQ ID No. 114)
        CDR2 - AISSGGSTYYNSALKS (SEQ ID No. 115)
        CDR3 - YTTDSGFDY;
``` and bi) a light chain variable region (VL) having complementarity determining regions (CDRs) with the following sequences:

```
                                        (SEQ ID No. 116)
        CDR1 - KASQNINKNLD (SEQ ID No. 117)
        CDR2 - FTNNLQT (SEQ ID No. 118)
        CDR3 - YQYNSGWT;
``` or aii) a heavy chain variable region (VH) having complementarity determining regions (CDRs) with the following sequences:

```
                                        (SEQ ID No. 119)
        CDR1 - DYNMA (SEQ ID No. 120)
        CDR2 - TISYDGTNTYYRDSVKG (SEQ ID No. 121)
        CDR3 - QDSSYVYLSWFAY;
``` and bii) a light chain variable region (VL) having complementarity determining regions (CDRs) with the following sequences:

```
                                        (SEQ ID No. 122)
        CDR1 - RASEDIYNGLT (SEQ ID No. 123)
        CDR2 - NANCLHT (SEQ ID No. 124)
        CDR3 - QQYYNYPWT;
``` or aiii) a heavy chain variable region (VH) having complementarity determining regions (CDRs) with the following sequences:

```
                                        (SEQ ID No. 125)
        CDR1 - SYTVS (SEQ ID No. 126)
        CDR2 - AISSGGNTYYNSGLKS (SEQ ID No. 127)
        CDR3 - YAQIRGKDY;
``` and biii) a light chain variable region (VL) having complementarity determining regions (CDRs) with the following sequences:

```
                                        (SEQ ID No. 128)
        CDR1 - KASQNINKNLD (SEQ ID No. 129)
        CDR2 - YTHNLQT (SEQ ID No. 130)
        CDR3 - YQYYSGWT.
```

B2. An antigen-binding domain according to paragraph 1, which comprises: i) a VH domain having the sequence shown as SEQ ID No. 107; and a VL domain having the sequence shown as SEQ ID No. 108; or ii) a VH domain having the sequence shown as SEQ ID No. 109; and a VL domain having the sequence shown as SEQ ID No. 110; or iii) a VH domain having the sequence shown as SEQ ID No. 111; and a VL domain having the sequence shown as SEQ ID No. 112.

B3. An antibody which comprises an antigen-binding domain according to paragraph B1 or B2.

B4. An antibody-drug conjugate (ADC) or bispecific T-cell engager (BiTE) which comprises an antibody according to paragraph B3.

B5. A chimeric antigen receptor (CAR) which comprises an antigen-binding domain according to paragraph B1 or B2.

B6. A CAR according to paragraph B5, which is a FabCAR.

B7. A nucleic acid sequence which encodes an antigen-binding domain according to paragraph B1 or B2, and antibody according to paragraph B3, an ADC or BiTE according to paragraph B4, or a CAR according to paragraph B5 or B6.

B8. A vector which comprises a nucleic acid sequence according to paragraph B7.

B9. A cell which expresses a CAR according to paragraph B5 or B6.

B10. A method for making a cell according to paragraph B9, which comprises the step of introducing a CAR-encoding nucleic acid sequence according to paragraph B7 into a cell.

B11. A pharmaceutical composition which comprises a plurality of cells according to paragraph B9, together with a pharmaceutically acceptable carrier, diluent or excipient.

B12. A method for treating cancer which comprises the step of administering a pharmaceutical composition according to paragraph B11 to a subject.

B13. A method according to paragraph B12, wherein the cancer is a B-cell leukemia or lymphoma.

B14. A cell according to paragraph B9 for use in treating a cancer.

B15. The use of a cell according to paragraph B9 in the manufacture of a pharmaceutical composition for treating cancer.

General features of, for example, chimeric antigen receptors, nucleic acid sequences and constructs, vectors, cells, pharmaceutical compositions and method of making and using cells described in the preceding sections also apply to the corresponding components described in the paragraphs above.

The invention will now be further described by way of Examples, which are meant to serve to assist one of ordinary skill in the art in carrying out the invention and are not intended in any way to limit the scope of the invention.

EXAMPLES

A series of experiments were conducted to compare the action of a FabCAR with an scFv CAR based on the same antibody against a target cell expressing an antigen with a bulk extracellular domain (CD22). CAR-T cells expressing the two types of CAR were compared in terms of cytotoxicity and proliferation.

Example 1—FACs-based killing (FBK)

A panel of CARs was created as summarised below and their cytotoxic capability was compared against CD22 expressing target cells.
NT: Non-transduced
10C1-D9 Fab: A FabCAR based on the 10C1 mAb
All CARs had a second generation endodomain comprising CD3 and a 4-1BB co-stimulatory domain.

T-cells were co-cultured with the CD22-expressing SupT1 target cells at a ratio of 1:1. The assay was carried out in a 96-well plate in 0.2 ml total volume using $5 \times 10^4$ transduced T-cells per well and an equal number of target cells. The co-cultures are set up after being normalised for the transduction efficiency. The FBK was carried out after 24h of incubation.

Figure 4:
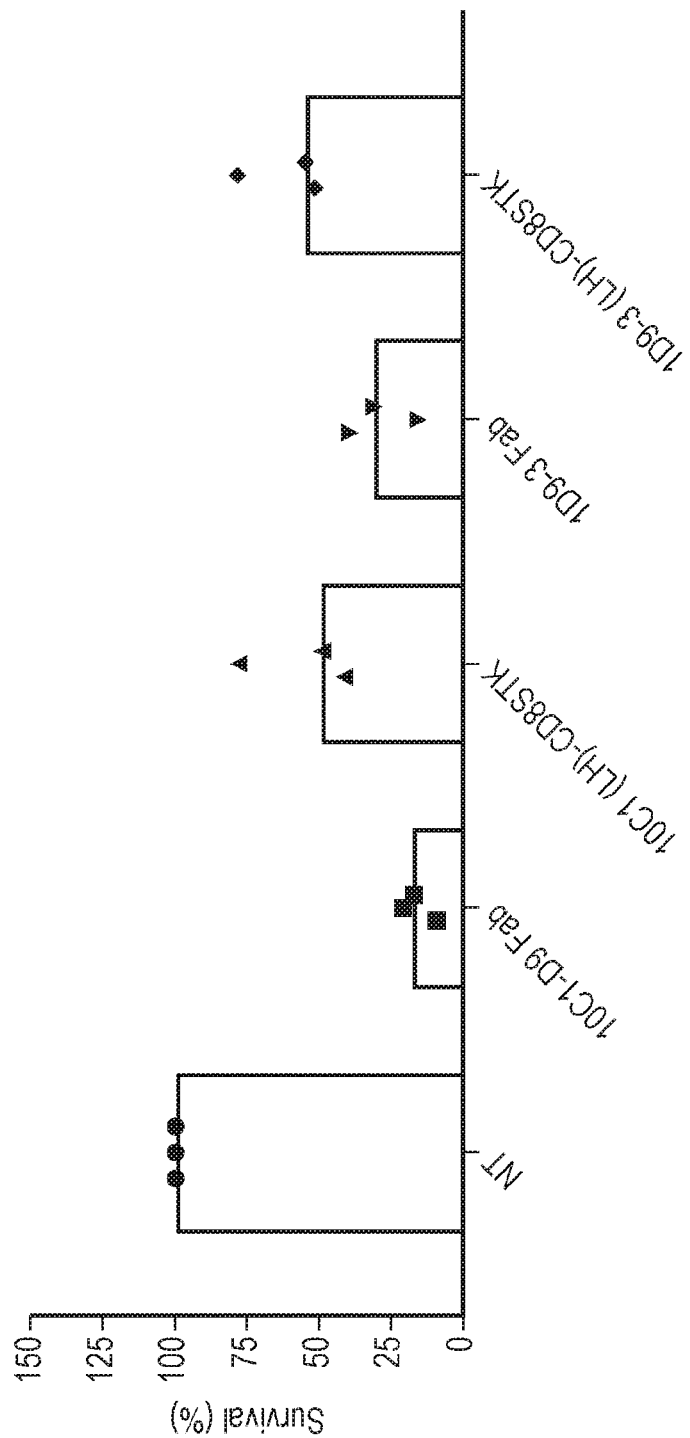
FIG. 4—Graph comparing killing of CD22-expressing target cells by T cells expressing a FabCAR or an scFv CAR. T cells were transduced with viral vectors expressing either a Fab CAR or an scFv CAR having a CD8 stalk spacer. The antigen binding domains were based on the same anti-CD22 antibody, either 10C1 or 1D9-3. T cells were co-cultured with CD22-expressing SupT1 target cells for 24 hours and absolute number of target cells was calculated, and the number in the CAR normalised according to the target number in the non-transduced (NT) condition. The normalised data are expressed as a percentage of target cell survival.

The results of the FBK are shown in FIG. 4. For both CD22 binders tested: 10C1 and 1D9-3, the CAR having a Fab antigen binding domain outperformed the equivalent CAR having an scFv antigen-binding domain in terms of target cell killing.

Example 2—Proliferation Assay (PA)

In order to measure proliferation the same panel of CAR-expressing T cells described in Example 1 were labelled with the dye Cell Trace Violet (CTV), a fluorescent dye which is hydrolysed and retained within the cell. It is excited by the 405 nm (violet) laser and fluorescence can be detected in the pacific blue channel. The CTV dye was reconstituted to 5 mM in DMSO. The T-cells were resuspended at $2 \times 10^6$ cells per ml in PBS, and 1 ul/ml of CTV was added. The T-cells were incubated the CTV for 20 minutes at 37° C. Subsequently, the cells were quenched by adding 5V of complete media. After a 5 minutes incubation, the T-cells were washed and resuspended in 2 ml of complete media. An additional 10 minute incubation at room temperature allowed the occurrence of acetate hydrolysis and retention of the dye.

Labelled T-cells were co-cultured with Raji target cells for four days. The assay was carried out in a 96-well plate in 0.2 ml total volume using $5 \times 10^4$ transduced T-cells per well and an equal number of target cells (ratio 1:1). At the day four time point, the T-cells were analysed by flow cytometry to measure the dilution of the CTV which occurs as the T-cells divide. The number of T-cells present at the end of the co-culture was calculated, and expressed as a fold of proliferation compared to the input number of T cells.

Figure 5:
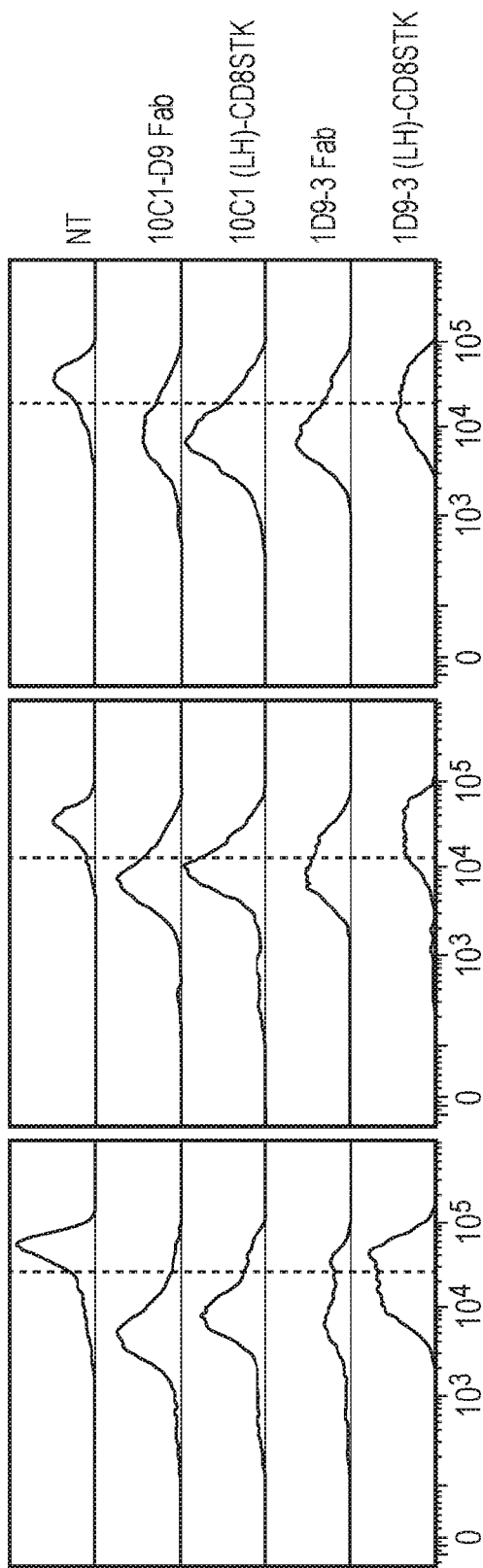
FIG. 5—Histograms showing T-cell proliferation after 4 days co-culture with target cells. CD56-depeleted CAR expressing T cells were co-cultured with Raji target cells and analysed by flow cytometry to measure the dilution of the Cell Trace Violet (CTV) which occurs as the T-cells divide. The T cells labelled with CTV are excited with a 405 nm (violet) laser. The same panel of constructs were tested as for the killing assay, namely: a 10C1 FabCAR; a 10C1 scFv CAR having a CD8 stalk spacer; a 1D9-3 FabCAR and a 1D9-3 scFv CAR having a CD8 stalk spacer.

FIG. 5 shows that for both CD22 binders tested: 10C1 and 1D9-3, T cells expressing the CAR having a Fab antigen binding domain proliferated more than the equivalent CAR having an scFv antigen-binding domain. The area under the curve for both both FabCAR constructs has shifted further along the X-axis compared to the equivalent scFvCAR construct.

Example 3—Investigating the efficacy of the anti-CD22 antibody 9A8-1 in a FabCAR format A panel of CARs was created as summarised below and their cytotoxic capability was compared against CD22 expressing SupT1 target cells.
NT: Non-transduced
3B4: A FabCAR based on the 3B4 mAb
9A8: A FabCAR based on the 9A8-1 mAb
All CARs had a second generation endodomain comprising CD3 and a 4-1BB co-stimulatory domain.

Firstly, the capacity of T-cells expressing the CARs to kill target cells was investigated. T-cells were co-cultured with the CD22-expressing SupT1 target cells at a ratio of 1:4 E:T. A FACS-based killing assay was carried out after 72h of incubation as described below.

Figure 8:
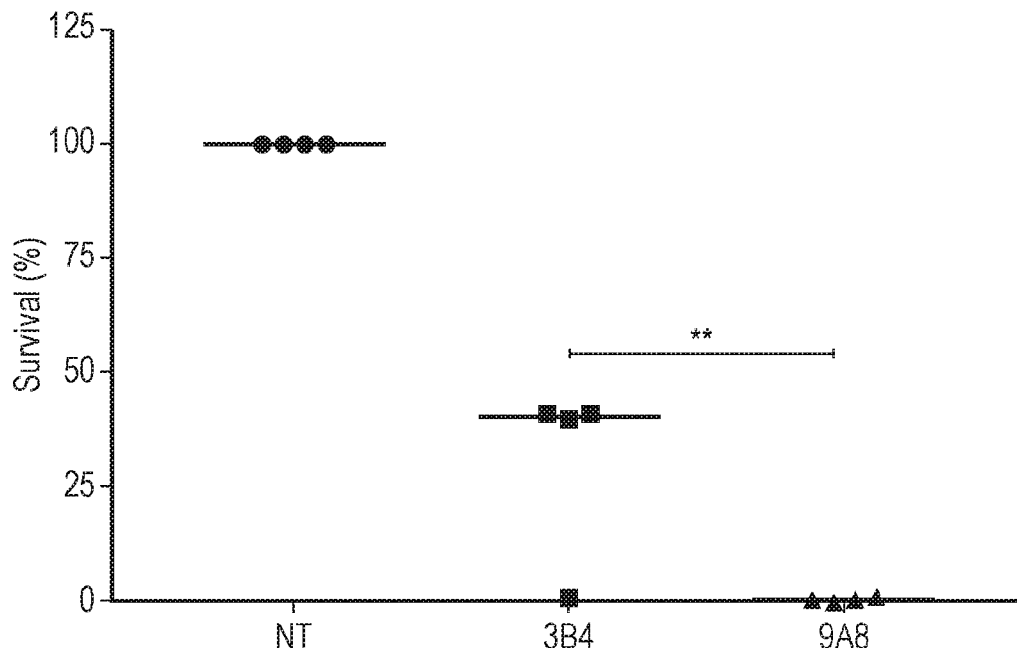
FIG. 8—Graph showing the results of a FACS-based killing assay comparing target cell killing by T cells expressing a FabCAR having a 9A8 antigen-binding domain and T cells expressing a FabCAR having a 3B4 antigen-binding domain FIG. 9—Graph showing the IL-2 release following 72 hours co-culture with SupT1 target cells comparing T cells expressing a FabCAR having a 9A8 antigen-binding domain and T cells expressing a FabCAR having a 3B4 antigen-binding domain FIG. 10—Graph showing the results of a FACS-based killing assay comparing target cell killing by T cells expressing various anti-CD22 FabCARs. Target cells were either non-transduced SupT1 cells (A); or SupT1 cells transduced to express CD22, showing one of three levels of CD22 expression:
B—"ultra-low" undetectable by flow cytometry
C—"low" averaging 255 copies of CD22 per cell
D—"high" averaging 78,916 copies of CD22 per cell FIG. 11—Schematic diagram illustrating the problem of cross-pairing when expressing two FabCARs.

The results of the FBK are shown in FIG. 8. The CAR having a 9 Å8 antigen-binding domain outperformed the equivalent CAR having a 3B4 antigen-binding domain in terms of target cell killing.

Figure 9:
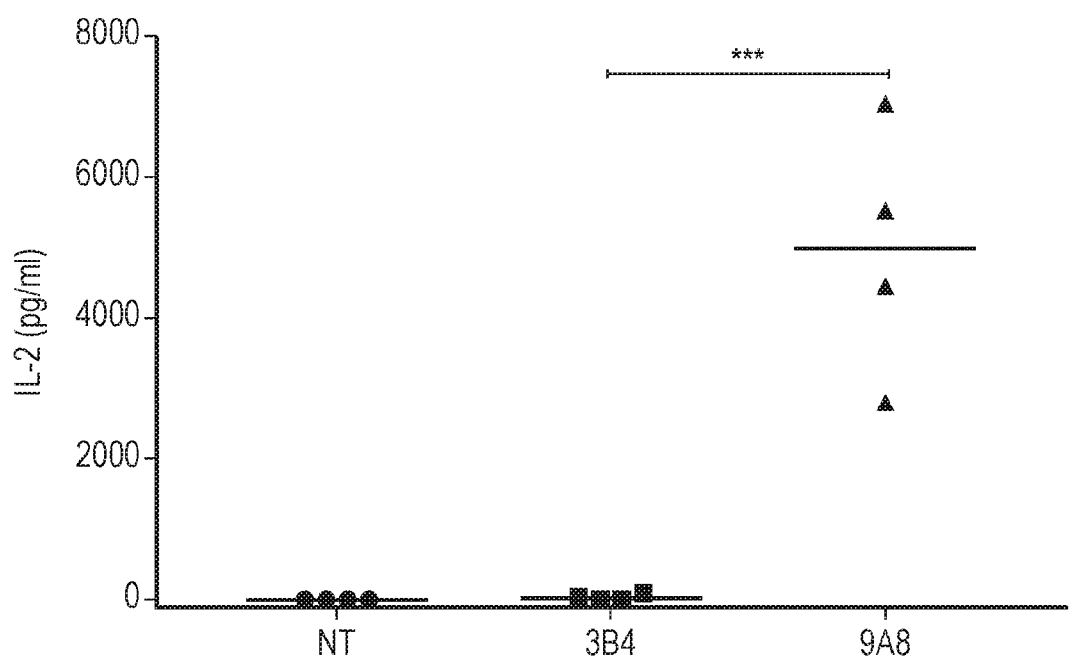

Next, the two CARs were compared in terms of cytokine release. After 72 hr co-culture with CD22-expressing SupT1 target cells, IL-2 expression was investigated by ELISA as described below. The results are shown in FIG. 9. Significantly higher levels of IL-2 release were observed for the CAR having a 9 Å8 antigen-binding domain than the equivalent CAR having a 3B4 antigen-binding domain.

Example 4—Investigating the Efficacy of the Anti-CD22 Antibody 1g3-4 in a FabCAR Format A panel of CARs was created as summarised below:
NT: Non-transduced
Fmc63: An anti-CD19 CAR (negative control)
10C1: An anti-CD22 FabCAR based on the 10C1 mAb
3B4: An anti-CD22 FabCAR based on the 3B4 mAb
7G6: An anti-CD22 FabCAR based on the 7G6 mAb
9F8-2: An anti-CD22 FabCAR based on the 9F8-2 mAb
9A8-1: An anti-CD22 FabCAR based on the 9A8-1 mAb
1G3-4: An anti-CD22 FabCAR based on the 1G3-4 mAb
9F9-6: An anti-CD22 FabCAR based on the 9F9-6 mAb
All CARs had a second generation endodomain comprising CD3 and a 4-1BB co-stimulatory domain.

The capacity of T-cells expressing the CARs to kill SupT1 target cells was investigated. SupT1 cells were either left untransduced (FIG. 10, panel A) or transduced to express CD22. Transduced target cells were sorted into three populations: those with a level of CD22 expression which is undetectable by flow cytometry (FIG. 10, panel B); those with a low level of CD22 expression, averaging 255 copies per cell (FIG. 10, panel C); and those with a high level of CD22 expression, averaging 78,916 copies per cell (FIG. 10, panel D).

T-cells were co-cultured with the CD22-expressing SupT1 target cells at a ratio of 1:4 E:T. A FACS-based killing assay was carried out after 72h of incubation as described below.

Figure 10:
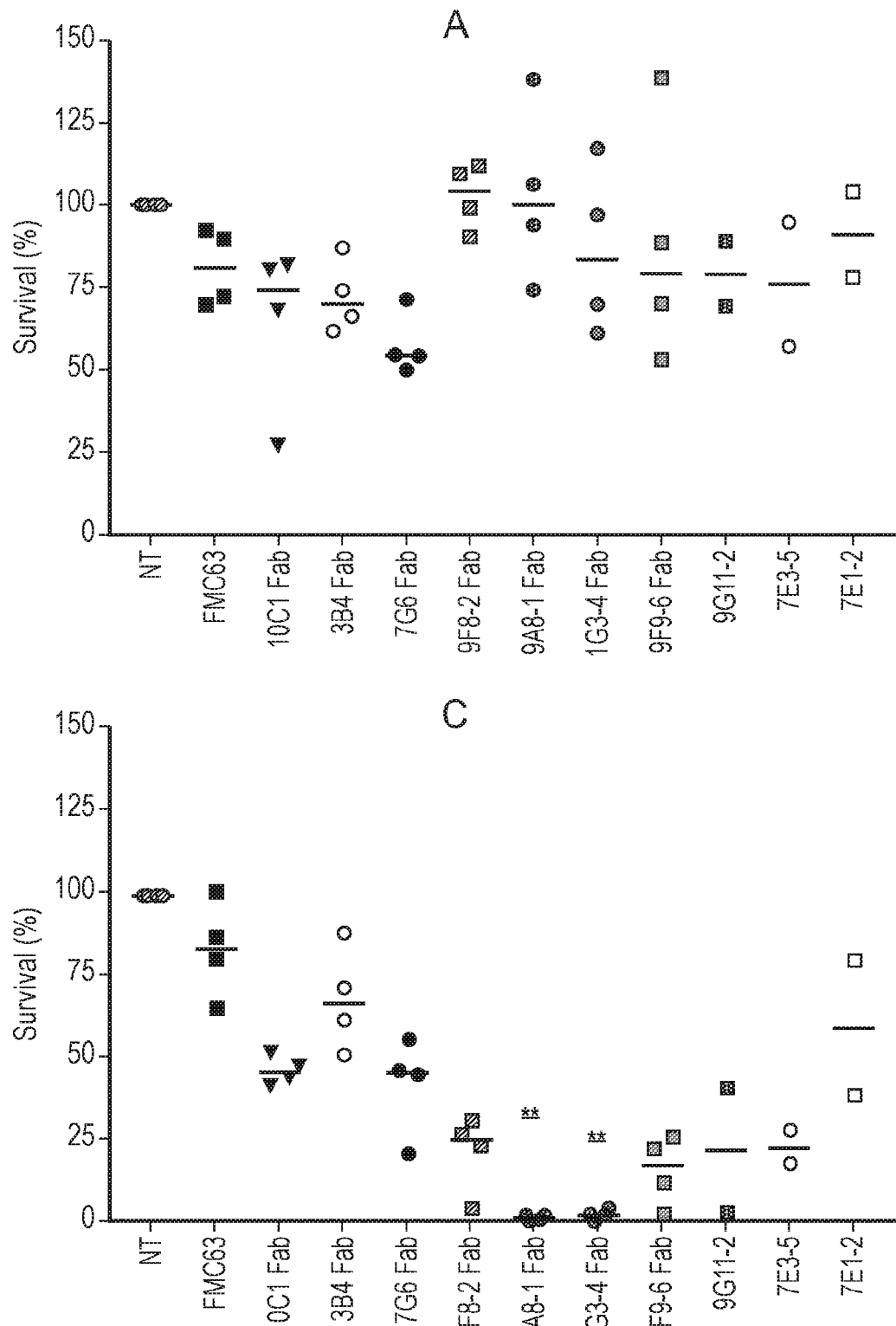
Figure 10:
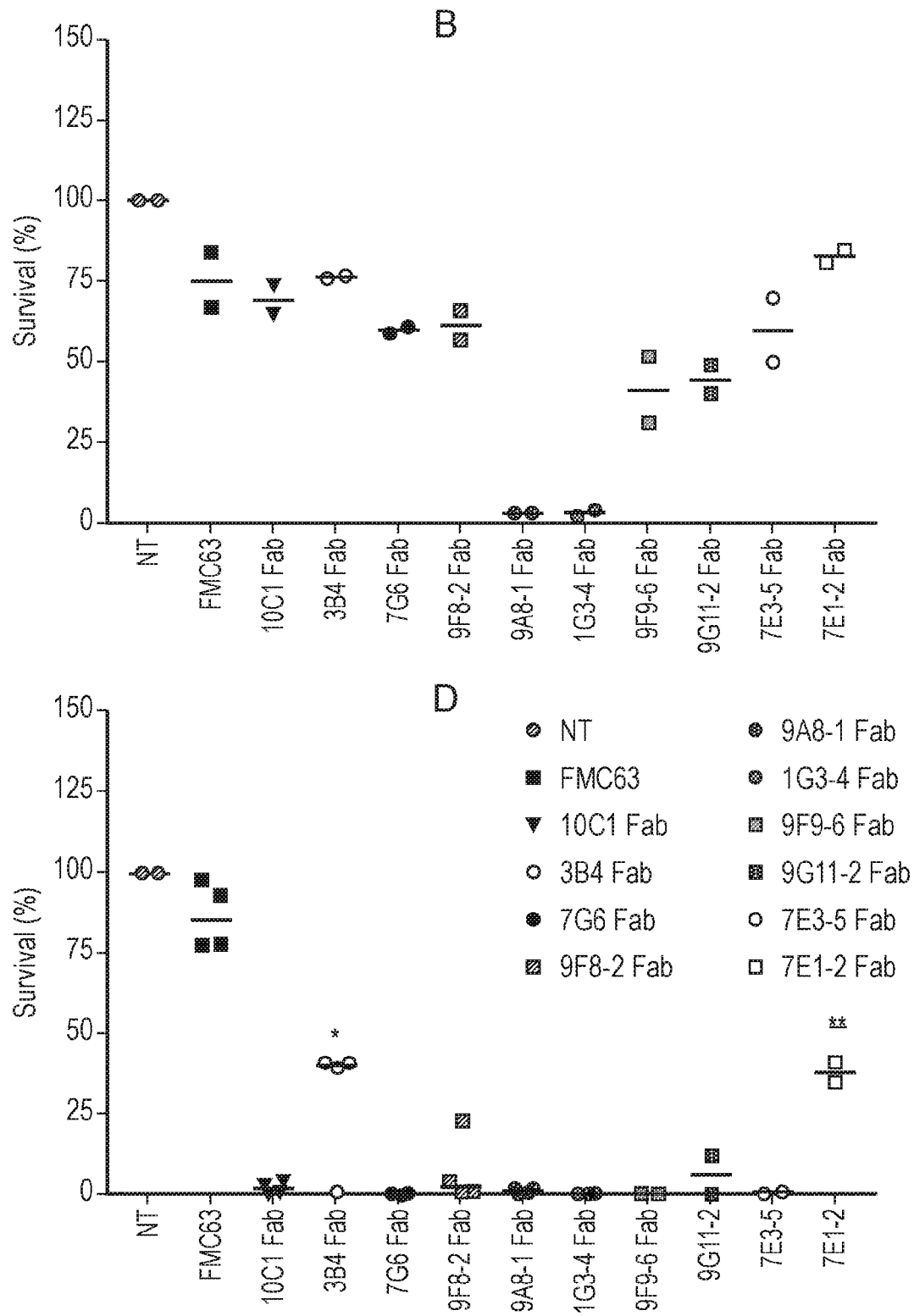

The results of the FBK are shown in FIG. 10. All of the anti-CD22 FabCARs showed effective killing of target cells expressing a high level of target antigen (FIG. 10D). However, the Fab CARs having a 9 Å8 antigen-binding domain or an 1G3-4 antigen binding domain showed killing at of target cells even at an ultra low level of expression of target antigen (panel B).

Transduction

Retrovirus was generated by transiently transfecting 293T cells using Gene Juice (EMD Millipore) with RDF plasmid (RD114 envelope), gag/pol plasmid and CAR T-cell plasmid and viral supernatant was collected at 48 and 72 hours. T cells were stimulated using 0.5 μg/mL of anti-CD3 and anti-CD28 antibodies in T175 TC-treated flasks and maintained in 100 U/mL IL-2. Non-TC treated six-well plates were coated with Retronectin in accordance to manufacturer's instructions (Takara Bio) and incubated at 4° C. for 24 hours prior to T cell transduction. 3 ml of viral supernatant was plated prior to the addition of 1 ml of activated T cells at a concentration of 1×10 cells/ml, 100 U/mL of IL-2 was then added and centrifuged at 1000×g for 40 minutes at room temperature and incubated at 37° C. and 5% $CO_2$ for 2-3 days.

NK Cells and NKT Cells Depletion

EasySep™ Human CD56 Positive Selection Kit used to carry out CD56 depletion (STEMCELL 18055).

Cytotoxicity Assay

To measure cytotoxicity, CAR T-cells were co-cultured with SupT1-NT and SupT1 CD22 at effector:target ratios 4:1 (200,000:50,000 cells) in a TC-treated 96-well plate. Readout was taken at 72 hours by staining with anti-hCD34-APC (FAB7227A), anti-CD2-FITC and anti-CD3-PeCy7 (300419) to differentiate effector T-cells and target cells, 7-AAD cell viability dye (420403) was used to exclude dead cells and phosphate-buffered saline (Ser. No. 10/010,023) to carry out cell washes between incubations. Cytotoxicity readouts were acquired using the MACSQuant® Analyzer 10 flow cytometer (Miltenyi Biotec).

Cytokine Release

Production of IL-2 by CAR T-cells were measured by collecting supernatant at 72 hr from co-cultures at a 4:1 E:T ratio and freezing at −20° C. prior to analysis by ELISA. Cytokine analysis were performed using the Human IFN-γ ELISA MAX™ Deluxe Sets (BioLegend, 430106) and IL-2 ELISA MAX™ Deluxe Sets (BioLegend, 431806) following manufacturers protocol. Varioskan LUX Multimode Microplate Reader (Thermo Fisher) used to measure ELISA signal.

This application claims the benefit of United Kingdom application No. 1807866.7 filed 15 May 2018 and United Kingdom application No. 1809773.3 filed 14 Jun. 2018. Both of the above applications are incorporated herein by reference in their entireties.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

The invention claimed is:

1. An anti-CD22 antigen-binding domain which comprises:
   a) a heavy chain variable region (VH) having complementarity determining regions (CDRs) with the following sequences:

```
                                           (SEQ ID NO: 93)
           CDR1 - NFAMA, (SEQ ID NO: 94)
           CDR2 - SISTGGGNTYYRDSVKG,
           and (SEQ ID NO: 95)
           CDR3 - QRNYYDGSYDYEGYTMDA,
   ``` and
   b) a light chain variable region (VL) having complementarity determining regions (CDRs) with the following sequences:

```
                                           (SEQ ID NO: 96)
           CDR1 - RSSQDIGNYLT, (SEQ ID NO: 97)
           CDR2 - GAIKLED,
           and (SEQ ID NO: 98)
           CDR3 - LQSIQYP.
   ```

2. An antigen-binding domain according to claim 1, which comprises a VH domain having the sequence shown as SEQ ID NO: 65; and a VL domain having the sequence shown as SEQ ID NO: 66.

3. An anti-CD22 chimeric antigen receptor (CAR) which comprises an antigen-binding domain according to claim 1.

4. A nucleic acid sequence which encodes a CAR according to claim 3.

5. A nucleic acid construct which comprises a first nucleic acid sequence according to claim 4 and a second nucleic acid sequence encoding an anti-CD19 CAR.

6. A nucleic acid construct according to claim 5, wherein the antigen binding domain of the anti-CD19 CAR comprises:
 a) a heavy chain variable region (VH) having complementarity determining regions (CDRs) with the following sequences:

```
                              (SEQ ID NO: 69)
        CDR1 - GYAFSSS, (SEQ ID NO: 70)
        CDR2 - YPGDED,
        and (SEQ ID NO: 71)
        CDR3 - SLLYGDYLDY,
```
and
 b) a light chain variable region (VL) having CDRs with the following sequences:

```
                              (SEQ ID NO: 72)
        CDR1 - SASSSVSYMH, (SEQ ID NO: 73)
        CDR2 - DTSKLAS,
        and (SEQ ID NO: 74)
        CDR3 - QQWNINPLT.
```

7. A nucleic acid construct according to claim 5, wherein the antigen-binding domain of the anti-CD19 CAR comprises a VH domain as shown in SEQ ID NO: 75 and a VL domain as shown as SEQ ID NO: 76.

8. A nucleic acid construct according to claim 5, wherein the anti-CD22 CAR is in an ScFv format, the nucleic acid construct having the general structure:
 AgBD1-spacer1-TM1-endo1-coexpr-AgBD2-spacer2-TM2-endo2 or
 AgBD2-spacer2-TM2-endo2-coexpr-AgBD1-spacer1-TM1-endo1,
wherein:
 AgBD1 is a nucleic acid sequence encoding an antigen binding domain of the first CAR,
 Spacer1 is a nucleic acid sequence encoding a spacer of the first CAR,
 TM1 is a a nucleic acid sequence encoding a transmembrane domain of the first CAR,
 Endo1 is a nucleic acid sequence encoding an endodomain of the first CAR,
 Coexpr is a nucleic acid sequence enabling co-expression of the first and second CARs,
 AgBD2 is a nucleic acid sequence encoding an antigen binding domain of the second CAR,
 Spacer2 is a nucleic acid sequence encoding a spacer of the second CAR,
 TM2 is a a nucleic acid sequence encoding a transmembrane domain of the second CAR, and
 Endo2 is a nucleic acid sequence encoding an endodomain of the second CAR.

9. A vector which comprises a nucleic acid sequence according to claim 4.

10. A method for making a cell, which comprises the step of introducing a nucleic acid sequence according to claim 4 into a cell ex vivo.

11. A cell which expresses a CAR according to claim 3.

12. A pharmaceutical composition which comprises a plurality of cells according to claim 11, together with a pharmaceutically acceptable carrier, diluent or excipient.

13. A cell which co-expresses a first CAR according to claim 3 and a second CAR which is an anti-CD19 CAR.

14. A cell according to claim 13, wherein the antigen binding domain of the anti-CD19 CAR comprises
 a) a heavy chain variable region (VH) having complementarity determining regions (CDRs) with the following sequences:

```
                              (SEQ ID NO: 69)
        CDR1 - GYAFSSS, (SEQ ID NO: 70)
        CDR2 - YPGDED,
        and (SEQ ID NO: 71)
        CDR3 - SLLYGDYLDY,
```
and
 b) a light chain variable region (VL) having CDRs with the following sequences:

```
                              (SEQ ID NO: 72)
        CDR1 - SASSSVSYMH, (SEQ ID NO: 73)
        CDR2 - DTSKLAS,
        and (SEQ ID NO: 74)
        CDR3 - QQWNINPLT.
```

15. A cell according to claim 14, wherein the antigen-binding domain of the anti-CD19 CAR comprises a VH domain as shown in SEQ ID NO: 75 and a VL domain as shown as SEQ ID NO: 76.

16. A method for treating a B cell leukemia or B cell lymphoma which comprises the step of administering a pharmaceutical composition according to claim 12 to a subject.

* * * * *

SEQUENCE LISTING

```
<160> NUMBER OF SEQ ID NOS: 136

<210> SEQ ID NO 1
<211> LENGTH: 106
<212> TYPE: PRT
<213> ORGANISM: Artificial Sequence
<220> FEATURE:
<223> OTHER INFORMATION: kappa chain constant domain (light chain
      constant domain of chimeric recptor)

<400> SEQUENCE: 1

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105
```

-continued

```
<210> SEQ ID NO 2
<211> LENGTH: 97
<212> TYPE: PRT
<213> ORGANISM: Artificial Sequence
<220> FEATURE:
<223> OTHER INFORMATION: gamma immunoglobulin heavy chain (heavy chain
      constant domain of chimeric receptor)

<400> SEQUENCE: 2

Ser Thr Lys Gly Pro Ser Val Phe Pro Leu Ala Pro Ser Ser Lys Ser
1               5                   10                  15

Thr Ser Gly Gly Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Ser Leu Gly Thr Gln Thr Tyr
65                  70                  75                  80

Ile Cys Asn Val Asn His Lys Pro Ser Asn Thr Lys Val Asp Lys Arg
                85                  90                  95

Val

<210> SEQ ID NO 3
<211> LENGTH: 20
<212> TYPE: PRT
<213> ORGANISM: Artificial Sequence
<220> FEATURE:
<223> OTHER INFORMATION: spacer, human IgG1 hinge

<400> SEQUENCE: 3

Ala Glu Pro Lys Ser Pro Asp Lys Thr His Thr Cys Pro Pro Cys Pro
1               5                   10                  15

Lys Asp Pro Lys
            20

<210> SEQ ID NO 4
<211> LENGTH: 15
<212> TYPE: PRT
<213> ORGANISM: Artificial Sequence
<220> FEATURE:
<223> OTHER INFORMATION: spacer, hinge spacer

<400> SEQUENCE: 4

Glu Pro Lys Ser Cys Asp Lys Thr His Thr Cys Pro Pro Cys Pro
1               5                   10                  15

<210> SEQ ID NO 5
<211> LENGTH: 6
<212> TYPE: PRT
<213> ORGANISM: Artificial Sequence
<220> FEATURE:
<223> OTHER INFORMATION: heavy chain variable region (VH)
      complementarity determining region (CDR), CDR1

<400> SEQUENCE: 5

Ser Asp Tyr Ala Trp Asn
1               5

<210> SEQ ID NO 6
<211> LENGTH: 16
<212> TYPE: PRT
<213> ORGANISM: Artificial Sequence
```

<220> FEATURE:
<223> OTHER INFORMATION: VH CDR sequence, CDR2

<400> SEQUENCE: 6

Asn Ile Trp Tyr Ser Gly Ser Thr Thr Tyr Asn Pro Ser Leu Lys Ser
1               5                   10                  15

<210> SEQ ID NO 7
<211> LENGTH: 3
<212> TYPE: PRT
<213> ORGANISM: Artificial Sequence
<220> FEATURE:
<223> OTHER INFORMATION: VH CDR sequence, CDR3

<400> SEQUENCE: 7

Met Asp Phe
1

<210> SEQ ID NO 8
<211> LENGTH: 17
<212> TYPE: PRT
<213> ORGANISM: Artificial Sequence
<220> FEATURE:
<223> OTHER INFORMATION: light chain variable region (VL) CDR sequence,
      CDR1

<400> SEQUENCE: 8

Arg Ala Ser Glu Ser Val Asp Ser Tyr Gly Lys Thr Phe Met His Trp
1               5                   10                  15

His

<210> SEQ ID NO 9
<211> LENGTH: 7
<212> TYPE: PRT
<213> ORGANISM: Artificial Sequence
<220> FEATURE:
<223> OTHER INFORMATION: VL CDR sequence, CDR2

<400> SEQUENCE: 9

Arg Val Ser Asn Leu Glu Ser
1               5

<210> SEQ ID NO 10
<211> LENGTH: 9
<212> TYPE: PRT
<213> ORGANISM: Artificial Sequence
<220> FEATURE:
<223> OTHER INFORMATION: VL CDR sequence, CDR3

<400> SEQUENCE: 10

Gln Gln Ser Asn Glu Asp Pro Phe Thr
1               5

<210> SEQ ID NO 11
<211> LENGTH: 112
<212> TYPE: PRT
<213> ORGANISM: Artificial Sequence
<220> FEATURE:
<223> OTHER INFORMATION: VH sequence from murine monoclonal antibody

<400> SEQUENCE: 11

Glu Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
            35                  40                  45

Met Gly Asn Ile Trp Tyr Ser Gly Ser Thr Thr Tyr Asn Pro Ser Leu
 50                  55                  60

Lys Ser Arg Ile Ser Ile Thr Arg Asp Thr Ser Lys Asn Gln Phe Phe
 65                  70                  75                  80

Leu Gln Leu Asn Ser Val Thr Ser Glu Asp Thr Ala Thr Tyr Tyr Cys
                 85                  90                  95

Ser Arg Met Asp Phe Trp Gly Gln Gly Thr Thr Leu Thr Val Ser Ser
            100                 105                 110

<210> SEQ ID NO 12
<211> LENGTH: 112
<212> TYPE: PRT
<213> ORGANISM: Artificial Sequence
<220> FEATURE:
<223> OTHER INFORMATION: VL sequence from murine monoclonal antibody

<400> SEQUENCE: 12

Asp Ile Val Leu Thr Gln Ser Pro Pro Ser Leu Ala Val Ser Leu Gly
 1               5                  10                  15

Gln Arg Ala Thr Ile Ser Cys Arg Ala Ser Glu Ser Val Asp Ser Tyr
             20                  25                  30

Gly Lys Thr Phe Met His Trp His Gln Gln Lys Pro Gly Gln Pro Pro
         35                  40                  45

Lys Leu Leu Ile Tyr Arg Val Ser Asn Leu Glu Ser Gly Ile Pro Ala
 50                  55                  60

Arg Phe Ser Gly Ser Gly Ser Arg Thr Asp Phe Thr Leu Thr Ile Asn
 65                  70                  75                  80

Pro Val Glu Ala Asp Asp Val Ala Thr Tyr Tyr Cys Gln Gln Ser Asn
                 85                  90                  95

Glu Asp Pro Phe Thr Phe Gly Gly Gly Thr Lys Leu Glu Ile Lys Arg
            100                 105                 110

<210> SEQ ID NO 13
<211> LENGTH: 245
<212> TYPE: PRT
<213> ORGANISM: Artificial Sequence
<220> FEATURE:
<223> OTHER INFORMATION: mouse anti-cynomolgus (Macaca fascicularis)
      CD79b 10D10 scFv sequence

<400> SEQUENCE: 13

Asp Ile Val Leu Thr Gln Ser Pro Pro Ser Leu Ala Val Ser Leu Gly
 1               5                  10                  15

Gln Arg Ala Thr Ile Ser Cys Arg Ala Ser Glu Ser Val Asp Ser Tyr
             20                  25                  30

Gly Lys Thr Phe Met His Trp His Gln Gln Lys Pro Gly Gln Pro Pro
         35                  40                  45

Lys Leu Leu Ile Tyr Arg Val Ser Asn Leu Glu Ser Gly Ile Pro Ala
 50                  55                  60

Arg Phe Ser Gly Ser Gly Ser Arg Thr Asp Phe Thr Leu Thr Ile Asn
 65                  70                  75                  80

Pro Val Glu Ala Asp Asp Val Ala Thr Tyr Tyr Cys Gln Gln Ser Asn
                 85                  90                  95

Glu Asp Pro Phe Thr Phe Gly Gly Gly Thr Lys Leu Glu Ile Lys Arg
            100                 105                 110

```
Ser Gly Gly Gly Ser Gly Gly Gly Ser Gly Gly Gly Ser
        115                 120                 125

Gly Gly Gly Gly Ser Glu Val Gln Leu Gln Glu Ser Gly Pro Gly Leu
        130                 135                 140

Val Lys Pro Ser Gln Ser Leu Ser Leu Thr Cys Thr Val Thr Gly Tyr
145                 150                 155                 160

Ser Ile Thr Ser Asp Tyr Ala Trp Asn Trp Ile Arg Gln Phe Pro Gly
                165                 170                 175

Asn Lys Leu Glu Trp Met Gly Asn Ile Trp Tyr Ser Gly Ser Thr Thr
            180                 185                 190

Tyr Asn Pro Ser Leu Lys Ser Arg Ile Ser Ile Thr Arg Asp Thr Ser
        195                 200                 205

Lys Asn Gln Phe Phe Leu Gln Leu Asn Ser Val Thr Ser Glu Asp Thr
    210                 215                 220

Ala Thr Tyr Tyr Cys Ser Arg Met Asp Phe Trp Gly Gln Gly Thr Thr
225                 230                 235                 240

Leu Thr Val Ser Ser
                245

<210> SEQ ID NO 14
<211> LENGTH: 5
<212> TYPE: PRT
<213> ORGANISM: Artificial Sequence
<220> FEATURE:
<223> OTHER INFORMATION: VH CDR sequence, CDR1

<400> SEQUENCE: 14

Ser Tyr Trp Ile Glu
1               5

<210> SEQ ID NO 15
<211> LENGTH: 17
<212> TYPE: PRT
<213> ORGANISM: Artificial Sequence
<220> FEATURE:
<223> OTHER INFORMATION: VH CDR sequence, CDR2

<400> SEQUENCE: 15

Glu Ile Leu Pro Gly Gly Gly Asp Thr Asn Tyr Asn Glu Ile Phe Lys
1               5                   10                  15

Gly

<210> SEQ ID NO 16
<211> LENGTH: 8
<212> TYPE: PRT
<213> ORGANISM: Artificial Sequence
<220> FEATURE:
<223> OTHER INFORMATION: VH CDR sequence, CDR3

<400> SEQUENCE: 16

Arg Val Pro Val Tyr Phe Asp Tyr
1               5

<210> SEQ ID NO 17
<211> LENGTH: 15
<212> TYPE: PRT
<213> ORGANISM: Artificial Sequence
<220> FEATURE:
<223> OTHER INFORMATION: VL CDR sequence, CDR1
```

<400> SEQUENCE: 17

Lys Ala Ser Gln Ser Val Asp Tyr Asp Gly Asp Ser Phe Leu Asn
1               5                   10                  15

<210> SEQ ID NO 18
<211> LENGTH: 7
<212> TYPE: PRT
<213> ORGANISM: Artificial Sequence
<220> FEATURE:
<223> OTHER INFORMATION: VL CDR sequence, CDR2

<400> SEQUENCE: 18

Ala Ala Ser Asn Leu Glu Ser
1               5

<210> SEQ ID NO 19
<211> LENGTH: 9
<212> TYPE: PRT
<213> ORGANISM: Artificial Sequence
<220> FEATURE:
<223> OTHER INFORMATION: VL CDR sequence, CDR3

<400> SEQUENCE: 19

Gln Gln Ser Asn Glu Asp Pro Leu Thr
1               5

<210> SEQ ID NO 20
<211> LENGTH: 117
<212> TYPE: PRT
<213> ORGANISM: Artificial Sequence
<220> FEATURE:
<223> OTHER INFORMATION: VH sequence from murine monoclonal antibody

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Ser Ser Tyr
                20                  25                  30

Trp Ile Glu Trp Val Arg Gln Ala Pro Gly Lys Gly Leu Glu Trp Ile
            35                  40                  45

Gly Glu Ile Leu Pro Gly Gly Gly Asp Thr Asn Tyr Asn Glu Ile Phe
        50                  55                  60

Lys Gly Arg Ala Thr Phe Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Thr Arg Arg Val Pro Val Tyr Phe Asp Tyr Trp Gly Gln Gly Thr Leu
            100                 105                 110

Val Thr Val Ser Ser
        115

<210> SEQ ID NO 21
<211> LENGTH: 112
<212> TYPE: PRT
<213> ORGANISM: Artificial Sequence
<220> FEATURE:
<223> OTHER INFORMATION: VL sequence from murine monoclonal antibody -continued

```
<400> SEQUENCE: 21

Asp Ile Gln Leu Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Asp
            20                  25                  30

Gly Asp Ser Phe Leu Asn Trp Tyr Gln Gln Lys Pro Gly Lys Ala Pro
        35                  40                  45

Lys Leu Leu Ile Tyr Ala Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Asn
                85                  90                  95

Glu Asp Pro Leu Thr Phe Gly Gln Gly Thr Lys Val Glu Ile Lys Arg
            100                 105                 110

<210> SEQ ID NO 22
<211> LENGTH: 270
<212> TYPE: PRT
<213> ORGANISM: Artificial Sequence
<220> FEATURE:
<223> OTHER INFORMATION: humanised anti-CD79b-v17 scFv

<400> SEQUENCE: 22

Met Glu Thr Asp Thr Leu Leu Leu Trp Val Leu Leu Leu Trp Val Pro
1               5                   10                  15

Gly Ser Thr Gly Asp Ile Gln Leu Thr Gln Ser Pro Ser Ser Leu Ser
            20                  25                  30

Ala Ser Val Gly Asp Arg Val Thr Ile Thr Cys Lys Ala Ser Gln Ser
        35                  40                  45

Val Asp Tyr Asp Gly Asp Ser Phe Leu Asn Trp Tyr Gln Gln Lys Pro
    50                  55                  60

Gly Lys Ala Pro Lys Leu Leu Ile Tyr Ala Ala Ser Asn Leu Glu Ser
65                  70                  75                  80

Gly Val Pro Ser Arg Phe Ser Gly Ser Gly Ser Gly Thr Asp Phe Thr
                85                  90                  95

Leu Thr Ile Ser Ser Leu Gln Pro Glu Asp Phe Ala Thr Tyr Tyr Cys
            100                 105                 110

Gln Gln Ser Asn Glu Asp Pro Leu Thr Phe Gly Gln Gly Thr Lys Val
        115                 120                 125

Glu Ile Lys Arg Ser Gly Gly Gly Gly Ser Gly Gly Gly Gly Ser Gly
    130                 135                 140

Gly Gly Gly Ser Gly Gly Gly Gly Ser Glu Val Gln Leu Val Glu Ser
145                 150                 155                 160

Gly Gly Gly Leu Val Gln Pro Gly Gly Ser Leu Arg Leu Ser Cys Ala
                165                 170                 175

Ala Ser Gly Tyr Thr Phe Ser Ser Tyr Trp Ile Glu Trp Val Arg Gln
            180                 185                 190

Ala Pro Gly Lys Gly Leu Glu Trp Ile Gly Glu Ile Leu Pro Gly Gly
        195                 200                 205

Gly Asp Thr Asn Tyr Asn Glu Ile Phe Lys Gly Arg Ala Thr Phe Ser
    210                 215                 220

Ala Asp Thr Ser Lys Asn Thr Ala Tyr Leu Gln Met Asn Ser Leu Arg
225                 230                 235                 240
```

```
Ala Glu Asp Thr Ala Val Tyr Tyr Cys Thr Arg Arg Val Pro Val Tyr
                245                 250                 255

Phe Asp Tyr Trp Gly Gln Gly Thr Leu Val Thr Val Ser Ser
        260                 265                 270

<210> SEQ ID NO 23
<211> LENGTH: 8
<212> TYPE: PRT
<213> ORGANISM: Artificial Sequence
<220> FEATURE:
<223> OTHER INFORMATION: VH CDR sequence, CDR3

<400> SEQUENCE: 23

Arg Val Pro Ile Arg Leu Asp Tyr
1               5

<210> SEQ ID NO 24
<211> LENGTH: 117
<212> TYPE: PRT
<213> ORGANISM: Artificial Sequence
<220> FEATURE:
<223> OTHER INFORMATION: VH sequence from murine monoclonal antibody

<400> SEQUENCE: 24

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Ser Ser Tyr
            20                  25                  30

Trp Ile Glu Trp Val Arg Gln Ala Pro Gly Lys Gly Leu Glu Trp Ile
        35                  40                  45

Gly Glu Ile Leu Pro Gly Gly Asp Thr Asn Tyr Asn Glu Ile Phe
    50                  55                  60

Lys Gly Arg Ala Thr Phe Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Thr Arg Arg Val Pro Ile Arg Leu Asp Tyr Trp Gly Gln Gly Thr Leu
            100                 105                 110

Val Thr Val Ser Ser
        115

<210> SEQ ID NO 25
<211> LENGTH: 250
<212> TYPE: PRT
<213> ORGANISM: Artificial Sequence
<220> FEATURE:
<223> OTHER INFORMATION: humanised anti-CD79b v18 scFv sequence

<400> SEQUENCE: 25

Asp Ile Gln Leu Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Asp
            20                  25                  30

Gly Asp Ser Phe Leu Asn Trp Tyr Gln Gln Lys Pro Gly Lys Ala Pro
        35                  40                  45

Lys Leu Leu Ile Tyr Ala Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80
```

```
Ser Leu Gln Pro Glu Asp Phe Ala Thr Tyr Tyr Cys Gln Gln Ser Asn
                85                  90                  95

Glu Asp Pro Leu Thr Phe Gly Gln Gly Thr Lys Val Glu Ile Lys Arg
            100                 105                 110

Ser Gly Gly Gly Gly Ser Gly Gly Gly Ser Gly Gly Gly Gly Ser
        115                 120                 125

Gly Gly Gly Gly Ser Glu Val Gln Leu Val Glu Ser Gly Gly Gly Leu
130                 135                 140

Val Gln Pro Gly Gly Ser Leu Arg Leu Ser Cys Ala Ala Ser Gly Tyr
145                 150                 155                 160

Thr Phe Ser Ser Tyr Trp Ile Glu Trp Val Arg Gln Ala Pro Gly Lys
                165                 170                 175

Gly Leu Glu Trp Ile Gly Glu Ile Leu Pro Gly Gly Gly Asp Thr Asn
            180                 185                 190

Tyr Asn Glu Ile Phe Lys Gly Arg Ala Thr Phe Ser Ala Asp Thr Ser
        195                 200                 205

Lys Asn Thr Ala Tyr Leu Gln Met Asn Ser Leu Arg Ala Glu Asp Thr
210                 215                 220

Ala Val Tyr Tyr Cys Thr Arg Arg Val Pro Ile Arg Leu Asp Tyr Trp
225                 230                 235                 240

Gly Gln Gly Thr Leu Val Thr Val Ser Ser
                245                 250

<210> SEQ ID NO 26
<211> LENGTH: 15
<212> TYPE: PRT
<213> ORGANISM: Artificial Sequence
<220> FEATURE:
<223> OTHER INFORMATION: VL CDR sequence, CDR1

<400> SEQUENCE: 26

Lys Ala Ser Gln Ser Val Asp Tyr Glu Gly Asp Ser Phe Leu Asn
1               5                   10                  15

<210> SEQ ID NO 27
<211> LENGTH: 112
<212> TYPE: PRT
<213> ORGANISM: Artificial Sequence
<220> FEATURE:
<223> OTHER INFORMATION: VL sequence from murine monoclonal antibody

<400> SEQUENCE: 27

Asp Ile Gln Leu Thr Gln Ser Pro Ser Leu Ser Ala Ser Val Gly
1               5                   10                  15

Asp Arg Val Thr Ile Thr Cys Lys Ala Ser Gln Ser Val Asp Tyr Glu
            20                  25                  30

Gly Asp Ser Phe Leu Asn Trp Tyr Gln Gln Lys Pro Gly Lys Ala Pro
        35                  40                  45

Lys Leu Leu Ile Tyr Ala Ala Ser Asn Leu Glu Ser Gly Val Pro Ser
50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Asn
                85                  90                  95

Glu Asp Pro Leu Thr Phe Gly Gln Gly Thr Lys Val Glu Ile Lys Arg
            100                 105                 110
```

```
<210> SEQ ID NO 28
<211> LENGTH: 270
<212> TYPE: PRT
<213> ORGANISM: Artificial Sequence
<220> FEATURE:
<223> OTHER INFORMATION: humanised anti-CD79b v28 scFv sequence

<400> SEQUENCE: 28

Met Glu Thr Asp Thr Leu Leu Leu Trp Val Leu Leu Leu Trp Val Pro
1               5                   10                  15

Gly Ser Thr Gly Asp Ile Gln Leu Thr Gln Ser Pro Ser Ser Leu Ser
            20                  25                  30

Ala Ser Val Gly Asp Arg Val Thr Ile Thr Cys Lys Ala Ser Gln Ser
        35                  40                  45

Val Asp Tyr Glu Gly Asp Ser Phe Leu Asn Trp Tyr Gln Gln Lys Pro
    50                  55                  60

Gly Lys Ala Pro Lys Leu Leu Ile Tyr Ala Ala Ser Asn Leu Glu Ser
65                  70                  75                  80

Gly Val Pro Ser Arg Phe Ser Gly Ser Gly Ser Gly Thr Asp Phe Thr
                85                  90                  95

Leu Thr Ile Ser Ser Leu Gln Pro Glu Asp Phe Ala Thr Tyr Tyr Cys
            100                 105                 110

Gln Gln Ser Asn Glu Asp Pro Leu Thr Phe Gly Gln Gly Thr Lys Val
        115                 120                 125

Glu Ile Lys Arg Ser Gly Gly Gly Gly Ser Gly Gly Gly Gly Ser Gly
    130                 135                 140

Gly Gly Gly Ser Gly Gly Gly Gly Ser Glu Val Gln Leu Val Glu Ser
145                 150                 155                 160

Gly Gly Gly Leu Val Gln Pro Gly Gly Ser Leu Arg Leu Ser Cys Ala
                165                 170                 175

Ala Ser Gly Tyr Thr Phe Ser Ser Tyr Trp Ile Glu Trp Val Arg Gln
            180                 185                 190

Ala Pro Gly Lys Gly Leu Glu Trp Ile Gly Glu Ile Leu Pro Gly Gly
        195                 200                 205

Gly Asp Thr Asn Tyr Asn Glu Ile Phe Lys Gly Arg Ala Thr Phe Ser
    210                 215                 220

Ala Asp Thr Ser Lys Asn Thr Ala Tyr Leu Gln Met Asn Ser Leu Arg
225                 230                 235                 240

Ala Glu Asp Thr Ala Val Tyr Tyr Cys Thr Arg Arg Val Pro Ile Arg
                245                 250                 255

Leu Asp Tyr Trp Gly Gln Gly Thr Leu Val Thr Val Ser Ser
            260                 265                 270

<210> SEQ ID NO 29
<211> LENGTH: 15
<212> TYPE: PRT
<213> ORGANISM: Artificial Sequence
<220> FEATURE:
<223> OTHER INFORMATION: VL CDR sequence, CDR1

<400> SEQUENCE: 29

Lys Ala Ser Gln Ser Val Asp Tyr Ser Gly Asp Ser Phe Leu Asn
1               5                   10                  15

<210> SEQ ID NO 30
<211> LENGTH: 112
<212> TYPE: PRT
<213> ORGANISM: Artificial Sequence
```

```
<220> FEATURE:
<223> OTHER INFORMATION: VL sequence from murine monoclonal antibody

<400> SEQUENCE: 30

Asp Ile Gln Leu Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Ser
                20                  25                  30

Gly Asp Ser Phe Leu Asn Trp Tyr Gln Gln Lys Pro Gly Lys Ala Pro
            35                  40                  45

Lys Leu Phe Ile Tyr Ala Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Asn
                85                  90                  95

Glu Asp Pro Leu Thr Phe Gly Gln Gly Thr Lys Val Glu Ile Lys Arg
            100                 105                 110

<210> SEQ ID NO 31
<211> LENGTH: 270
<212> TYPE: PRT
<213> ORGANISM: Artificial Sequence
<220> FEATURE:
<223> OTHER INFORMATION: humanised anti-CD79b v32 scFv sequence

<400> SEQUENCE: 31

Met Glu Thr Asp Thr Leu Leu Leu Trp Val Leu Leu Leu Trp Val Pro
1               5                   10                  15

Gly Ser Thr Gly Asp Ile Gln Leu Thr Gln Ser Pro Ser Ser Leu Ser
                20                  25                  30

Ala Ser Val Gly Asp Arg Val Thr Ile Thr Cys Lys Ala Ser Gln Ser
            35                  40                  45

Val Asp Tyr Ser Gly Asp Ser Phe Leu Asn Trp Tyr Gln Gln Lys Pro
    50                  55                  60

Gly Lys Ala Pro Lys Leu Phe Ile Tyr Ala Ala Ser Asn Leu Glu Ser
65                  70                  75                  80

Gly Val Pro Ser Arg Phe Ser Gly Ser Gly Ser Gly Thr Asp Phe Thr
                85                  90                  95

Leu Thr Ile Ser Ser Leu Gln Pro Glu Asp Phe Ala Thr Tyr Tyr Cys
            100                 105                 110

Gln Gln Ser Asn Glu Asp Pro Leu Thr Phe Gly Gln Gly Thr Lys Val
            115                 120                 125

Glu Ile Lys Arg Ser Gly Gly Gly Gly Ser Gly Gly Gly Gly Ser Gly
            130                 135                 140

Gly Gly Ser Gly Gly Gly Gly Ser Glu Val Gln Leu Val Glu Ser
145                 150                 155                 160

Gly Gly Gly Leu Val Gln Pro Gly Gly Ser Leu Arg Leu Ser Cys Ala
                165                 170                 175

Ala Ser Gly Tyr Thr Phe Ser Ser Tyr Trp Ile Glu Trp Val Arg Gln
            180                 185                 190

Ala Pro Gly Lys Gly Leu Glu Trp Ile Gly Glu Ile Leu Pro Gly Gly
            195                 200                 205

Gly Asp Thr Asn Tyr Asn Glu Ile Phe Lys Gly Arg Ala Thr Phe Ser
    210                 215                 220
```

Ala Asp Thr Ser Lys Asn Thr Ala Tyr Leu Gln Met Asn Ser Leu Arg
225                 230                 235                 240

Ala Glu Asp Thr Ala Val Tyr Tyr Cys Thr Arg Arg Val Pro Ile Arg
                245                 250                 255

Leu Asp Tyr Trp Gly Gln Gly Thr Leu Val Thr Val Ser Ser
            260                 265                 270

<210> SEQ ID NO 32
<211> LENGTH: 117
<212> TYPE: PRT
<213> ORGANISM: Artificial Sequence
<220> FEATURE:
<223> OTHER INFORMATION: VH sequence from murine monoclonal antibody

<400> SEQUENCE: 32

Glu Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Ser Ser Tyr
            20                  25                  30

Trp Ile Glu Trp Val Lys Gln Arg Pro Gly His Gly Leu Glu Trp Ile
        35                  40                  45

Gly Glu Ile Leu Pro Gly Gly Asp Thr Asn Tyr Asn Glu Ile Phe
    50                  55                  60

Lys Gly Lys Ala Thr Phe Thr Ala Asp Thr Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Thr Arg Arg Val Pro Val Tyr Phe Asp Tyr Trp Gly Gln Gly Thr Ser
            100                 105                 110

Val Thr Val Ser Ser
        115

<210> SEQ ID NO 33
<211> LENGTH: 112
<212> TYPE: PRT
<213> ORGANISM: Artificial Sequence
<220> FEATURE:
<223> OTHER INFORMATION: VL sequence from murine monoclonal antibody

<400> SEQUENCE: 33

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Phe Leu Asn Trp Tyr Gln Gln Lys Pro Gly Gln Pro Pro
        35                  40                  45

Lys Leu Phe Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Glu Asp Pro Leu Thr Phe Gly Ala Gly Thr Leu Glu Leu Lys Arg
            100                 105                 110

<210> SEQ ID NO 34
<211> LENGTH: 270
<212> TYPE: PRT
<213> ORGANISM: Artificial Sequence
<220> FEATURE:
<223> OTHER INFORMATION: murine anti-CD79b SN8 scFv sequence

<400> SEQUENCE: 34

```
Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Ser Leu Ala
            20                  25                  30

Val Ser Leu Gly Gln Arg Ala Thr Ile Ser Cys Lys Ala Ser Gln Ser
        35                  40                  45

Val Asp Tyr Asp Gly Asp Ser Phe Leu Asn Trp Tyr Gln Gln Lys Pro
    50                  55                  60

Gly Gln Pro Pro Lys Leu Phe Ile Tyr Ala Ala Ser Asn Leu Glu Ser
65                  70                  75                  80

Gly Ile Pro Ala Arg Phe Ser Gly Ser Gly Ser Gly Thr Asp Phe Thr
                85                  90                  95

Leu Asn Ile His Pro Val Glu Glu Asp Ala Ala Thr Tyr Tyr Cys
            100                 105                 110

Gln Gln Ser Asn Glu Asp Pro Leu Thr Phe Gly Ala Gly Thr Glu Leu
        115                 120                 125

Glu Leu Lys Arg Ser Gly Gly Gly Ser Gly Gly Gly Ser Gly
    130                 135                 140

Gly Gly Gly Ser Gly Gly Gly Ser Glu Val Gln Leu Gln Gln Ser
145                 150                 155                 160

Gly Ala Glu Leu Met Lys Pro Gly Ala Ser Val Lys Ile Ser Cys Lys
                165                 170                 175

Ala Thr Gly Tyr Thr Phe Ser Ser Tyr Trp Ile Glu Trp Val Lys Gln
            180                 185                 190

Arg Pro Gly His Gly Leu Glu Trp Ile Gly Glu Ile Leu Pro Gly Gly
        195                 200                 205

Gly Asp Thr Asn Tyr Asn Glu Ile Phe Lys Gly Lys Ala Thr Phe Thr
    210                 215                 220

Ala Asp Thr Ser Ser Asn Thr Ala Tyr Met Gln Leu Ser Ser Leu Thr
225                 230                 235                 240

Ser Glu Asp Ser Ala Val Tyr Tyr Cys Thr Arg Arg Val Pro Val Tyr
                245                 250                 255

Phe Asp Tyr Trp Gly Gln Gly Thr Ser Val Thr Val Ser Ser
            260                 265                 270
```

<210> SEQ ID NO 35
<211> LENGTH: 5
<212> TYPE: PRT
<213> ORGANISM: Artificial Sequence
<220> FEATURE:
<223> OTHER INFORMATION: VH CDR sequence, CDR3

<400> SEQUENCE: 35

```
Tyr Ala Met Asp Tyr
1               5
```

<210> SEQ ID NO 36
<211> LENGTH: 113
<212> TYPE: PRT
<213> ORGANISM: Artificial Sequence
<220> FEATURE:
<223> OTHER INFORMATION: VH sequence from murine monoclonal antibody

```
<400> SEQUENCE: 36

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asn Tyr
            20                  25                  30

Gly Met Asn Trp Val Lys Gln Arg Pro Gly Gln Gly Leu Gln Trp Ile
        35                  40                  45

Gly Arg Ile Tyr Pro Gly Ser Gly Ser Thr Asn Tyr Gln Lys Phe Lys
50                  55                  60

Gly Lys Ala Thr Leu Thr Val Asp Lys Ser Ser Ser Thr Ala Tyr Met
65                  70                  75                  80

Glu Leu Arg Ser Leu Thr Ser Glu Asn Ser Ala Val Tyr Tyr Cys Ala
                85                  90                  95

Arg Tyr Ala Met Asp Tyr Thr Gly Gln Gly Thr Ser Val Thr Val Ser
            100                 105                 110

Ser

<210> SEQ ID NO 37
<211> LENGTH: 113
<212> TYPE: PRT
<213> ORGANISM: Artificial Sequence
<220> FEATURE:
<223> OTHER INFORMATION: VL sequence from murine monoclonal antibody

<400> SEQUENCE: 37

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Pro Ser Gly Val Pro
50                  55                  60

Asn Arg Phe Ser Gly Ser Gly Ser Gly Thr Asp Phe Thr Leu Lys Ile
65                  70                  75                  80

Ser Arg Val Gln Ala Gln Asn Leu Gly Val Tyr Tyr Cys Phe Gln Gly
                85                  90                  95

Ser His Val Pro Trp Thr Phe Gly Gly Gly Thr Lys Leu Glu Ile Lys
            100                 105                 110

Arg

<210> SEQ ID NO 38
<211> LENGTH: 267
<212> TYPE: PRT
<213> ORGANISM: Artificial Sequence
<220> FEATURE:
<223> OTHER INFORMATION: murine anti-CD79a scFv sequence

<400> SEQUENCE: 38

Met Glu Thr Asp Thr Leu Leu Leu Trp Val Leu Leu Leu Trp Val Pro
1               5                   10                  15

Gly Ser Thr Gly Asp Val Leu Met Thr Gln Thr Pro Leu Ser Leu Pro
            20                  25                  30

Val Ser Leu Gly Asp Gln Ala Ser Ile Ser Cys Arg Ser Ser Gln Ser
        35                  40                  45

Ile Val His Ser Asn Gly Asn Thr Tyr Leu Glu Trp Tyr Leu Gln Lys
50                  55                  60
```

```
Pro Gly Gln Ser Pro Lys Leu Leu Ile Tyr Lys Val Ser Asn Arg Pro
 65                  70                  75                  80

Ser Gly Val Pro Asn Arg Phe Ser Gly Ser Gly Ser Gly Thr Asp Phe
                 85                  90                  95

Thr Leu Lys Ile Ser Arg Val Gln Ala Gln Asn Leu Gly Val Tyr Tyr
            100                 105                 110

Cys Phe Gln Gly Ser His Val Pro Trp Thr Phe Gly Gly Gly Thr Lys
            115                 120                 125

Leu Glu Ile Lys Arg Ser Gly Gly Gly Ser Gly Gly Gly Gly Gly Ser
        130                 135                 140

Gly Gly Gly Gly Ser Gly Gly Gly Ser Gln Val Gln Leu Gln Gln
145                 150                 155                 160

Ser Gly Pro Glu Leu Val Lys Pro Gly Ala Ser Val Lys Ile Ser Cys
                165                 170                 175

Lys Ala Ser Gly Tyr Thr Phe Thr Asn Tyr Gly Met Asn Trp Val Lys
            180                 185                 190

Gln Arg Pro Gly Gln Gly Leu Gln Trp Ile Gly Arg Ile Tyr Pro Gly
        195                 200                 205

Ser Gly Ser Thr Asn Tyr Gln Lys Phe Lys Gly Lys Ala Thr Leu Thr
210                 215                 220

Val Asp Lys Ser Ser Ser Thr Ala Tyr Met Glu Leu Arg Ser Leu Thr
225                 230                 235                 240

Ser Glu Asn Ser Ala Val Tyr Tyr Cys Ala Arg Tyr Ala Met Asp Tyr
                245                 250                 255

Thr Gly Gln Gly Thr Ser Val Thr Val Ser Ser
            260                 265

<210> SEQ ID NO 39
<211> LENGTH: 119
<212> TYPE: PRT
<213> ORGANISM: Artificial Sequence
<220> FEATURE:
<223> OTHER INFORMATION: VH sequence from 1D9-3 antibody

<400> SEQUENCE: 39

Glu Val Gln Leu Val Glu Ser Gly Gly Gly Leu Val Gln Pro Lys Gly
  1               5                  10                  15

Ser Leu Lys Leu Ser Cys Ala Ala Ser Gly Phe Thr Phe Asn Thr Tyr
             20                  25                  30

Ala Met His Trp Val Arg Gln Ala Pro Gly Lys Gly Leu Glu Trp Val
         35                  40                  45

Ala Arg Ile Arg Ser Lys Ser Ser Asn Tyr Ala Thr Tyr Tyr Ala Asp
     50                  55                  60

Ser Val Lys Asp Arg Phe Thr Ile Ser Arg Asp Asp Ser Gln Ser Met
 65                  70                  75                  80

Leu Tyr Leu Gln Met Asn Asn Leu Lys Thr Glu Asp Thr Ala Met Tyr
                 85                  90                  95

Tyr Cys Val Val Asp Tyr Leu Tyr Ala Met Asp Tyr Trp Gly Gln Gly
            100                 105                 110

Thr Ser Val Thr Val Ser Ser
        115

<210> SEQ ID NO 40
<211> LENGTH: 107
<212> TYPE: PRT
<213> ORGANISM: Artificial Sequence
```

```
<220> FEATURE:
<223> OTHER INFORMATION: VL sequence from 1D9-3 antibody

<400> SEQUENCE: 40

Asp Ile Val Met Thr Gln Ser Gln Lys Phe Met Ser Thr Ser Val Gly
1               5                   10                  15

Asp Arg Val Ser Ile Thr Cys Lys Ala Ser Gln Asn Val Arg Thr Ala
            20                  25                  30

Val Ala Trp Tyr Gln Gln Lys Pro Gly Gln Ser Pro Lys Ala Leu Ile
        35                  40                  45

Tyr Leu Ala Ser Asn Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Leu Gln His Trp Asn Tyr Pro Phe
                85                  90                  95

Thr Phe Gly Ser Gly Thr Lys Leu Glu Ile Lys
            100                 105

<210> SEQ ID NO 41
<211> LENGTH: 120
<212> TYPE: PRT
<213> ORGANISM: Artificial Sequence
<220> FEATURE:
<223> OTHER INFORMATION: VH sequence from 3B4-13 antibody

<400> SEQUENCE: 41

Gln Val Gln Leu Gln Gln Ser Gly Ala Glu Leu Val Arg Pro Gly Ala
1               5                   10                  15

Ser Val Thr Leu Ser Cys Lys Ala Ser Gly Tyr Thr Phe Thr Asp Tyr
            20                  25                  30

Glu Met His Trp Val Lys Gln Thr Pro Val His Gly Leu Glu Trp Ile
        35                  40                  45

Gly Ala Ile Asp Pro Glu Thr Gly Ala Thr Ala Tyr Asn Gln Lys Phe
    50                  55                  60

Lys Gly Lys Ala Ile Leu Thr Ala Asp Lys Ser Ser Ser Thr Ala Tyr
65                  70                  75                  80

Met Asp Leu Arg Ser Leu Thr Ser Glu Asp Ser Ala Val Tyr Tyr Cys
                85                  90                  95

Thr Arg Tyr Asp Tyr Gly Ser Ser Pro Trp Phe Ala Tyr Trp Gly Gln
            100                 105                 110

Gly Thr Leu Val Thr Val Ser Ala
        115                 120

<210> SEQ ID NO 42
<211> LENGTH: 109
<212> TYPE: PRT
<213> ORGANISM: Artificial Sequence
<220> FEATURE:
<223> OTHER INFORMATION: VL sequence from 3B4-13 antibody

<400> SEQUENCE: 42

Gln Ala Val Val Thr Gln Glu Ser Ala Leu Thr Thr Ser Pro Gly Glu
1               5                   10                  15

Thr Val Thr Leu Thr Cys Arg Ser Ser Ala Gly Ala Val Thr Thr Ser
            20                  25                  30

Asn Tyr Ala Asn Trp Val Gln Glu Lys Pro Asp His Leu Phe Thr Gly
        35                  40                  45
```

```
Leu Ile Gly Gly Thr Asn Asn Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Asn Ser Asn
                85                  90                  95

His Trp Val Phe Gly Gly Gly Thr Lys Leu Thr Val Leu
            100                 105
```

<210> SEQ ID NO 43
<211> LENGTH: 119
<212> TYPE: PRT
<213> ORGANISM: Artificial Sequence
<220> FEATURE:
<223> OTHER INFORMATION: VH sequence from 7G6-6 antibody

<400> SEQUENCE: 43

```
Gln Val Gln Leu Gln Gln Pro Gly Ala Glu Leu Val Met Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Glu Ile Asp Pro Ser Asp Ser Tyr Thr Asn Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Tyr Tyr Gly Ser Ser Ser Phe Asp Tyr Trp Gly Gln Gly
            100                 105                 110

Thr Thr Leu Thr Val Ser Ser
        115
```

<210> SEQ ID NO 44
<211> LENGTH: 111
<212> TYPE: PRT
<213> ORGANISM: Artificial Sequence
<220> FEATURE:
<223> OTHER INFORMATION: VL sequence from 7G6-6 antibody

<400> SEQUENCE: 44

```
Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Thr Phe Gly Gly Gly Thr Lys Leu Glu Ile Lys
            100                 105                 110
```

```
<210> SEQ ID NO 45
<211> LENGTH: 120
<212> TYPE: PRT
<213> ORGANISM: Artificial Sequence
<220> FEATURE:
<223> OTHER INFORMATION: VH sequence from 6C4-6 antibody

<400> SEQUENCE: 45

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
            20                  25                  30

Gly Val His Trp Val Arg Gln Pro Pro Gly Lys Gly Leu Glu Trp Leu
        35                  40                  45

Val Val Ile Trp Ser Asp Gly Ser Thr Thr Tyr Asn Ser Ala Leu Lys
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Met Tyr Tyr Cys Ala
                85                  90                  95

Arg His Ala Asp Asp Tyr Gly Phe Ala Trp Phe Ala Tyr Trp Gly Gln
            100                 105                 110

Gly Thr Leu Val Thr Val Ser Ala
        115                 120

<210> SEQ ID NO 46
<211> LENGTH: 107
<212> TYPE: PRT
<213> ORGANISM: Artificial Sequence
<220> FEATURE:
<223> OTHER INFORMATION: VL sequence from 6C4-6 antibody

<400> SEQUENCE: 46

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Tyr Gly Thr Pro Pro
                85                  90                  95

Thr Phe Gly Gly Gly Thr Lys Leu Glu Ile Lys
            100                 105

<210> SEQ ID NO 47
<211> LENGTH: 121
<212> TYPE: PRT
<213> ORGANISM: Artificial Sequence
<220> FEATURE:
<223> OTHER INFORMATION: VH sequence from 4D9-12 antibody

<400> SEQUENCE: 47

Glu Phe Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Asp Tyr
            20                  25                  30
```

Asn Met Asn Trp Val Lys Gln Ser Asn Gly Lys Ser Leu Glu Trp Ile
        35                  40                  45

Gly Val Ile Asn Pro Asn Tyr Gly Thr Thr Ser Tyr Asn Gln Lys Phe
 50                  55                  60

Lys Gly Lys Ala Thr Leu Thr Val Asp Gln Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Ser Ser Thr Thr Val Val Asp Trp Tyr Phe Asp Val Trp Gly
            100                 105                 110

Thr Gly Thr Thr Val Thr Val Ser Ser
            115                 120

<210> SEQ ID NO 48
<211> LENGTH: 107
<212> TYPE: PRT
<213> ORGANISM: Artificial Sequence
<220> FEATURE:
<223> OTHER INFORMATION: VL sequence from 4D9-12 antibody

<400> SEQUENCE: 48

Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Glu Ile Ser Gly Tyr
            20                  25                  30

Leu Ser Trp Leu Gln Gln Lys Pro Asp Gly Thr Ile Lys Arg Leu Ile
        35                  40                  45

Tyr Ala Ala Ser Thr Leu Asp Ser Gly Val Pro Lys Arg Phe Ser Gly
 50                  55                  60

Ser Arg Ser Gly Ser Asp Tyr Ser Leu Thr Ile Ser Ser Leu Glu Ser
65                  70                  75                  80

Glu Asp Phe Ala Asp Tyr Tyr Cys Leu Gln Tyr Ala Ser Tyr Pro Phe
                85                  90                  95

Thr Phe Gly Ser Gly Thr Lys Leu Glu Ile Lys
            100                 105

<210> SEQ ID NO 49
<211> LENGTH: 118
<212> TYPE: PRT
<213> ORGANISM: Artificial Sequence
<220> FEATURE:
<223> OTHER INFORMATION: VH sequence from 5H4-9 antibody

<400> SEQUENCE: 49

Gln Val Gln Val Gln Gln Pro Gly Ala Glu Leu Val Arg Pro Gly Thr
1               5                   10                  15

Ser Val Lys Leu Ser Cys Lys Ala Ser Gly Tyr Thr Phe Thr Arg Tyr
            20                  25                  30

Trp Met Tyr Trp Val Lys Gln Arg Pro Gly Gln Gly Leu Glu Trp Ile
        35                  40                  45

Gly Val Ile Asp Pro Ser Asp Asn Phe Thr Tyr Tyr Asn Gln Lys Phe
 50                  55                  60

Lys Gly Lys Ala Thr Leu Thr Val Asp Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Tyr Gly Ser Ser Tyr Val Gly Tyr Trp Gly Gln Gly Thr
            100                 105                 110

```
Thr Leu Thr Val Ser Ser
        115

<210> SEQ ID NO 50
<211> LENGTH: 113
<212> TYPE: PRT
<213> ORGANISM: Artificial Sequence
<220> FEATURE:
<223> OTHER INFORMATION: VL sequence from 5H4-9 antibody

<400> SEQUENCE: 50

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Pro Trp Thr Phe Gly Gly Gly Thr Lys Leu Glu Ile
            100                 105                 110

Lys

<210> SEQ ID NO 51
<211> LENGTH: 124
<212> TYPE: PRT
<213> ORGANISM: Artificial Sequence
<220> FEATURE:
<223> OTHER INFORMATION: VH sequence from 10C1-D9 antibody

<400> SEQUENCE: 51

Gln Val Thr Leu Lys Glu Ser Gly Pro Gly Ile Leu Gln Ser Ser Gln
1               5                   10                  15

Thr Leu Ser Leu Thr Cys Ser Phe Ser Gly Phe Ser Leu Ser Thr Ser
            20                  25                  30

Asp Met Gly Val Ser Trp Ile Arg Gln Pro Ser Gly Lys Gly Leu Glu
        35                  40                  45

Trp Leu Ala His Ile Tyr Trp Asp Asp Lys Arg Tyr Asn Pro Ser
    50                  55                  60

Leu Lys Ser Arg Leu Thr Ile Ser Lys Asp Ala Ser Arg Asn Gln Val
65                  70                  75                  80

Phe Leu Lys Ile Ala Thr Val Asp Thr Ala Asp Thr Ala Thr Tyr Tyr
                85                  90                  95

Cys Ala Arg Ser Pro Trp Ile Tyr Tyr Gly His Tyr Trp Cys Phe Asp
            100                 105                 110

Val Trp Gly Thr Gly Thr Thr Val Thr Val Ser Ser
        115                 120

<210> SEQ ID NO 52
<211> LENGTH: 107
<212> TYPE: PRT
<213> ORGANISM: Artificial Sequence
<220> FEATURE:
<223> OTHER INFORMATION: VL sequence from 10C1-D9 antibody
```

<400> SEQUENCE: 52

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Phe
                85                  90                  95

Thr Phe Gly Ser Gly Thr Lys Leu Glu Ile Lys
            100                 105

<210> SEQ ID NO 53
<211> LENGTH: 123
<212> TYPE: PRT
<213> ORGANISM: Artificial Sequence
<220> FEATURE:
<223> OTHER INFORMATION: VH sequence from 15G7-2 antibody

<400> SEQUENCE: 53

Gln Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Thr Glu Tyr
            20                  25                  30

Thr Ile His Trp Val Lys Gln Arg Ser Gly Gln Gly Leu Glu Trp Ile
        35                  40                  45

Gly Trp Phe Tyr Pro Gly Ser Gly Ser Ile Lys Tyr Asn Glu Lys Phe
50                  55                  60

Lys Asp Lys Ala Thr Leu Thr Ala Asp Lys Ser Ser Thr Val Tyr
65                  70                  75                  80

Met Glu Leu Ser Arg Leu Thr Ser Glu Asp Ser Ala Val Tyr Phe Cys
                85                  90                  95

Ala Arg His Gly Asp Gly Tyr Tyr Leu Pro Pro Tyr Tyr Phe Asp Tyr
            100                 105                 110

Trp Gly Gln Gly Thr Thr Leu Thr Val Ser Ser
        115                 120

<210> SEQ ID NO 54
<211> LENGTH: 106
<212> TYPE: PRT
<213> ORGANISM: Artificial Sequence
<220> FEATURE:
<223> OTHER INFORMATION: VL sequence from 15G7-2 antibody

<400> SEQUENCE: 54

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

Tyr Trp Tyr Gln Gln Lys Pro Gly Ser Ser Pro Arg Leu Leu Ile Tyr
        35                  40                  45

Asp Thr Ser Asn Leu Ala Ser Gly Val Pro Val Arg Phe Ser Gly Ser
50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Trp Ser Ser Tyr Pro Leu Thr
                85                  90                  95

Phe Gly Ala Gly Thr Lys Leu Glu Leu Lys
            100                 105

<210> SEQ ID NO 55
<211> LENGTH: 121
<212> TYPE: PRT
<213> ORGANISM: Artificial Sequence
<220> FEATURE:
<223> OTHER INFORMATION: VH sequence from 2B12-8 antibody

<400> SEQUENCE: 55

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Ile Phe Thr Ser Tyr
                20                  25                  30

Gly Ile Ser Trp Val Lys Gln Arg Thr Gly Gln Gly Leu Glu Trp Ile
            35                  40                  45

Gly Glu Ile Tyr Pro Arg Ser Gly Asn Thr Tyr Tyr Asn Glu Lys Phe
50                  55                  60

Lys Gly Lys Ala Thr Leu Thr Ala Asp Lys Ser Ser Ser Thr Ala Tyr
65                  70                  75                  80

Met Glu Leu Arg Ser Leu Thr Ser Glu Asp Ser Ala Val Tyr Phe Cys
                85                  90                  95

Ala Arg Pro Ile Tyr Tyr Gly Ser Arg Glu Gly Phe Asp Tyr Trp Gly
            100                 105                 110

Gln Gly Thr Thr Leu Thr Val Ser Ser
        115                 120

<210> SEQ ID NO 56
<211> LENGTH: 107
<212> TYPE: PRT
<213> ORGANISM: Artificial Sequence
<220> FEATURE:
<223> OTHER INFORMATION: VL sequence from 2B12-8 antibody

<400> SEQUENCE: 56

Asp Ile Val Leu Thr Gln Ser Pro Ala Thr Leu Ser Val Thr Pro Gly
1               5                   10                  15

Asp Ser Val Ser Leu Ser Cys Arg Ala Ser Gln Ser Ile Ser Thr Asn
                20                  25                  30

Leu His Trp Tyr Gln Gln Lys Ser His Ala Ser Pro Arg Leu Leu Ile
            35                  40                  45

Lys Tyr Ala Ser Gln Ser Val Ser Gly Ile Pro Ser Arg Phe Ser Gly
50                  55                  60

Ser Gly Ser Gly Thr Asp Phe Thr Leu Ser Ile Asn Ser Val Glu Thr
65                  70                  75                  80

Glu Asp Phe Gly Ile Phe Phe Cys Gln Gln Ser Tyr Ser Trp Pro Tyr
                85                  90                  95

Thr Phe Gly Gly Gly Thr Lys Leu Glu Ile Lys
            100                 105

<210> SEQ ID NO 57
<211> LENGTH: 120
<212> TYPE: PRT
<213> ORGANISM: Artificial Sequence

```
<220> FEATURE:
<223> OTHER INFORMATION: VH sequence from 2C4-4 antibody

<400> SEQUENCE: 57

Gln Val Gln Leu Gln Gln Pro Gly Ala Glu Leu Val Met Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Glu Ile Asp Pro Ser Asp Ser Tyr Thr Asn Tyr Asn Gln Lys Phe
    50                  55                  60

Lys Gly Lys Ser Thr Leu Thr Val Asp Lys Ser Ser Ser Thr Ala Tyr
65                  70                  75                  80

Ile Gln Leu Ser Ser Leu Thr Ser Glu Asp Ser Ala Val Tyr Tyr Cys
                85                  90                  95

Ala Arg Trp Ala Ser Tyr Arg Gly Tyr Ala Met Asp Tyr Trp Gly Gln
            100                 105                 110

Gly Thr Ser Val Thr Val Ser Ser
        115                 120

<210> SEQ ID NO 58
<211> LENGTH: 112
<212> TYPE: PRT
<213> ORGANISM: Artificial Sequence
<220> FEATURE:
<223> OTHER INFORMATION: VL sequence from 2C4-4 antibody

<400> SEQUENCE: 58

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Glu Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Trp Thr Phe Gly Gly Gly Thr Lys Leu Glu Ile Lys
            100                 105                 110

<210> SEQ ID NO 59
<211> LENGTH: 119
<212> TYPE: PRT
<213> ORGANISM: Artificial Sequence
<220> FEATURE:
<223> OTHER INFORMATION: VH sequence from 3E10-7 antibody

<400> SEQUENCE: 59

Glu Phe Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Asp Tyr
            20                  25                  30

Asn Met Asn Trp Val Lys Gln Ser Asn Gly Lys Ser Leu Glu Trp Ile
        35                  40                  45
```

Gly Val Ile Asn Pro Asn Tyr Gly Thr Thr Ser Tyr Asn Gln Arg Phe
            50                  55                  60

Lys Gly Lys Ala Thr Leu Thr Val Asp Gln Ser Ser Thr Ala Tyr
 65                  70                  75                  80

Met Gln Leu Asn Ser Leu Thr Ser Glu Asp Ser Ala Val Tyr Tyr Cys
                 85                  90                  95

Ala Arg Ser Gly Leu Arg Tyr Trp Tyr Phe Asp Val Trp Gly Thr Gly
                100                 105                 110

Thr Thr Val Thr Val Ser Ser
            115

<210> SEQ ID NO 60
<211> LENGTH: 107
<212> TYPE: PRT
<213> ORGANISM: Artificial Sequence
<220> FEATURE:
<223> OTHER INFORMATION: VL sequence from 3E10-7 antibody

<400> SEQUENCE: 60

Asp Ile Gln Met Thr Gln Ser Pro Ser Ser Leu Ser Ala Ser Leu Gly
  1               5                  10                  15

Glu Arg Val Ser Leu Thr Cys Arg Ala Ser Gln Glu Ile Ser Gly Tyr
             20                  25                  30

Leu Ser Trp Leu Gln Gln Lys Pro Asp Gly Thr Ile Lys Arg Leu Ile
         35                  40                  45

Tyr Ala Ala Ser Thr Leu Asp Ser Gly Val Pro Lys Arg Phe Ser Gly
     50                  55                  60

Ser Arg Ser Gly Ser Asp Tyr Ser Leu Thr Ile Ser Ser Leu Glu Ser
 65                  70                  75                  80

Glu Asp Phe Ala Asp Tyr Tyr Cys Leu Gln Tyr Ala Ser Tyr Pro Phe
                 85                  90                  95

Thr Phe Gly Ser Gly Thr Lys Leu Glu Ile Lys
            100                 105

<210> SEQ ID NO 61
<211> LENGTH: 120
<212> TYPE: PRT
<213> ORGANISM: Artificial Sequence
<220> FEATURE:
<223> OTHER INFORMATION: VH sequence from LT22 antibody

<400> SEQUENCE: 61

Glu Val Gln Leu Val Glu Ser Gly Ala Glu Val Lys Lys Pro Gly Ser
  1               5                  10                  15

Ser Val Lys Val Ser Cys Lys Ala Ser Gly Tyr Thr Phe Thr Asn Tyr
             20                  25                  30

Trp Ile Asn Trp Val Arg Gln Ala Pro Gly Gln Gly Leu Glu Trp Met
         35                  40                  45

Gly Asn Ile Tyr Pro Ser Asp Ser Phe Thr Asn Tyr Asn Gln Lys Phe
     50                  55                  60

Lys Asp Arg Val Thr Ile Thr Ala Asp Lys Ser Thr Ser Thr Val Tyr
 65                  70                  75                  80

Leu Glu Leu Arg Asn Leu Arg Ser Asp Asp Thr Ala Val Tyr Tyr Cys
                 85                  90                  95

Thr Arg Asp Thr Gln Glu Arg Ser Trp Tyr Phe Asp Val Trp Gly Gln
                100                 105                 110

Gly Thr Leu Val Thr Val Ser Ser
            115                 120

```
<210> SEQ ID NO 62
<211> LENGTH: 113
<212> TYPE: PRT
<213> ORGANISM: Artificial Sequence
<220> FEATURE:
<223> OTHER INFORMATION: VL sequence from LT22 antibody

<400> SEQUENCE: 62

Asp Ile Val Met Thr Gln Ser Pro Ala Thr Leu Ser Val Ser Pro Gly
1               5                   10                  15

Glu Arg Ala Thr Leu Ser Cys Arg Ser Ser Gln Ser Leu Val His Ser
            20                  25                  30

Asn Gly Asn Thr Tyr Leu His Trp Tyr Gln Gln Lys Pro Gly Gln Ala
        35                  40                  45

Pro Arg Leu Leu Ile Tyr Lys Val Ser Asn Arg Phe Ser Gly Val Pro
    50                  55                  60

Ala Arg Phe Ser Gly Ser Gly Ser Gly Ala Glu Phe Thr Leu Thr Ile
65                  70                  75                  80

Ser Ser Leu Gln Ser Glu Asp Phe Ala Val Tyr Tyr Cys Ser Gln Ser
                85                  90                  95

Thr His Val Pro Trp Thr Phe Gly Gln Gly Thr Arg Leu Glu Ile Lys
            100                 105                 110

Arg

<210> SEQ ID NO 63
<211> LENGTH: 121
<212> TYPE: PRT
<213> ORGANISM: Artificial Sequence
<220> FEATURE:
<223> OTHER INFORMATION: VH sequence from Inotuzumab G5_44 antibody

<400> SEQUENCE: 63

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Arg Phe Thr Asn Tyr
            20                  25                  30

Trp Ile His Trp Val Arg Gln Ala Pro Gly Gln Gly Leu Glu Trp Ile
        35                  40                  45

Gly Gly Ile Asn Pro Gly Asn Asn Tyr Ala Thr Tyr Arg Arg Lys Phe
    50                  55                  60

Gln Gly Arg Val Thr Met Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Glu Gly Tyr Gly Asn Tyr Gly Ala Trp Phe Ala Tyr Trp Gly
            100                 105                 110

Gln Gly Thr Leu Val Thr Val Ser Ser
        115                 120

<210> SEQ ID NO 64
<211> LENGTH: 113
<212> TYPE: PRT
<213> ORGANISM: Artificial Sequence
<220> FEATURE:
<223> OTHER INFORMATION: VL sequence from Inotuzumab G5_44 antibody

<400> SEQUENCE: 64

Asp Val Gln Val Thr Gln Ser Pro Ser Ser Leu Ser Ala Ser Val Gly
1               5                   10                  15
```

```
Asp Arg Val Thr Ile Thr Cys Arg Ser Ser Gln Ser Leu Ala Asn Ser
                20                  25                  30

Tyr Gly Asn Thr Phe Leu Ser Trp Tyr Leu His Lys Pro Gly Lys Ala
            35                  40                  45

Pro Gln Leu Leu Ile Tyr Gly Ile Ser Asn Arg Phe Ser Gly Val Pro
        50                  55                  60

Asp Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Leu Gln Gly
                85                  90                  95

Thr His Gln Pro Tyr Thr Phe Gly Gln Gly Thr Lys Val Glu Ile Lys
                100                 105                 110

Arg

<210> SEQ ID NO 65
<211> LENGTH: 127
<212> TYPE: PRT
<213> ORGANISM: Artificial Sequence
<220> FEATURE:
<223> OTHER INFORMATION: VH sequence from 9A8-1 antibody

<400> SEQUENCE: 65

Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe Ser Asn Phe
                20                  25                  30

Ala Met Ala Trp Val Arg Gln Pro Thr Lys Gly Leu Glu Trp Val
            35                  40                  45

Ala Ser Ile Ser Thr Gly Gly Gly Asn Thr Tyr Tyr Arg Asp Ser Val
        50                  55                  60

Lys Gly Arg Phe Thr Ile Ser Arg Asp Asp Ala Lys Asn Thr Gln Tyr
65                  70                  75                  80

Leu Gln Met Asp Ser Leu Arg Ser Glu Asp Thr Ala Thr Tyr Tyr Cys
                85                  90                  95

Ala Arg Gln Arg Asn Tyr Tyr Asp Gly Ser Tyr Asp Tyr Glu Gly Tyr
                100                 105                 110

Thr Met Asp Ala Trp Gly Gln Gly Thr Ser Val Thr Val Ser Ser
            115                 120                 125

<210> SEQ ID NO 66
<211> LENGTH: 107
<212> TYPE: PRT
<213> ORGANISM: Artificial Sequence
<220> FEATURE:
<223> OTHER INFORMATION: VL sequence from 9A8-1 antibody

<400> SEQUENCE: 66

Asp Ile Gln Met Thr Gln Ser Pro Ser Ser Leu Ser Ala Ser Leu Gly
1               5                   10                  15

Asp Arg Val Thr Ile Thr Cys Arg Ser Ser Gln Asp Ile Gly Asn Tyr
                20                  25                  30

Leu Thr Trp Phe Gln Gln Lys Val Gly Arg Ser Pro Arg Arg Met Ile
            35                  40                  45

Tyr Gly Ala Ile Lys Leu Glu Asp Gly Val Pro Ser Arg Phe Ser Gly
        50                  55                  60

Ser Arg Ser Gly Ser Asp Tyr Ser Leu Thr Ile Ser Ser Leu Glu Ser
65                  70                  75                  80
```

Glu Asp Val Ala Asp Tyr Gln Cys Leu Gln Ser Ile Gln Tyr Pro Phe
                85                  90                  95

Thr Phe Gly Ser Gly Thr Lys Leu Glu Ile Lys
            100                 105

<210> SEQ ID NO 67
<211> LENGTH: 226
<212> TYPE: PRT
<213> ORGANISM: Homo sapiens

<400> SEQUENCE: 67

Met Pro Gly Gly Pro Gly Val Leu Gln Ala Leu Pro Ala Thr Ile Phe
1               5                   10                  15

Leu Leu Phe Leu Leu Ser Ala Val Tyr Leu Gly Pro Gly Cys Gln Ala
                20                  25                  30

Leu Trp Met His Lys Val Pro Ala Ser Leu Met Val Ser Leu Gly Glu
            35                  40                  45

Asp Ala His Phe Gln Cys Pro His Asn Ser Ser Asn Ala Asn Val
50                  55                  60

Thr Trp Trp Arg Val Leu His Gly Asn Tyr Thr Trp Pro Pro Glu Phe
65                  70                  75                  80

Leu Gly Pro Gly Glu Asp Pro Asn Gly Thr Leu Ile Ile Gln Asn Val
                85                  90                  95

Asn Lys Ser His Gly Gly Ile Tyr Val Cys Arg Val Gln Glu Gly Asn
            100                 105                 110

Glu Ser Tyr Gln Gln Ser Cys Gly Thr Tyr Leu Arg Val Arg Gln Pro
        115                 120                 125

Pro Pro Arg Pro Phe Leu Asp Met Gly Glu Gly Thr Lys Asn Arg Ile
130                 135                 140

Ile Thr Ala Glu Gly Ile Ile Leu Leu Phe Cys Ala Val Val Pro Gly
145                 150                 155                 160

Thr Leu Leu Leu Phe Arg Lys Arg Trp Gln Asn Glu Lys Leu Gly Leu
                165                 170                 175

Asp Ala Gly Asp Glu Tyr Glu Asp Glu Asn Leu Tyr Glu Gly Leu Asn
            180                 185                 190

Leu Asp Asp Cys Ser Met Tyr Glu Asp Ile Ser Arg Gly Leu Gln Gly
        195                 200                 205

Thr Tyr Gln Asp Val Gly Ser Leu Asn Ile Gly Asp Val Gln Leu Glu
210                 215                 220

Lys Pro
225

<210> SEQ ID NO 68
<211> LENGTH: 229
<212> TYPE: PRT
<213> ORGANISM: Homo sapiens

<400> SEQUENCE: 68

Met Ala Arg Leu Ala Leu Ser Pro Val Pro Ser His Trp Met Val Ala
1               5                   10                  15

Leu Leu Leu Leu Leu Ser Ala Glu Pro Val Pro Ala Ala Arg Ser Glu
                20                  25                  30

Asp Arg Tyr Arg Asn Pro Lys Gly Ser Ala Cys Ser Arg Ile Trp Gln
            35                  40                  45

Ser Pro Arg Phe Ile Ala Arg Lys Arg Gly Phe Thr Val Lys Met His
50                  55                  60

```
Cys Tyr Met Asn Ser Ala Ser Gly Asn Val Ser Trp Leu Trp Lys Gln
 65                  70                  75                  80

Glu Met Asp Glu Asn Pro Gln Gln Leu Lys Leu Glu Lys Gly Arg Met
                 85                  90                  95

Glu Glu Ser Gln Asn Glu Ser Leu Ala Thr Leu Thr Ile Gln Gly Ile
            100                 105                 110

Arg Phe Glu Asp Asn Gly Ile Tyr Phe Cys Gln Gln Lys Cys Asn Asn
        115                 120                 125

Thr Ser Glu Val Tyr Gln Gly Cys Gly Thr Glu Leu Arg Val Met Gly
    130                 135                 140

Phe Ser Thr Leu Ala Gln Leu Lys Gln Arg Asn Thr Leu Lys Asp Gly
145                 150                 155                 160

Ile Ile Met Ile Gln Thr Leu Leu Ile Ile Leu Phe Ile Ile Val Pro
                165                 170                 175

Ile Phe Leu Leu Leu Asp Lys Asp Asp Ser Lys Ala Gly Met Glu Glu
                180                 185                 190

Asp His Thr Tyr Glu Gly Leu Asp Ile Asp Gln Thr Ala Thr Tyr Glu
            195                 200                 205

Asp Ile Val Thr Leu Arg Thr Gly Glu Val Lys Trp Ser Val Gly Glu
210                 215                 220

His Pro Gly Gln Glu
225

<210> SEQ ID NO 69
<211> LENGTH: 7
<212> TYPE: PRT
<213> ORGANISM: Artificial Sequence
<220> FEATURE:
<223> OTHER INFORMATION: VH CDR sequence, CDR1

<400> SEQUENCE: 69

Gly Tyr Ala Phe Ser Ser Ser
1               5

<210> SEQ ID NO 70
<211> LENGTH: 6
<212> TYPE: PRT
<213> ORGANISM: Artificial Sequence
<220> FEATURE:
<223> OTHER INFORMATION: VH CDR sequence, CDR2

<400> SEQUENCE: 70

Tyr Pro Gly Asp Glu Asp
1               5

<210> SEQ ID NO 71
<211> LENGTH: 10
<212> TYPE: PRT
<213> ORGANISM: Artificial Sequence
<220> FEATURE:
<223> OTHER INFORMATION: VH CDR sequence, CDR3

<400> SEQUENCE: 71

Ser Leu Leu Tyr Gly Asp Tyr Leu Asp Tyr
1               5                   10

<210> SEQ ID NO 72
<211> LENGTH: 10
<212> TYPE: PRT
<213> ORGANISM: Artificial Sequence
<220> FEATURE:
<223> OTHER INFORMATION: VL CDR sequence, CDR1
```

```
<400> SEQUENCE: 72

Ser Ala Ser Ser Ser Val Ser Tyr Met His
1               5                   10

<210> SEQ ID NO 73
<211> LENGTH: 7
<212> TYPE: PRT
<213> ORGANISM: Artificial Sequence
<220> FEATURE:
<223> OTHER INFORMATION: VL CDR sequence, CDR2

<400> SEQUENCE: 73

Asp Thr Ser Lys Leu Ala Ser
1               5

<210> SEQ ID NO 74
<211> LENGTH: 9
<212> TYPE: PRT
<213> ORGANISM: Artificial Sequence
<220> FEATURE:
<223> OTHER INFORMATION: VL CDR sequence, CDR3

<400> SEQUENCE: 74

Gln Gln Trp Asn Ile Asn Pro Leu Thr
1               5

<210> SEQ ID NO 75
<211> LENGTH: 119
<212> TYPE: PRT
<213> ORGANISM: Artificial Sequence
<220> FEATURE:
<223> OTHER INFORMATION: VH sequence from murine monoclonal antibody

<400> SEQUENCE: 75

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ala Phe Ser Ser Ser
            20                  25                  30

Trp Met Asn Trp Val Lys Gln Arg Pro Gly Lys Gly Leu Glu Trp Ile
        35                  40                  45

Gly Arg Ile Tyr Pro Gly Asp Glu Asp Thr Asn Tyr Ser Gly Lys Phe
    50                  55                  60

Lys Asp Lys Ala Thr Leu Thr Ala Asp Lys Ser Ser Thr Thr Ala Tyr
65                  70                  75                  80

Met Gln Leu Ser Ser Leu Thr Ser Glu Asp Ser Ala Val Tyr Phe Cys
                85                  90                  95

Ala Arg Ser Leu Leu Tyr Gly Asp Tyr Leu Asp Tyr Trp Gly Gln Gly
            100                 105                 110

Thr Thr Leu Thr Val Ser Ser
        115

<210> SEQ ID NO 76
<211> LENGTH: 107
<212> TYPE: PRT
<213> ORGANISM: Artificial Sequence
<220> FEATURE:
<223> OTHER INFORMATION: VL sequence from murine monoclonal antibody

<400> SEQUENCE: 76

Gln Ile Val Leu Thr Gln Ser Pro Ala Ile Met Ser Ala Ser Pro Gly
1               5                   10                  15
```

```
Glu Lys Val Thr Met Thr Cys Ser Ala Ser Ser Ser Val Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Asp Arg Phe Ser Gly Ser
    50                  55                  60

Gly Ser Gly Thr Ser Tyr Phe Leu Thr Ile Asn Asn Met Glu Ala Glu
65                  70                  75                  80

Asp Ala Ala Thr Tyr Tyr Cys Gln Gln Trp Asn Ile Asn Pro Leu Thr
                85                  90                  95

Phe Gly Ala Gly Thr Lys Leu Glu Leu Lys Arg
            100                 105
```

<210> SEQ ID NO 77
<211> LENGTH: 241
<212> TYPE: PRT
<213> ORGANISM: Artificial Sequence
<220> FEATURE:
<223> OTHER INFORMATION: VH-VL scFv sequence from murine monoclonal
      antibody

<400> SEQUENCE: 77

```
Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ala Phe Ser Ser Ser
            20                  25                  30

Trp Met Asn Trp Val Lys Gln Arg Pro Gly Lys Gly Leu Glu Trp Ile
        35                  40                  45

Gly Arg Ile Tyr Pro Gly Asp Glu Asp Thr Asn Tyr Ser Gly Lys Phe
    50                  55                  60

Lys Asp Lys Ala Thr Leu Thr Ala Asp Lys Ser Ser Thr Thr Ala Tyr
65                  70                  75                  80

Met Gln Leu Ser Ser Leu Thr Ser Glu Asp Ser Ala Val Tyr Phe Cys
                85                  90                  95

Ala Arg Ser Leu Leu Tyr Gly Asp Tyr Leu Asp Tyr Trp Gly Gln Gly
            100                 105                 110

Thr Thr Leu Thr Val Ser Ser Gly Gly Gly Ser Gly Gly Gly Gly
            115                 120                 125

Ser Gly Gly Gly Gly Ser Gln Ile Val Leu Thr Gln Ser Pro Ala Ile
    130                 135                 140

Met Ser Ala Ser Pro Gly Glu Lys Val Thr Met Thr Cys Ser Ala Ser
145                 150                 155                 160

Ser Ser Val Ser Tyr Met His Trp Tyr Gln Gln Lys Ser Gly Thr Ser
                165                 170                 175

Pro Lys Arg Trp Ile Tyr Asp Thr Ser Lys Leu Ala Ser Gly Val Pro
            180                 185                 190

Asp Arg Phe Ser Gly Ser Gly Ser Gly Thr Ser Tyr Phe Leu Thr Ile
        195                 200                 205

Asn Asn Met Glu Ala Glu Asp Ala Ala Thr Tyr Tyr Cys Gln Gln Trp
    210                 215                 220

Asn Ile Asn Pro Leu Thr Phe Gly Ala Gly Thr Lys Leu Glu Leu Lys
225                 230                 235                 240

Arg
```

```
<210> SEQ ID NO 78
<211> LENGTH: 5
<212> TYPE: PRT
<213> ORGANISM: Artificial Sequence
<220> FEATURE:
<223> OTHER INFORMATION: VH CDR sequence, CDR1

<400> SEQUENCE: 78

Ser Tyr Trp Met Asn
1               5

<210> SEQ ID NO 79
<211> LENGTH: 16
<212> TYPE: PRT
<213> ORGANISM: Artificial Sequence
<220> FEATURE:
<223> OTHER INFORMATION: VH CDR sequence, CDR2

<400> SEQUENCE: 79

Gln Ile Trp Pro Gly Asp Gly Asp Thr Asn Tyr Asn Gly Lys Phe Lys
1               5                   10                  15

<210> SEQ ID NO 80
<211> LENGTH: 15
<212> TYPE: PRT
<213> ORGANISM: Artificial Sequence
<220> FEATURE:
<223> OTHER INFORMATION: VH CDR sequence, CDR3

<400> SEQUENCE: 80

Arg Glu Thr Thr Thr Val Gly Arg Tyr Tyr Tyr Ala Met Asp Tyr
1               5                   10                  15

<210> SEQ ID NO 81
<211> LENGTH: 15
<212> TYPE: PRT
<213> ORGANISM: Artificial Sequence
<220> FEATURE:
<223> OTHER INFORMATION: VL CDR sequence, CDR1

<400> SEQUENCE: 81

Lys Ala Ser Gln Ser Val Asp Tyr Asp Gly Asp Ser Tyr Leu Asn
1               5                   10                  15

<210> SEQ ID NO 82
<211> LENGTH: 7
<212> TYPE: PRT
<213> ORGANISM: Artificial Sequence
<220> FEATURE:
<223> OTHER INFORMATION: VL CDR sequence, CDR2

<400> SEQUENCE: 82

Asp Ala Ser Asn Leu Val Ser
1               5

<210> SEQ ID NO 83
<211> LENGTH: 9
<212> TYPE: PRT
<213> ORGANISM: Artificial Sequence
<220> FEATURE:
<223> OTHER INFORMATION: VL CDR sequence, CDR3

<400> SEQUENCE: 83

Gln Gln Ser Thr Glu Asp Pro Trp Thr
1               5
```

```
<210> SEQ ID NO 84
<211> LENGTH: 235
<212> TYPE: PRT
<213> ORGANISM: Artificial Sequence
<220> FEATURE:
<223> OTHER INFORMATION: Murine CD19ALAb scFv sequence

<400> SEQUENCE: 84

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
                20                  25                  30

Trp Met Asn Trp Val Lys Gln Arg Pro Gly Gln Gly Leu Glu Trp Ile
            35                  40                  45

Gly Gln Ile Trp Pro Gly Asp Gly Asp Thr Asn Tyr Asn Gly Lys Phe
        50                  55                  60

Lys Gly Lys Ala Thr Leu Thr Ala Asp Glu Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Tyr Ala Met Asp
                100                 105                 110

Tyr Trp Gly Gln Gly Thr Thr Val Thr Val Ser Ser Asp Ile Gln Leu
            115                 120                 125

Thr Gln Ser Pro Ala Ser Leu Ala Val Ser Leu Gly Gln Arg Ala Thr
        130                 135                 140

Ile Ser Cys Lys Ala Ser Gln Ser Val Asp Tyr Asp Gly Asp Ser Tyr
145                 150                 155                 160

Leu Asn Trp Tyr Gln Gln Ile Pro Gly Gln Pro Pro Lys Leu Leu Ile
                165                 170                 175

Tyr Asp Ala Ser Asn Leu Val Ser Gly Ile Pro Pro Arg Phe Ser Gly
                180                 185                 190

Ser Gly Ser Gly Thr Asp Phe Thr Leu Asn Ile His Pro Val Glu Lys
            195                 200                 205

Val Asp Ala Ala Thr Tyr His Cys Gln Gln Ser Thr Glu Asp Pro Trp
        210                 215                 220

Thr Phe Gly Gly Gly Thr Lys Leu Glu Ile Lys
225                 230                 235

<210> SEQ ID NO 85
<211> LENGTH: 236
<212> TYPE: PRT
<213> ORGANISM: Artificial Sequence
<220> FEATURE:
<223> OTHER INFORMATION: Humanised CD19ALAb scFv sequence - Heavy 19,
      Kappa 16

<400> SEQUENCE: 85

Gln Val Gln Leu Val Gln Ser Gly Ala Glu Val Lys Lys Pro Gly Ala
1               5                   10                  15

Ser Val Lys Leu Ser Cys Lys Ala Ser Gly Tyr Ala Phe Ser Ser Tyr
                20                  25                  30

Trp Met Asn Trp Val Arg Gln Ala Pro Gly Gln Ser Leu Glu Trp Ile
            35                  40                  45

Gly Gln Ile Trp Pro Gly Asp Gly Asp Thr Asn Tyr Asn Gly Lys Phe
        50                  55                  60

Lys Gly Arg Ala Thr Leu Thr Ala Asp Glu Ser Ala Arg Thr Ala Tyr
65                  70                  75                  80
```

```
Met Glu Leu Ser Ser Leu Arg Ser Gly Asp Thr Ala Val Tyr Phe Cys
                85                  90                  95

Ala Arg Arg Glu Thr Thr Thr Val Gly Arg Tyr Tyr Tyr Ala Met Asp
            100                 105                 110

Tyr Trp Gly Lys Gly Thr Leu Val Thr Val Ser Ser Asp Ile Gln Leu
            115                 120                 125

Thr Gln Ser Pro Asp Ser Leu Ala Val Ser Leu Gly Glu Arg Ala Thr
        130                 135                 140

Ile Asn Cys Lys Ala Ser Gln Ser Val Asp Tyr Asp Gly Asp Ser Tyr
145                 150                 155                 160

Leu Asn Trp Tyr Gln Gln Lys Pro Gly Gln Pro Pro Lys Leu Leu Ile
                165                 170                 175

Tyr Asp Ala Ser Asn Leu Val Ser Gly Val Pro Asp Arg Phe Ser Gly
            180                 185                 190

Ser Gly Ser Gly Thr Asp Phe Thr Leu Thr Ile Ser Ser Leu Gln Ala
            195                 200                 205

Ala Asp Val Ala Val Tyr His Cys Gln Gln Ser Thr Glu Asp Pro Trp
        210                 215                 220

Thr Phe Gly Gln Gly Thr Lys Val Glu Ile Lys Arg
225                 230                 235
```

<210> SEQ ID NO 86
<211> LENGTH: 236
<212> TYPE: PRT
<213> ORGANISM: Artificial Sequence
<220> FEATURE:
<223> OTHER INFORMATION: Humanised CD19ALAb scFv sequence - Heavy 19,
      Kappa 7

<400> SEQUENCE: 86

```
Gln Val Gln Leu Val Gln Ser Gly Ala Glu Val Lys Lys Pro Gly Ala
1               5                   10                  15

Ser Val Lys Leu Ser Cys Lys Ala Ser Gly Tyr Ala Phe Ser Ser Tyr
            20                  25                  30

Trp Met Asn Trp Val Arg Gln Ala Pro Gly Gln Ser Leu Glu Trp Ile
        35                  40                  45

Gly Gln Ile Trp Pro Gly Asp Gly Asp Thr Asn Tyr Asn Gly Lys Phe
    50                  55                  60

Lys Gly Arg Ala Thr Leu Thr Ala Asp Glu Ser Ala Arg Thr Ala Tyr
65                  70                  75                  80

Met Glu Leu Ser Ser Leu Arg Ser Gly Asp Thr Ala Val Tyr Phe Cys
                85                  90                  95

Ala Arg Arg Glu Thr Thr Thr Val Gly Arg Tyr Tyr Tyr Ala Met Asp
            100                 105                 110

Tyr Trp Gly Lys Gly Thr Leu Val Thr Val Ser Ser Asp Ile Gln Leu
            115                 120                 125

Thr Gln Ser Pro Asp Ser Leu Ala Val Ser Leu Gly Glu Arg Ala Thr
        130                 135                 140

Ile Asn Cys Lys Ala Ser Gln Ser Val Asp Tyr Asp Gly Asp Ser Tyr
145                 150                 155                 160

Leu Asn Trp Tyr Gln Gln Lys Pro Gly Gln Pro Pro Lys Val Leu Ile
                165                 170                 175

Tyr Asp Ala Ser Asn Leu Val Ser Gly Val Pro Asp Arg Phe Ser Gly
            180                 185                 190

Ser Gly Ser Gly Thr Asp Phe Thr Leu Thr Ile Ser Ser Leu Gln Ala
            195                 200                 205
```

-continued

Ala Asp Val Ala Val Tyr Tyr Cys Gln Gln Ser Thr Glu Asp Pro Trp
    210                 215                 220

Thr Phe Gly Gln Gly Thr Lys Val Glu Ile Lys Arg
225                 230                 235

<210> SEQ ID NO 87
<211> LENGTH: 124
<212> TYPE: PRT
<213> ORGANISM: Artificial Sequence
<220> FEATURE:
<223> OTHER INFORMATION: Murine CD19ALAb VH sequence

<400> SEQUENCE: 87

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser
            115                 120

<210> SEQ ID NO 88
<211> LENGTH: 124
<212> TYPE: PRT
<213> ORGANISM: Artificial Sequence
<220> FEATURE:
<223> OTHER INFORMATION: Humanised CD19ALAb VH sequence

<400> SEQUENCE: 88

Gln Val Gln Leu Val Gln Ser Gly Ala Glu Val Lys Lys Pro Gly Ala
1               5                   10                  15

Ser Val Lys Leu Ser Cys Lys Ala Ser Gly Tyr Ala Phe Ser Ser Tyr
            20                  25                  30

Trp Met Asn Trp Val Arg Gln Ala Pro Gly Gln Ser Leu Glu Trp Ile
        35                  40                  45

Gly Gln Ile Trp Pro Gly Asp Gly Asp Thr Asn Tyr Asn Gly Lys Phe
    50                  55                  60

Lys Gly Arg Ala Thr Leu Thr Ala Asp Glu Ser Ala Arg Thr Ala Tyr
65                  70                  75                  80

Met Glu Leu Ser Ser Leu Arg Ser Gly Asp Thr Ala Val Tyr Phe Cys
                85                  90                  95

Ala Arg Arg Glu Thr Thr Thr Val Gly Arg Tyr Tyr Tyr Ala Met Asp
            100                 105                 110

Tyr Trp Gly Lys Gly Thr Leu Val Thr Val Ser Ser
            115                 120

<210> SEQ ID NO 89
<211> LENGTH: 111
<212> TYPE: PRT
<213> ORGANISM: Artificial Sequence

```
<220> FEATURE:
<223> OTHER INFORMATION: Murine CD19ALAb VL sequence

<400> SEQUENCE: 89

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys
            100                 105                 110

<210> SEQ ID NO 90
<211> LENGTH: 112
<212> TYPE: PRT
<213> ORGANISM: Artificial Sequence
<220> FEATURE:
<223> OTHER INFORMATION: Humanised CD19ALAb VL sequence, Kappa 16

<400> SEQUENCE: 90

Asp Ile Gln Leu Thr Gln Ser Pro Asp Ser Leu Ala Val Ser Leu Gly
1               5                   10                  15

Glu Arg Ala Thr Ile Asn Cys Lys Ala Ser Gln Ser Val Asp Tyr Asp
            20                  25                  30

Gly Asp Ser Tyr Leu Asn Trp Tyr Gln Gln Lys Pro Gly Gln Pro Pro
        35                  40                  45

Lys Leu Leu Ile Tyr Asp Ala Ser Asn Leu Val Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Ala Asp Val Ala Val Tyr His Cys Gln Gln Ser Thr
                85                  90                  95

Glu Asp Pro Trp Thr Phe Gly Gln Gly Thr Lys Val Glu Ile Lys Arg
            100                 105                 110

<210> SEQ ID NO 91
<211> LENGTH: 112
<212> TYPE: PRT
<213> ORGANISM: Artificial Sequence
<220> FEATURE:
<223> OTHER INFORMATION: Humanised CD19ALAb VL sequence, Kappa 7

<400> SEQUENCE: 91

Asp Ile Gln Leu Thr Gln Ser Pro Asp Ser Leu Ala Val Ser Leu Gly
1               5                   10                  15

Glu Arg Ala Thr Ile Asn Cys Lys Ala Ser Gln Ser Val Asp Tyr Asp
            20                  25                  30

Gly Asp Ser Tyr Leu Asn Trp Tyr Gln Gln Lys Pro Gly Gln Pro Pro
        35                  40                  45

Lys Val Leu Ile Tyr Asp Ala Ser Asn Leu Val Ser Gly Val Pro Asp
    50                  55                  60
```

```
Arg Phe Ser Gly Ser Gly Ser Gly Thr Asp Phe Thr Leu Thr Ile Ser
 65                  70                  75                  80

Ser Leu Gln Ala Ala Asp Val Ala Val Tyr Tyr Cys Gln Gln Ser Thr
                 85                  90                  95

Glu Asp Pro Trp Thr Phe Gly Gln Gly Thr Lys Val Glu Ile Lys Arg
            100                 105                 110

<210> SEQ ID NO 92
<211> LENGTH: 20
<212> TYPE: PRT
<213> ORGANISM: Artificial Sequence
<220> FEATURE:
<223> OTHER INFORMATION: cleavage site, 2A-like sequence

<400> SEQUENCE: 92

Arg Ala Glu Gly Arg Gly Ser Leu Leu Thr Cys Gly Asp Val Glu Glu
 1               5                  10                  15

Asn Pro Gly Pro
            20

<210> SEQ ID NO 93
<211> LENGTH: 5
<212> TYPE: PRT
<213> ORGANISM: Artificial Sequence
<220> FEATURE:
<223> OTHER INFORMATION: VH CDR sequence, CDR1

<400> SEQUENCE: 93

Asn Phe Ala Met Ala
 1               5

<210> SEQ ID NO 94
<211> LENGTH: 17
<212> TYPE: PRT
<213> ORGANISM: Artificial Sequence
<220> FEATURE:
<223> OTHER INFORMATION: VH CDR sequence, CDR2

<400> SEQUENCE: 94

Ser Ile Ser Thr Gly Gly Gly Asn Thr Tyr Tyr Arg Asp Ser Val Lys
 1               5                  10                  15

Gly

<210> SEQ ID NO 95
<211> LENGTH: 18
<212> TYPE: PRT
<213> ORGANISM: Artificial Sequence
<220> FEATURE:
<223> OTHER INFORMATION: VH CDR sequence, CDR3

<400> SEQUENCE: 95

Gln Arg Asn Tyr Tyr Asp Gly Ser Tyr Asp Tyr Glu Gly Tyr Thr Met
 1               5                  10                  15

Asp Ala

<210> SEQ ID NO 96
<211> LENGTH: 11
<212> TYPE: PRT
<213> ORGANISM: Artificial Sequence
<220> FEATURE:
<223> OTHER INFORMATION: VL CDR sequence, CDR1
```

```
<400> SEQUENCE: 96

Arg Ser Ser Gln Asp Ile Gly Asn Tyr Leu Thr
1               5                   10

<210> SEQ ID NO 97
<211> LENGTH: 7
<212> TYPE: PRT
<213> ORGANISM: Artificial Sequence
<220> FEATURE:
<223> OTHER INFORMATION: VL CDR sequence, CDR2

<400> SEQUENCE: 97

Gly Ala Ile Lys Leu Glu Asp
1               5

<210> SEQ ID NO 98
<211> LENGTH: 7
<212> TYPE: PRT
<213> ORGANISM: Artificial Sequence
<220> FEATURE:
<223> OTHER INFORMATION: VL CDR sequence, CDR3

<400> SEQUENCE: 98

Leu Gln Ser Ile Gln Tyr Pro
1               5

<210> SEQ ID NO 99
<211> LENGTH: 124
<212> TYPE: PRT
<213> ORGANISM: Artificial Sequence
<220> FEATURE:
<223> OTHER INFORMATION: VH sequence from 1G3-4 antibody

<400> SEQUENCE: 99

Gln Val Thr Leu Lys Glu Ser Gly Pro Gly Ile Leu Gln Pro Ser Gln
1               5                   10                  15

Thr Leu Ser Leu Thr Cys Thr Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Thr Asn Ile Trp Trp Asp Asp Lys Asn Tyr Asn Pro Ser
    50                  55                  60

Leu Lys Asn Arg Leu Thr Ile Ser Lys Asp Thr Ser Ile Asn Gln Ala
65                  70                  75                  80

Phe Leu Lys Ile Thr Asn Val Asp Thr Ala Asp Thr Ala Thr Tyr Tyr
                85                  90                  95

Cys Ala Arg Ile Ala His Tyr Phe Asp Gly Tyr Tyr Tyr Val Met Asp
            100                 105                 110

Val Trp Gly Gln Gly Thr Ser Val Thr Val Ser Ser
        115                 120

<210> SEQ ID NO 100
<211> LENGTH: 107
<212> TYPE: PRT
<213> ORGANISM: Artificial Sequence
<220> FEATURE:
<223> OTHER INFORMATION: VL sequence from 1G3-4 antibody

<400> SEQUENCE: 100

Asp Ile Gln Met Thr Gln Ser Pro Ala Ser Leu Ser Ala Ser Leu Gly
1               5                   10                  15
```

-continued

```
Glu Thr Val Ser Ile Glu Cys Leu Ala Ser Gly Gly Ile Ser Asn Asp
             20                  25                  30

Leu Ala Trp Tyr Gln Gln Lys Ser Gly Lys Pro Gln Leu Leu Ile
         35                  40                  45

Tyr Ala Ala Ser Arg Leu Gln Asp Gly Val Pro Ser Arg Phe Ser Gly
 50                  55                  60

Ser Gly Ser Gly Thr Arg Tyr Ser Leu Lys Ile Ser Gly Met Gln Ser
 65                  70                  75                  80

Glu Asp Glu Ala Asp Tyr Phe Cys Gln Gln Ser Tyr Lys Tyr Pro Tyr
                 85                  90                  95

Thr Phe Gly Gly Gly Thr Lys Leu Glu Leu Lys
                100                 105
```

<210> SEQ ID NO 101
<211> LENGTH: 7
<212> TYPE: PRT
<213> ORGANISM: Artificial Sequence
<220> FEATURE:
<223> OTHER INFORMATION: VH CDR sequence, CDR1

<400> SEQUENCE: 101

```
Thr Ser Gly Met Gly Val Gly
 1               5
```

<210> SEQ ID NO 102
<211> LENGTH: 16
<212> TYPE: PRT
<213> ORGANISM: Artificial Sequence
<220> FEATURE:
<223> OTHER INFORMATION: VH CDR sequence, CDR2

<400> SEQUENCE: 102

```
Asn Ile Trp Trp Asp Asp Lys Asn Tyr Asn Pro Ser Leu Lys Asn
 1               5                  10                  15
```

<210> SEQ ID NO 103
<211> LENGTH: 14
<212> TYPE: PRT
<213> ORGANISM: Artificial Sequence
<220> FEATURE:
<223> OTHER INFORMATION: VH CDR sequence, CDR3

<400> SEQUENCE: 103

```
Ile Ala His Tyr Phe Asp Gly Tyr Tyr Tyr Val Met Asp Val
 1               5                  10
```

<210> SEQ ID NO 104
<211> LENGTH: 11
<212> TYPE: PRT
<213> ORGANISM: Artificial Sequence
<220> FEATURE:
<223> OTHER INFORMATION: VL CDR sequence, CDR1

<400> SEQUENCE: 104

```
Leu Ala Ser Gly Gly Ile Ser Asn Asp Leu Ala
 1               5                  10
```

<210> SEQ ID NO 105
<211> LENGTH: 7
<212> TYPE: PRT
<213> ORGANISM: Artificial Sequence
<220> FEATURE:
<223> OTHER INFORMATION: VL CDR sequence, CDR2

```
<400> SEQUENCE: 105

Ala Ala Ser Arg Leu Gln Asp
1               5

<210> SEQ ID NO 106
<211> LENGTH: 8
<212> TYPE: PRT
<213> ORGANISM: Artificial Sequence
<220> FEATURE:
<223> OTHER INFORMATION: VL CDR sequence, CDR3

<400> SEQUENCE: 106

Gln Gln Ser Tyr Lys Tyr Pro Tyr
1               5

<210> SEQ ID NO 107
<211> LENGTH: 117
<212> TYPE: PRT
<213> ORGANISM: Artificial Sequence
<220> FEATURE:
<223> OTHER INFORMATION: VH sequence from 1F6 antibody

<400> SEQUENCE: 107

Gln Val Gln Leu Lys Glu Ser Gly Pro Gly Leu Val Gln Pro Ser Gln
1               5                   10                  15

Thr Leu Ser Leu Thr Cys Thr Val Ser Gly Phe Ser Leu Thr Ser Tyr
            20                  25                  30

Thr Val Ser Trp Val Arg Gln Pro Pro Gly Lys Gly Leu Glu Trp Ile
        35                  40                  45

Ala Ala Ile Ser Ser Gly Gly Ser Thr Tyr Tyr Asn Ser Ala Leu Lys
    50                  55                  60

Ser Arg Leu Ser Ile Ser Arg Asp Thr Ser Lys Ser Gln Val Phe Leu
65                  70                  75                  80

Lys Met Asn Ser Leu Gln Thr Glu Asp Thr Ala Met Tyr Phe Cys Ala
                85                  90                  95

Arg Tyr Thr Thr Asp Ser Gly Phe Asp Tyr Trp Gly Gln Gly Val Met
            100                 105                 110

Val Thr Val Ser Ser
            115

<210> SEQ ID NO 108
<211> LENGTH: 106
<212> TYPE: PRT
<213> ORGANISM: Artificial Sequence
<220> FEATURE:
<223> OTHER INFORMATION: VL sequence from 1F6 antibody

<400> SEQUENCE: 108

Asp Ile Gln Met Thr Gln Ser Pro Ser Val Leu Ser Ala Ser Val Gly
1               5                   10                  15

Asp Arg Val Thr Leu Ser Cys Lys Ala Ser Gln Asn Ile Asn Lys Asn
            20                  25                  30

Leu Asp Trp Tyr Gln Gln Lys Leu Gly Glu Ala Pro Lys Leu Leu Ile
        35                  40                  45

Tyr Phe Thr Asn Asn Leu Gln Thr Gly Ile Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Val Ala Thr Tyr Tyr Cys Tyr Gln Tyr Asn Ser Gly Trp Thr
                85                  90                  95
```

Phe Gly Gly Gly Thr Lys Leu Glu Leu Lys
            100                 105

<210> SEQ ID NO 109
<211> LENGTH: 122
<212> TYPE: PRT
<213> ORGANISM: Artificial Sequence
<220> FEATURE:
<223> OTHER INFORMATION: VH sequence from 2H9 antibody

<400> SEQUENCE: 109

Glu Val Gln Leu Val Glu Ser Gly Gly Asp Leu Val Gln Pro Gly Arg
1               5                   10                  15

Ser Leu Lys Leu Ser Cys Ala Ser Ser Gly Phe Thr Phe Ser Asp Tyr
            20                  25                  30

Asn Met Ala Trp Val Arg Gln Ala Pro Lys Lys Gly Leu Glu Trp Val
        35                  40                  45

Ala Thr Ile Ser Tyr Asp Gly Thr Asn Thr Tyr Tyr Arg Asp Ser Val
    50                  55                  60

Lys Gly Arg Phe Thr Ile Ser Arg Asp Asn Ala Lys Ser Thr Leu Tyr
65                  70                  75                  80

Leu Gln Met Asp Ser Leu Arg Ser Glu Asp Thr Ala Thr Tyr Tyr Cys
                85                  90                  95

Ala Arg Gln Asp Ser Ser Tyr Val Tyr Leu Ser Trp Phe Ala Tyr Trp
            100                 105                 110

Gly Gln Gly Thr Leu Val Thr Val Ser Ser
        115                 120

<210> SEQ ID NO 110
<211> LENGTH: 107
<212> TYPE: PRT
<213> ORGANISM: Artificial Sequence
<220> FEATURE:
<223> OTHER INFORMATION: VL sequence from 2H9 antibody

<400> SEQUENCE: 110

Asp Ile Gln Met Thr Gln Ser Pro Ala Ser Leu Ser Ala Ser Leu Gly
1               5                   10                  15

Glu Thr Val Thr Ile Glu Cys Arg Ala Ser Glu Asp Ile Tyr Asn Gly
            20                  25                  30

Leu Thr Trp Tyr Gln Gln Lys Pro Gly Lys Ser Pro Gln Leu Leu Ile
        35                  40                  45

Ser Asn Ala Asn Cys Leu His Thr Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Val Ala Ser Tyr Phe Cys Gln Gln Tyr Asn Tyr Pro Trp
                85                  90                  95

Thr Phe Gly Gly Gly Thr Lys Leu Asp Leu Lys
            100                 105

<210> SEQ ID NO 111
<211> LENGTH: 117
<212> TYPE: PRT
<213> ORGANISM: Artificial Sequence
<220> FEATURE:
<223> OTHER INFORMATION: VH sequence from 7F10 antibody

```
<400> SEQUENCE: 111

Gln Val Gln Leu Lys Glu Ser Gly Pro Gly Leu Val Gln Pro Ser Gln
1               5                   10                  15

Thr Leu Ser Leu Thr Cys Thr Val Ser Gly Phe Ser Leu Thr Ser Tyr
            20                  25                  30

Thr Val Ser Trp Val Arg Gln Pro Pro Gly Arg Gly Leu Glu Trp Ile
        35                  40                  45

Ala Ala Ile Ser Ser Gly Gly Asn Thr Tyr Tyr Asn Ser Gly Leu Lys
    50                  55                  60

Ser Arg Leu Ser Ile Ser Arg Asp Thr Ser Lys Ser Gln Val Phe Leu
65                  70                  75                  80

Lys Met Asn Ser Leu Gln Thr Glu Asp Thr Ala Met Tyr Phe Cys Ala
                85                  90                  95

Arg Tyr Ala Gln Ile Arg Gly Lys Asp Tyr Trp Gly Gln Gly Val Met
            100                 105                 110

Val Thr Val Ser Ser
            115

<210> SEQ ID NO 112
<211> LENGTH: 106
<212> TYPE: PRT
<213> ORGANISM: Artificial Sequence
<220> FEATURE:
<223> OTHER INFORMATION: VL sequence from 7F10 antibody

<400> SEQUENCE: 112

Asp Ile Gln Met Thr Gln Ser Pro Pro Ile Leu Ser Ala Ser Val Gly
1               5                   10                  15

Asp Arg Val Thr Leu Ser Cys Lys Ala Ser Gln Asn Ile Asn Lys Asn
            20                  25                  30

Leu Asp Trp Tyr Gln Gln Lys His Gly Glu Ala Pro Lys Leu Leu Ile
        35                  40                  45

Tyr Tyr Thr His Asn Leu Gln Thr Gly Ile Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Val Ala Thr Tyr Tyr Cys Tyr Gln Tyr Tyr Ser Gly Trp Thr
                85                  90                  95

Phe Gly Gly Gly Thr Lys Leu Gln Leu Lys
            100                 105

<210> SEQ ID NO 113
<211> LENGTH: 5
<212> TYPE: PRT
<213> ORGANISM: Artificial Sequence
<220> FEATURE:
<223> OTHER INFORMATION: VH CDR sequence, CDR1

<400> SEQUENCE: 113

Ser Tyr Thr Val Ser
1               5

<210> SEQ ID NO 114
<211> LENGTH: 16
<212> TYPE: PRT
<213> ORGANISM: Artificial Sequence
<220> FEATURE:
<223> OTHER INFORMATION: VH CDR sequence, CDR2
```

```
<400> SEQUENCE: 114

Ala Ile Ser Ser Gly Gly Ser Thr Tyr Tyr Asn Ser Ala Leu Lys Ser
1               5                   10                  15

<210> SEQ ID NO 115
<211> LENGTH: 9
<212> TYPE: PRT
<213> ORGANISM: Artificial Sequence
<220> FEATURE:
<223> OTHER INFORMATION: VH CDR sequence, CDR3

<400> SEQUENCE: 115

Tyr Thr Thr Asp Ser Gly Phe Asp Tyr
1               5

<210> SEQ ID NO 116
<211> LENGTH: 11
<212> TYPE: PRT
<213> ORGANISM: Artificial Sequence
<220> FEATURE:
<223> OTHER INFORMATION: VL CDR sequence, CDR1

<400> SEQUENCE: 116

Lys Ala Ser Gln Asn Ile Asn Lys Asn Leu Asp
1               5                   10

<210> SEQ ID NO 117
<211> LENGTH: 7
<212> TYPE: PRT
<213> ORGANISM: Artificial Sequence
<220> FEATURE:
<223> OTHER INFORMATION: VL CDR sequence, CDR2

<400> SEQUENCE: 117

Phe Thr Asn Asn Leu Gln Thr
1               5

<210> SEQ ID NO 118
<211> LENGTH: 8
<212> TYPE: PRT
<213> ORGANISM: Artificial Sequence
<220> FEATURE:
<223> OTHER INFORMATION: VL CDR sequence, CDR3

<400> SEQUENCE: 118

Tyr Gln Tyr Asn Ser Gly Trp Thr
1               5

<210> SEQ ID NO 119
<211> LENGTH: 5
<212> TYPE: PRT
<213> ORGANISM: Artificial Sequence
<220> FEATURE:
<223> OTHER INFORMATION: VH CDR sequence, CDR1

<400> SEQUENCE: 119

Asp Tyr Asn Met Ala
1               5

<210> SEQ ID NO 120
<211> LENGTH: 17
<212> TYPE: PRT
<213> ORGANISM: Artificial Sequence
<220> FEATURE:
<223> OTHER INFORMATION: VH CDR sequence, CDR2
```

```
<400> SEQUENCE: 120

Thr Ile Ser Tyr Asp Gly Thr Asn Thr Tyr Tyr Arg Asp Ser Val Lys
1               5                   10                  15

Gly

<210> SEQ ID NO 121
<211> LENGTH: 13
<212> TYPE: PRT
<213> ORGANISM: Artificial Sequence
<220> FEATURE:
<223> OTHER INFORMATION: VH CDR sequence, CDR3

<400> SEQUENCE: 121

Gln Asp Ser Ser Tyr Val Tyr Leu Ser Trp Phe Ala Tyr
1               5                   10

<210> SEQ ID NO 122
<211> LENGTH: 11
<212> TYPE: PRT
<213> ORGANISM: Artificial Sequence
<220> FEATURE:
<223> OTHER INFORMATION: VL CDR sequence, CDR1

<400> SEQUENCE: 122

Arg Ala Ser Glu Asp Ile Tyr Asn Gly Leu Thr
1               5                   10

<210> SEQ ID NO 123
<211> LENGTH: 7
<212> TYPE: PRT
<213> ORGANISM: Artificial Sequence
<220> FEATURE:
<223> OTHER INFORMATION: VL CDR sequence, CDR2

<400> SEQUENCE: 123

Asn Ala Asn Cys Leu His Thr
1               5

<210> SEQ ID NO 124
<211> LENGTH: 9
<212> TYPE: PRT
<213> ORGANISM: Artificial Sequence
<220> FEATURE:
<223> OTHER INFORMATION: VL CDR sequence, CDR3

<400> SEQUENCE: 124

Gln Gln Tyr Tyr Asn Tyr Pro Trp Thr
1               5

<210> SEQ ID NO 125
<211> LENGTH: 5
<212> TYPE: PRT
<213> ORGANISM: Artificial Sequence
<220> FEATURE:
<223> OTHER INFORMATION: VH CDR sequence, CDR1

<400> SEQUENCE: 125

Ser Tyr Thr Val Ser
1               5

<210> SEQ ID NO 126
<211> LENGTH: 16
<212> TYPE: PRT
<213> ORGANISM: Artificial Sequence
<220> FEATURE:
<223> OTHER INFORMATION: VH CDR sequence, CDR2
```

<400> SEQUENCE: 126

Ala Ile Ser Ser Gly Gly Asn Thr Tyr Tyr Asn Ser Gly Leu Lys Ser
1               5                   10                  15

<210> SEQ ID NO 127
<211> LENGTH: 9
<212> TYPE: PRT
<213> ORGANISM: Artificial Sequence
<220> FEATURE:
<223> OTHER INFORMATION: VH CDR sequence, CDR3

<400> SEQUENCE: 127

Tyr Ala Gln Ile Arg Gly Lys Asp Tyr
1               5

<210> SEQ ID NO 128
<211> LENGTH: 11
<212> TYPE: PRT
<213> ORGANISM: Artificial Sequence
<220> FEATURE:
<223> OTHER INFORMATION: VL CDR sequence, CDR1

<400> SEQUENCE: 128

Lys Ala Ser Gln Asn Ile Asn Lys Asn Leu Asp
1               5                   10

<210> SEQ ID NO 129
<211> LENGTH: 7
<212> TYPE: PRT
<213> ORGANISM: Artificial Sequence
<220> FEATURE:
<223> OTHER INFORMATION: VL CDR sequence, CDR2

<400> SEQUENCE: 129

Tyr Thr His Asn Leu Gln Thr
1               5

<210> SEQ ID NO 130
<211> LENGTH: 8
<212> TYPE: PRT
<213> ORGANISM: Artificial Sequence
<220> FEATURE:
<223> OTHER INFORMATION: VL CDR sequence, CDR3

<400> SEQUENCE: 130

Tyr Gln Tyr Tyr Ser Gly Trp Thr
1               5

<210> SEQ ID NO 131
<211> LENGTH: 5
<212> TYPE: PRT
<213> ORGANISM: Artificial Sequence
<220> FEATURE:
<223> OTHER INFORMATION: glycine-serine linker

<400> SEQUENCE: 131

Gly Gly Gly Gly Ser
1               5

<210> SEQ ID NO 132
<211> LENGTH: 5
<212> TYPE: PRT
<213> ORGANISM: Artificial Sequence
<220> FEATURE:
<223> OTHER INFORMATION: VH CDR sequence, CDR1

```
<400> SEQUENCE: 132

Asn Tyr Gly Met Asn
1               5

<210> SEQ ID NO 133
<211> LENGTH: 16
<212> TYPE: PRT
<213> ORGANISM: Artificial Sequence
<220> FEATURE:
<223> OTHER INFORMATION: VH CDR sequence, CDR2

<400> SEQUENCE: 133

Arg Ile Tyr Pro Gly Ser Gly Ser Thr Asn Tyr Gln Lys Phe Lys Gly
1               5                   10                  15

<210> SEQ ID NO 134
<211> LENGTH: 16
<212> TYPE: PRT
<213> ORGANISM: Artificial Sequence
<220> FEATURE:
<223> OTHER INFORMATION: VL CDR sequence, CDR1

<400> SEQUENCE: 134

Arg Ser Ser Gln Ser Ile Val His Ser Asn Gly Asn Thr Tyr Leu Glu
1               5                   10                  15

<210> SEQ ID NO 135
<211> LENGTH: 7
<212> TYPE: PRT
<213> ORGANISM: Artificial Sequence
<220> FEATURE:
<223> OTHER INFORMATION: VL CDR sequence, CDR2

<400> SEQUENCE: 135

Lys Val Ser Asn Arg Pro Ser
1               5

<210> SEQ ID NO 136
<211> LENGTH: 9
<212> TYPE: PRT
<213> ORGANISM: Artificial Sequence
<220> FEATURE:
<223> OTHER INFORMATION: VL CDR sequence, CDR3

<400> SEQUENCE: 136

Phe Gln Gly Ser His Val Pro Trp Thr
1               5
```

UNITED STATES PATENT AND TRADEMARK OFFICE
CERTIFICATE OF CORRECTION

| | | |
|---|---|---|
| PATENT NO. | : 11,963,981 B2 | Page 1 of 1 |
| APPLICATION NO. | : 17/054670 | |
| DATED | : April 23, 2024 | |
| INVENTOR(S) | : Martin Pulé et al. | |

It is certified that error appears in the above-identified patent and that said Letters Patent is hereby corrected as shown below:

In the Claims

Column 135, Line 39, Claim 7, "shown as" should be -- shown in --.

Column 135, Line 52, Claim 8, "a a" should be -- a --.

Column 136, Line 5, Claim 8, "a a" should be -- a --.

Column 136, Line 22, Claim 14, "comprises" should be -- comprises: --.

Column 136, Line 52, Claim 15, "shown as" should be -- shown in --.

Signed and Sealed this
Twenty-ninth Day of October, 2024

Katherine Kelly Vidal
*Director of the United States Patent and Trademark Office*